(12) United States Patent
Sahin et al.

(10) Patent No.: US 11,541,127 B2
(45) Date of Patent: Jan. 3, 2023

(54) DRUG CONJUGATES COMPRISING ANTIBODIES AGAINST CLAUDIN 18.2

(71) Applicants: Ganymed Pharmaceuticals GmbH, Mainz (DE); TRON—Translationale Onkologie an der Universitatsmedizin der Johannes Gutenberg-Universitat Mainz GGMBH, Mainz (DE)

(72) Inventors: Ugur Sahin, Mainz (DE); Ozlem Tureci, Mainz (DE); Korden Walter, Saulheim (DE); Maria Kreuzberg, Mainz (DE); Rita Mitnacht-Kraus, Friedberg (DE); Fabrice Le Gall, Mainz (DE); Stefan Jacobs, Mainz-Kastel (DE)

(73) Assignees: Astellas Pharma, Inc., Tokyo (JP); TRON—Translationale Onkologie an der Universitätsmedizin der Johannes Gutenberg-Universität Mainz gemeinnützige GmbH, Mainz (DE)

( * ) Notice: Subject to any disclaimer, the term of this patent is extended or adjusted under 35 U.S.C. 154(b) by 374 days.

(21) Appl. No.: 15/565,848

(22) PCT Filed: Apr. 13, 2016

(86) PCT No.: PCT/EP2016/058056
§ 371 (c)(1),
(2) Date: Oct. 11, 2017

(87) PCT Pub. No.: WO2016/166122
PCT Pub. Date: Oct. 20, 2016

(65) Prior Publication Data
US 2018/0117174 A1 May 3, 2018

(30) Foreign Application Priority Data

Apr. 15, 2015 (WO) .................. PCT/EP2015/058206

(51) Int. Cl.
| | |
|---|---|
| *A61K 39/00* | (2006.01) |
| *A61K 47/68* | (2017.01) |
| *C07K 16/30* | (2006.01) |
| *C07K 16/28* | (2006.01) |
| *A61P 35/04* | (2006.01) |
| *A61P 35/00* | (2006.01) |
| *A61K 31/40* | (2006.01) |

(52) U.S. Cl.
CPC .......... *A61K 47/6859* (2017.08); *A61K 31/40* (2013.01); *A61K 47/6803* (2017.08); *A61K 47/6849* (2017.08); *A61K 47/6863* (2017.08); *A61P 35/00* (2018.01); *A61P 35/04* (2018.01); *C07K 16/28* (2013.01); *C07K 16/303* (2013.01); *C07K 16/3046* (2013.01); *A61K 2039/505* (2013.01); *A61K 2039/627* (2013.01); *C07K 2317/24* (2013.01); *C07K 2317/732* (2013.01); *C07K 2317/734* (2013.01); *C07K 2317/77* (2013.01); *C07K 2317/92* (2013.01)

(58) Field of Classification Search
CPC ................................................ A61K 2039/505
See application file for complete search history.

(56) References Cited

U.S. PATENT DOCUMENTS

| | | | |
|---|---|---|---|
| 2010/0316639 A1 | 12/2010 | Lackner | |
| 2015/0315287 A1 * | 11/2015 | Tureci ...................... | C12N 9/88 424/133.1 |
| 2017/0320963 A1 * | 11/2017 | Sahin ...................... | A61P 13/12 |

FOREIGN PATENT DOCUMENTS

| | | | |
|---|---|---|---|
| EP | 1 997 832 A1 | 12/2008 | |
| EP | 1997832 A1 * | 12/2008 | ......... C07K 16/3046 |
| MX | 2014013542 A | 5/2015 | |
| WO | WO-2008145338 A2 * | 12/2008 | ......... C07K 16/3046 |
| WO | WO 2013/174404 A1 | 11/2013 | |
| WO | WO 2014/146778 A1 | 9/2014 | |
| WO | WO 2015/014870 A1 | 2/2015 | |
| WO | WO 2016/166122 A1 | 10/2016 | |
| WO | WO-2016165765 A1 * | 10/2016 | ......... A61K 47/6801 |

OTHER PUBLICATIONS

Niimi et al. (Mol. Cell. Biol. Nov. 2001; 21 (21): 7380-90).*
George et al. (Circulation. 1998; 97: 900-906).*
Greenspan et al. (Nature Biotechnology. 1999; 7: 936-937).*
Buus et al. (Mol. Cell. Proteomics. Dec. 2012; 11 (12): 1790-1800).*
Jiang et al. (J. Biol. Chem. Feb. 11, 2005; 280 (6): 4656-4662).*
Rudikoff etal (Proc. Natl. Acad. Sci. USA. 1982; 79: 1979-1983).*
Mariuzza et al. (Annu. Rev. Biophys. Biophys. Chem. 1987; 16: 139-159).*
Winkler et al. (J. Immunol. Oct. 15, 2000; 165 (8): 4505-4514).*
Gussow et al. (Methods in Enzymology. 1991; 203: 99-121).*
Giusti et al. (Proc. Natl. Acad. Sci. USA. May 1987; 84 (9): 2926-2930).*

(Continued)

*Primary Examiner* — Stephen L Rawlings
(74) *Attorney, Agent, or Firm* — Neal, Gerber & Eisenberg LLP; Kevin A. O'Connor

(57) ABSTRACT

The present invention provides anti-CLDN18.2 antibody-drug conjugates which are effective for treating and/or preventing cancer diseases associated with cells expressing CLDN18.2, including gastric cancer, esophageal cancer, pancreatic cancer, lung cancer, ovarian cancer, colon cancer, hepatic cancer, head-neck cancer, and cancer of the gallbladder and metastases thereof.

28 Claims, 26 Drawing Sheets
Specification includes a Sequence Listing.

(56) References Cited

OTHER PUBLICATIONS

Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yamaguchi et al. (Biochem. Biophys. Res. Commun. Nov. 1, 2014; 454 (4): 600-603).*
Yip et al. (J. Immunol. Apr. 15, 2001; 166 (8): 5271-8).*
Cochran et al. (J. Immunol. Methods. Apr. 2004; 287 (1-2): 147-58).*
Bernard et al. (Human Immunol. 1986; 17: 388-405).*
Pettersen et al. (J. Immunol. Jun. 15, 1999; 162 (12): 7031-7040).*
Kreuzberg et al. (Annals Oncol. Sep. 2017; 28 (Suppl. 5): 176 (Abstract#377P)).*
Verma et al. (N. Engl. J. Med. Nov. 8, 2012; 367 (19): 1783-91).*
Smith et al. (Br. J. Cancer. Jul. 8, 2008; 99 (1): 100-9).*
Francisco et al. (Blood. Aug. 15, 2003; 102 (4): 1458-65).*
Lopus (Cancer Lett. Aug. 28, 2011; 307 (2): 113-8).*
Sherbenou et al. (Blood Rev. Mar. 2015; 29 (2): 81-91; author manuscript; pp. 1-30).*
Tanaka et al. (J. Histochem. Cytochem. Oct. 2011; 59 (10): 942-52).*
Woll et al. (Int. J. Cancer. Feb. 1, 2014; 134 (3): 731-9).*
Sahin et al. (Clin. Cancer Res. Dec. 1, 2008; 14 (23): 7624-34).*
Srinivasarao et al. (Nat. Rev. Drug Discov. Mar. 2015; 14 (3): 203-19).*
Jain et al. (Pharm. Res. 2015; 32 (11): 3526-354).*
Widdison et al. (J. Med. Chem. Jul. 13, 2006; 49 (14): 4392-408).*
Perez et al. (Drug Discov. Today. Jul. 2014; 19 (7): 869-81).*
Lavie et al. (Cancer Immunol. Immunother. 1991; 33 (4): 223-30).*
Casi et al. (Mol. Pharm. Jun. 1, 2015; 12 (6): 1880-4).*
Bernardes et al. (Angew Chem. Int. Ed. Engl. Jan. 23, 2012; 51 (4): 941-4).*
Jackson et al. (Pharm. Res. Nov. 2015; 32 (11): 3458-69).*
Polson et al. (Cancer Res. Mar. 15, 2009; 69 (6): 2358-64).*
Bryan et al. (Cancer Biol. Ther. Jun. 15, 2011; 11 (12): 1001-7).*
Dal Corso et al. (Bioconjug. Chem. Jul. 19, 2017; 28 (7): 1826-1833).*
Joubert et al. (Eur. J. Med. Chem. Dec. 15, 2017; 142: 393-415).*
Kim et al. (Biomol. Ther. (Seoul). Nov. 2015; 23 (6): 493-509).*
Anchetta et al. (Toxins (Basel). Mar. 2, 2022; 14 (3):184; pp. 1-29).*
Gebleux et al. (Mol. Cancer Ther. Nov. 2015; 14 (11): 2606-12).*
Giansanti et al. (J. Control. Release. Jan. 28, 2019; 294: 176-184).*
Staudacher et al. (Br. J. Cancer. Dec. 5, 2017; 117 (12): 1736-1742).*
Ganymed Pharmaceuticals AG: "Ideal Monoclonal Antibodies against Cancer: $2^{nd}$ Generation IMAB," [http://www.ganymed-pharmaceuticals.com/pipeline/$2^{nd}$-generation-imab.html retrieved on Dec. 3, 2015].
Kominsky, Scott L., "Claudins: Emerging targets for cancer therapy," *Expert Reviews in Molecular Medicine*, 8(18): 1-11 (Aug. 2006) (Abstract).
Sahin et al., *Clinical Cancer Research*, 14(23): 7624-7634 (Dec. 2008).
European Patent Office, International Search Report for International Application No. PCT/EP2016/058056 (dated Jun. 24, 2016).
European Patent Office, Written Opinion of the International Searching Authority for International Application No. PCT/EP2016/058056 (dated Jun. 24, 2016).
The International Bureau of WIPO, International Preliminary Report on Patentability for International Application No. PCT/EP2016/058056 (dated Oct. 17, 2017).
Riechmann et al., Nature, 332: 323-327 (1988).
"Cell Culture Experts Association, Institute of Cytology of the Russian Academy of Sciences" Cell Cultures. News Letter. Issue 26, St. Petersburg, ISSN 2077-6055 (2010).
"GANYMED Pharmaceuticals AG's IMAB027 Enters Phase I/II Clinical Trial for Ovarian Cancer." Feb. 12, 2014, https://www.biospace.com/article/releases/ganymed-pharmaceuticals-ag-s-imab027-enters-phase-i-ii-clinical-trial-for-ovarian-cancer-/ (3 pages).

* cited by examiner

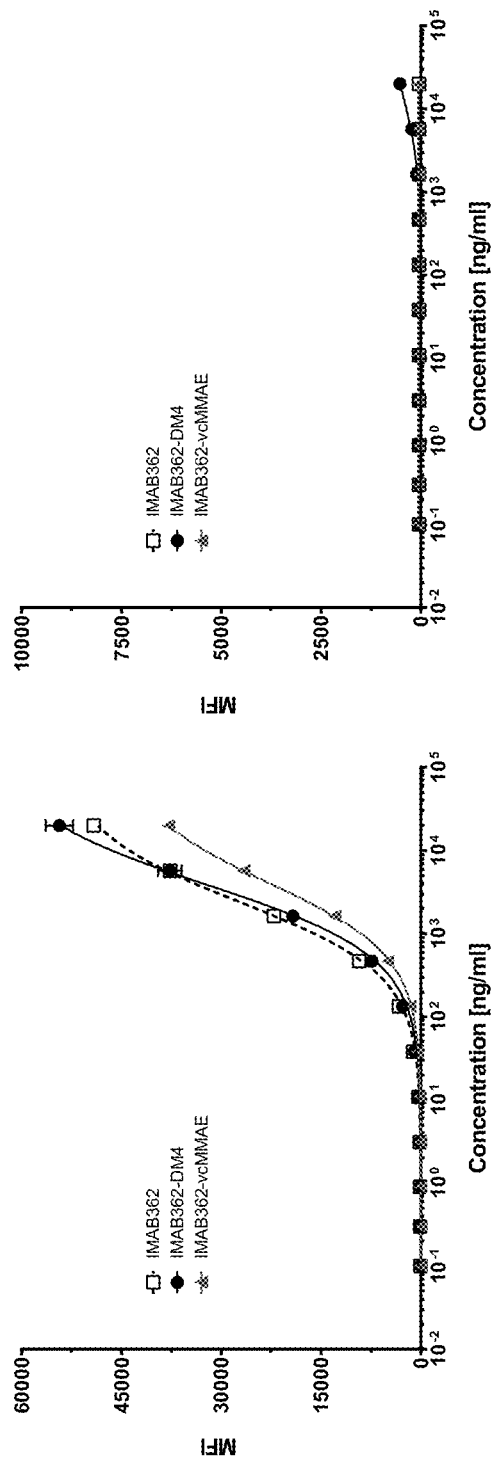
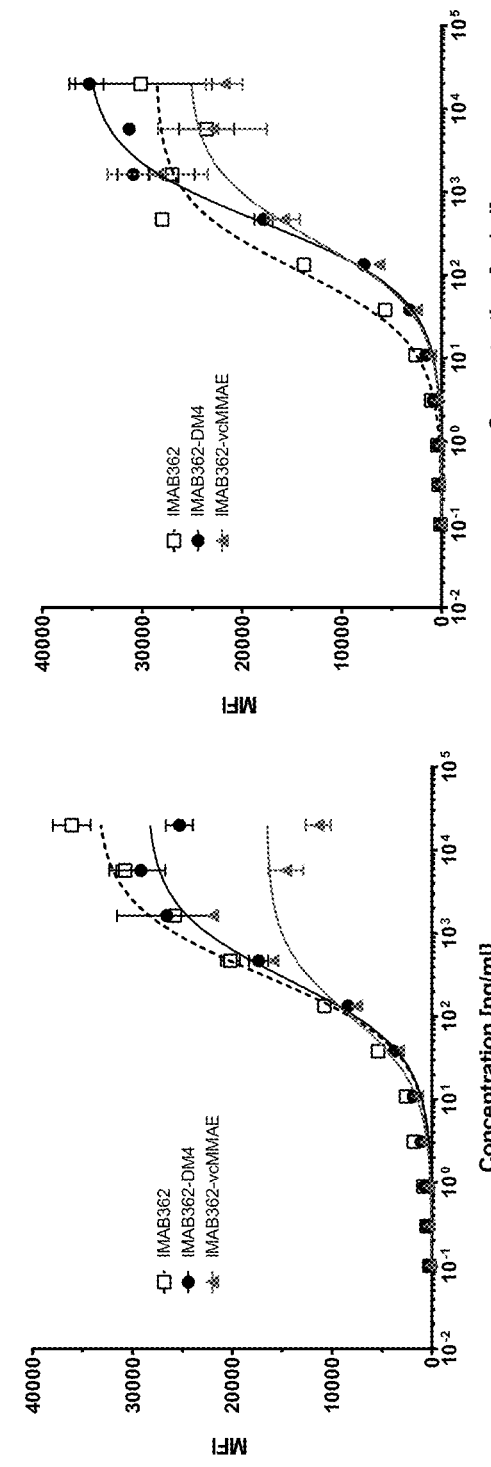

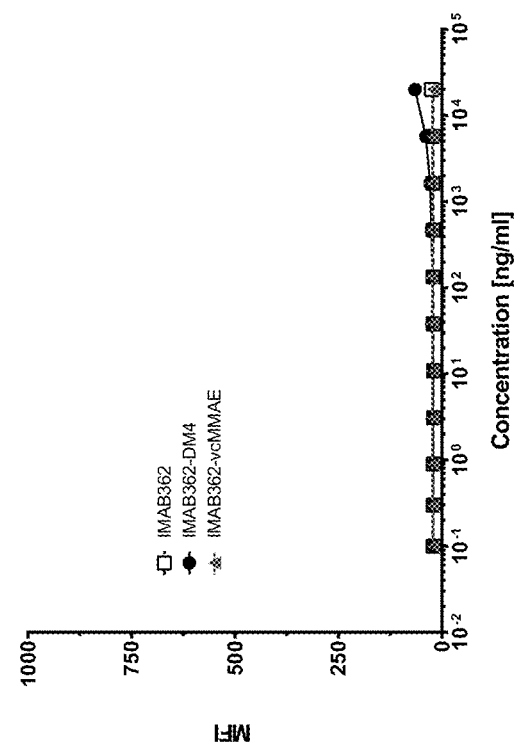
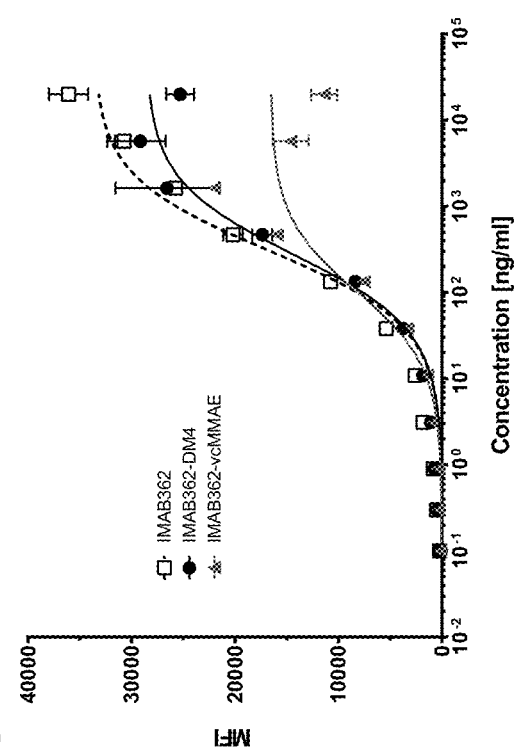

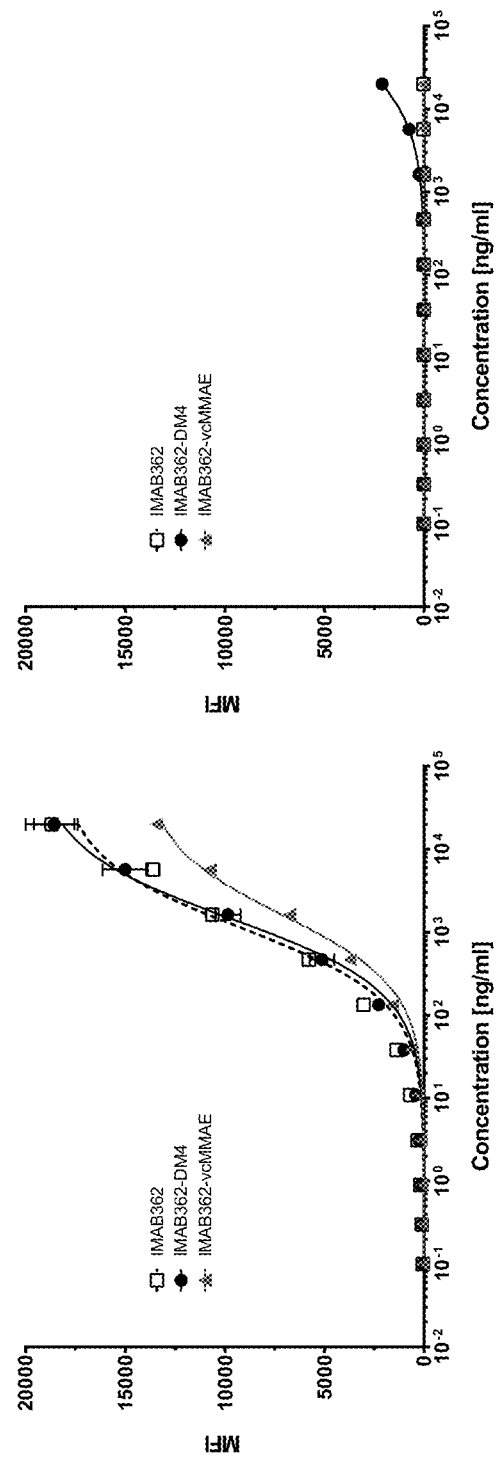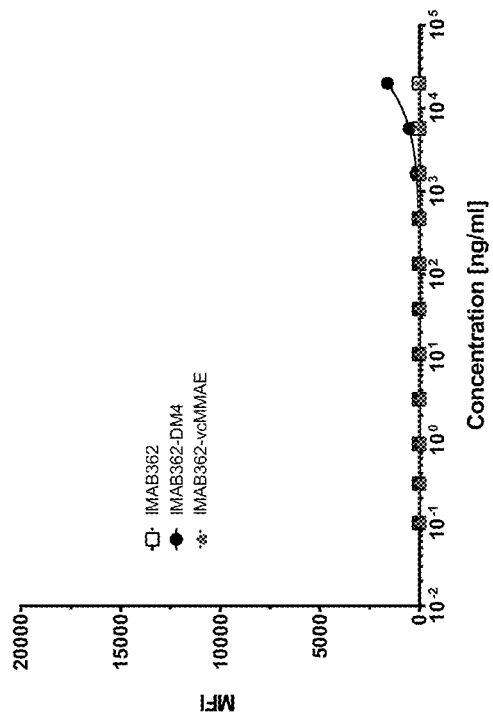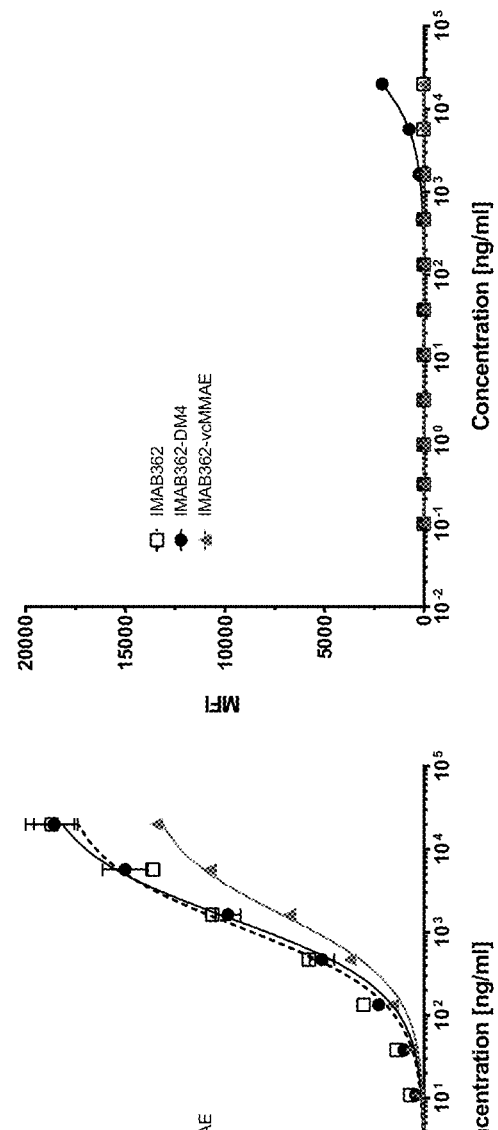

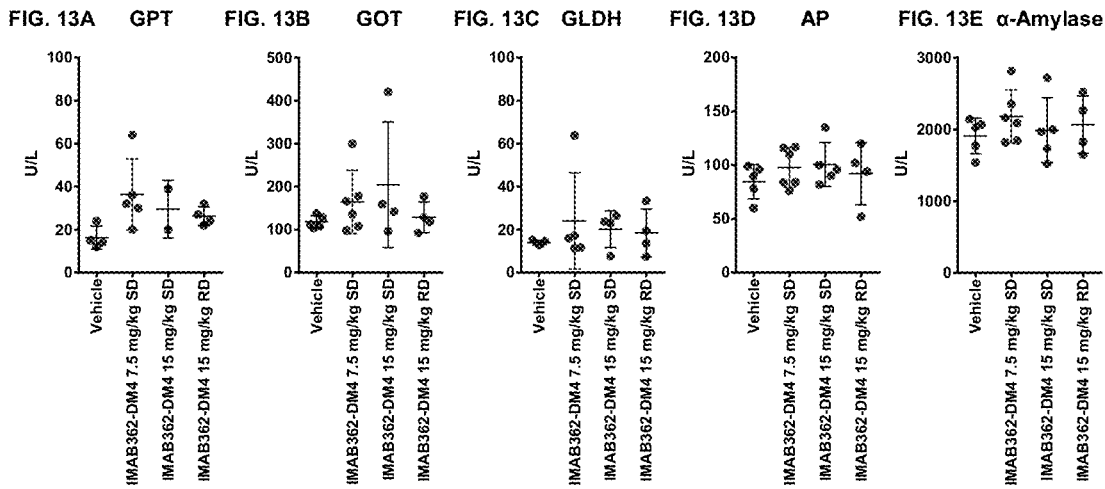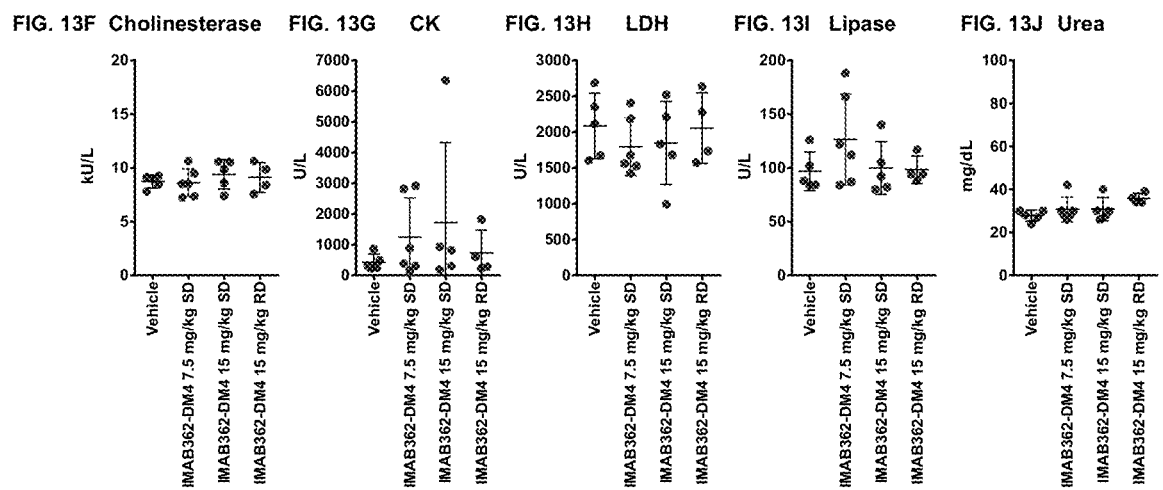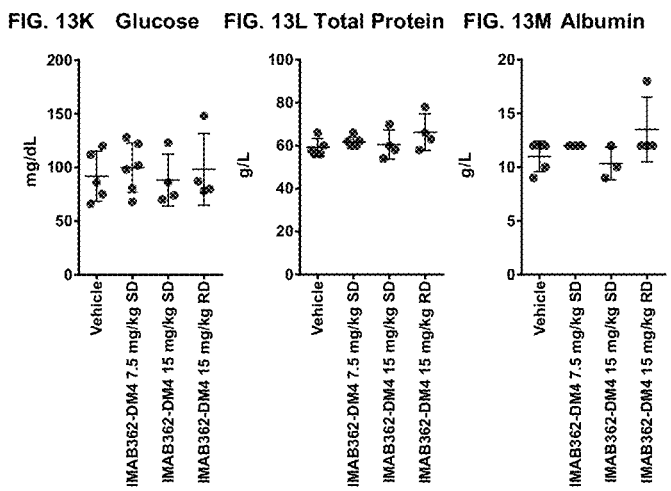

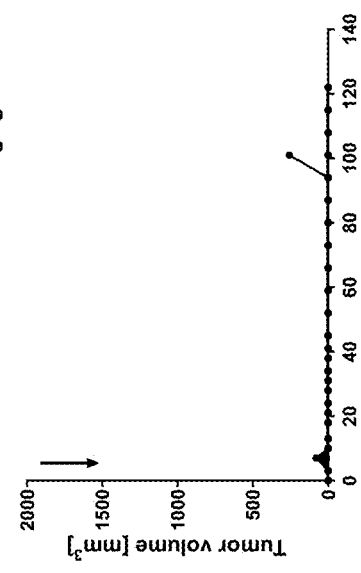
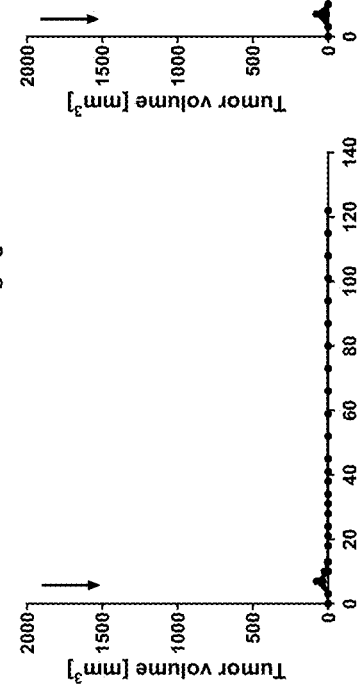
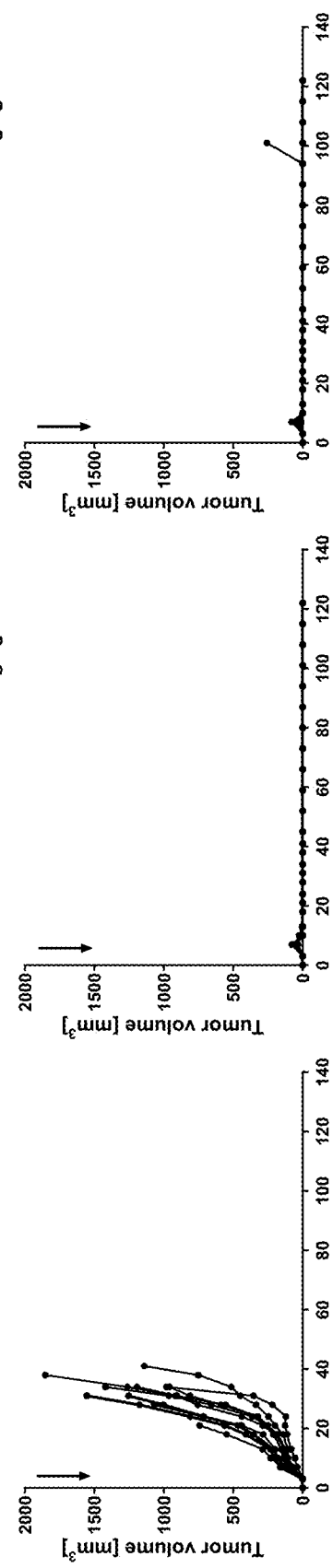
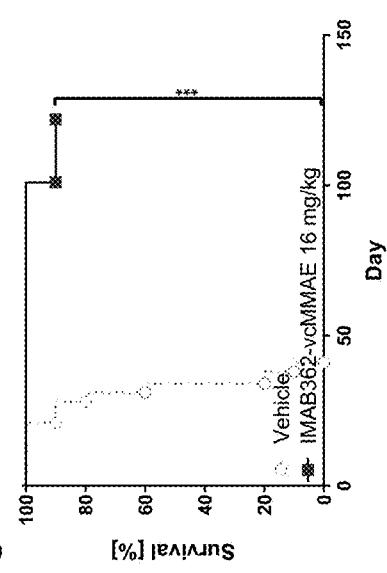
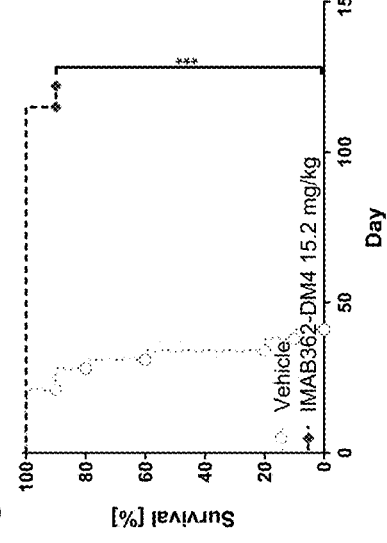
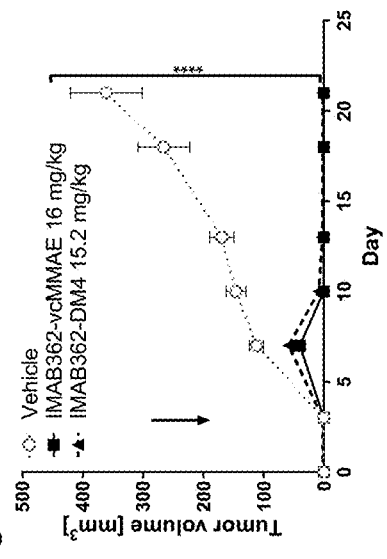

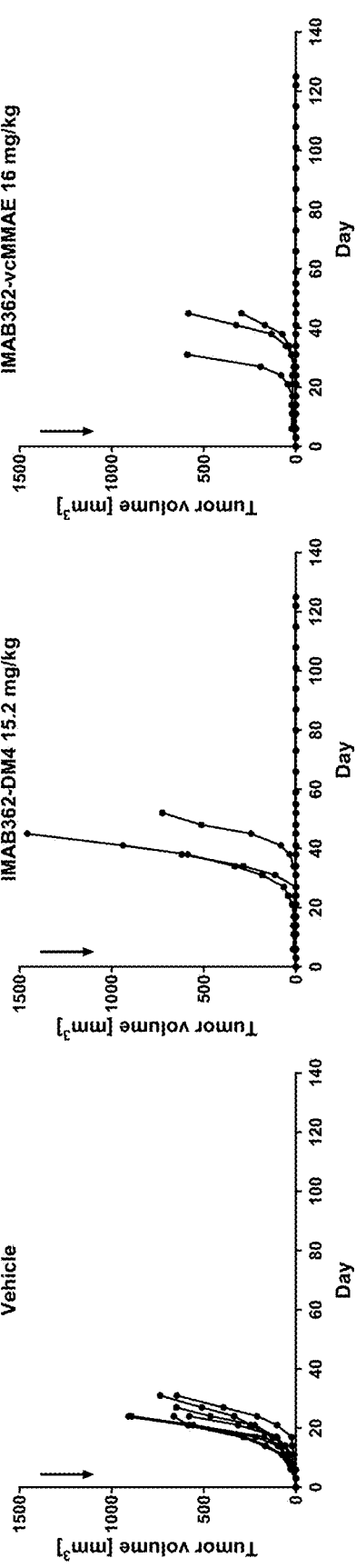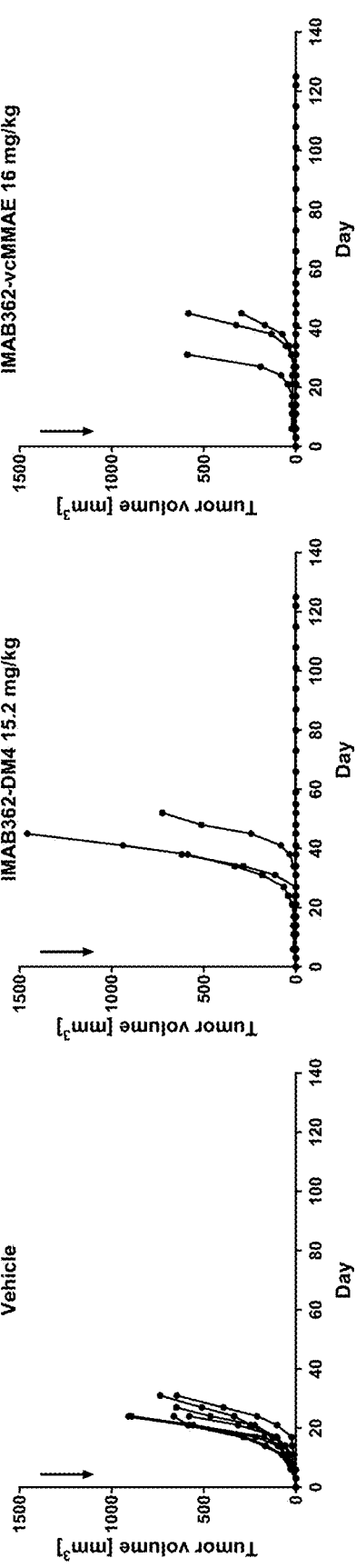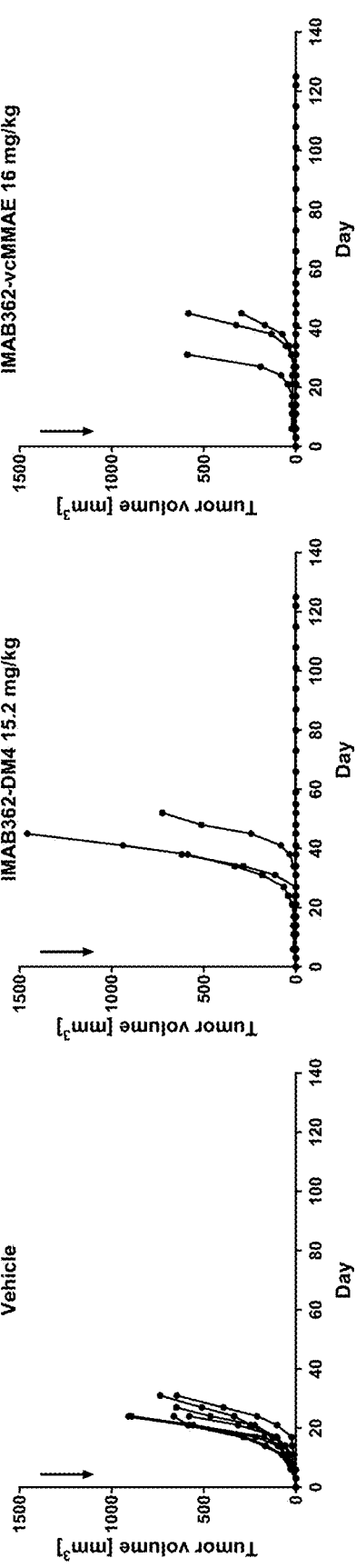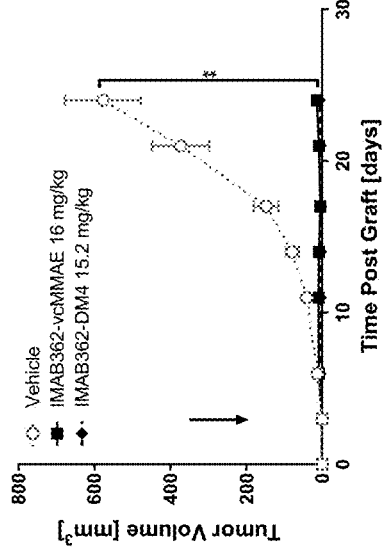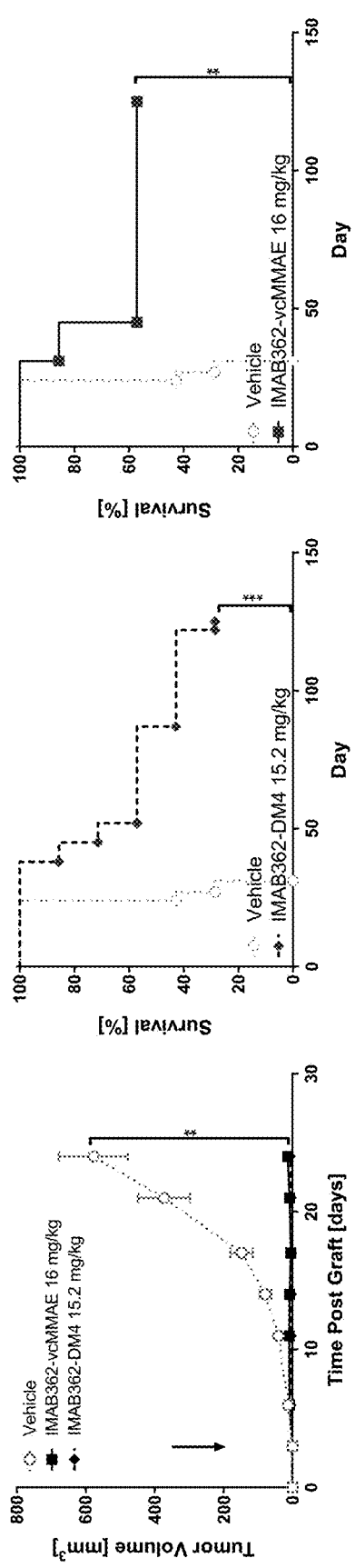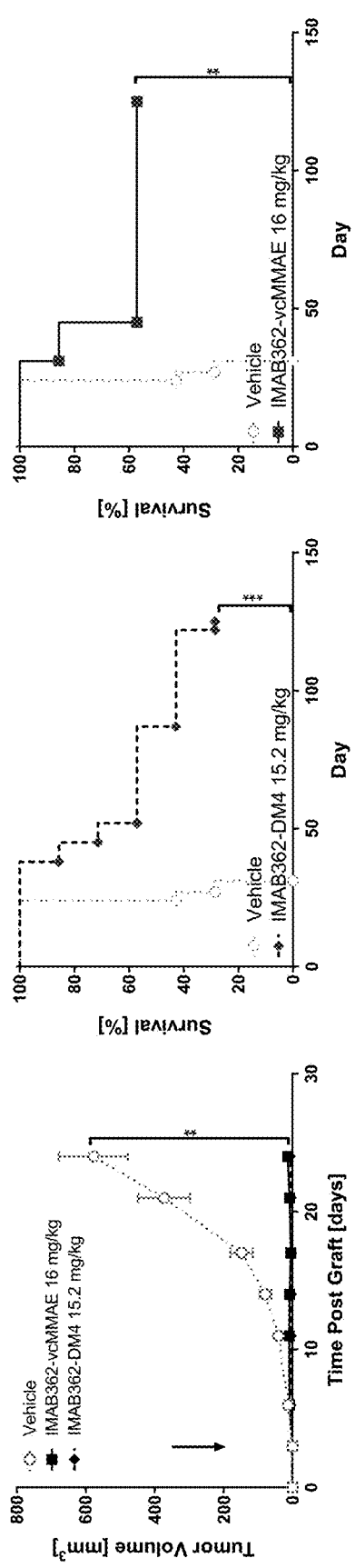

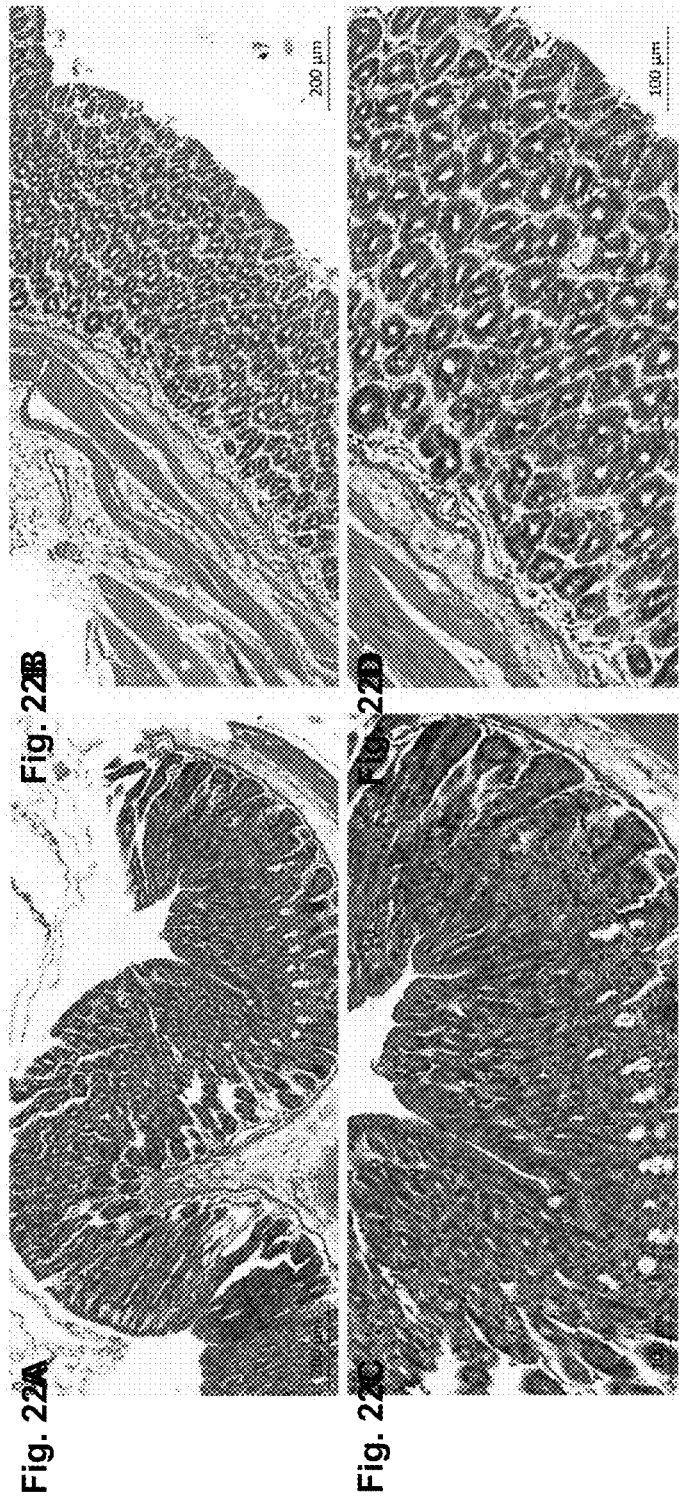

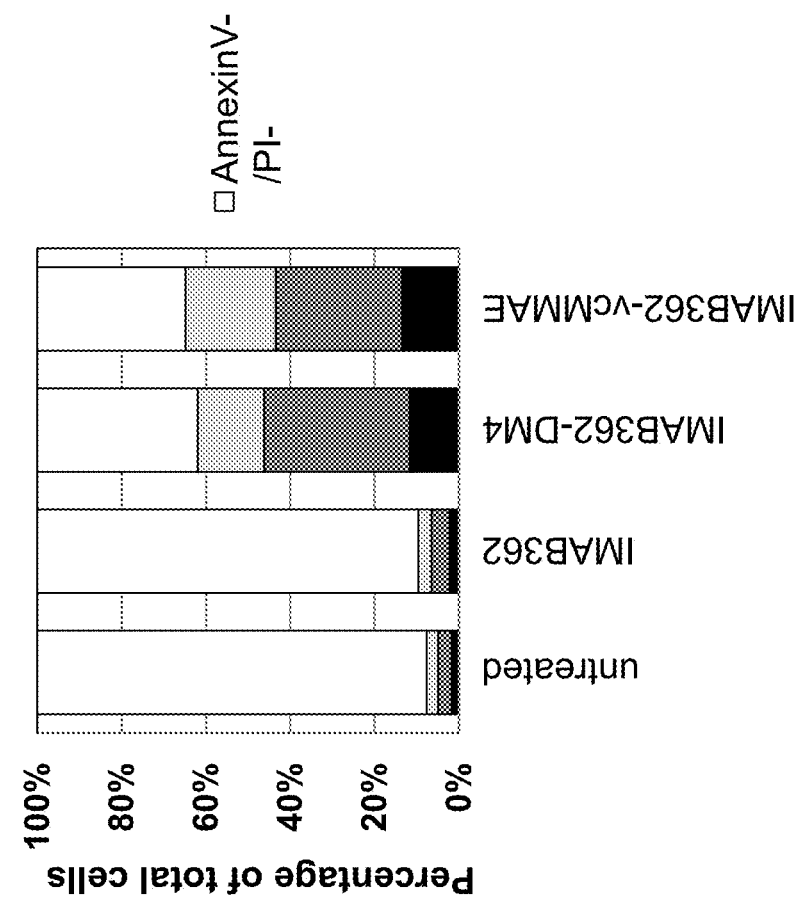
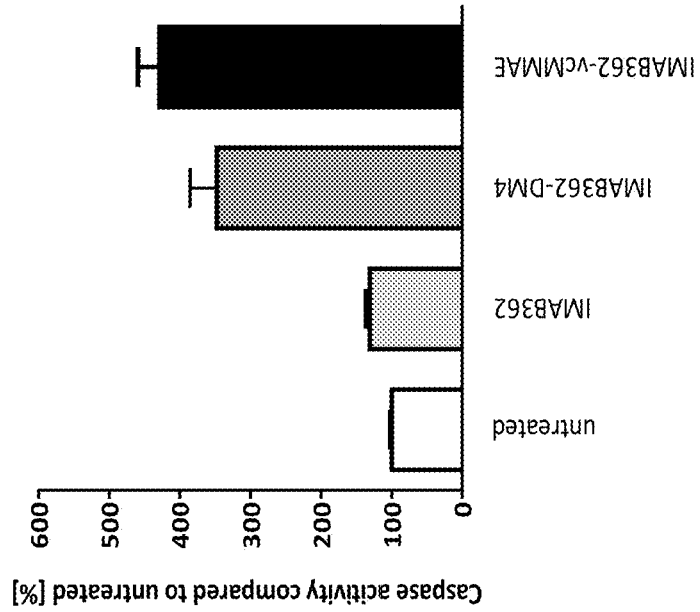
Fig. 23A
Fig. 23B

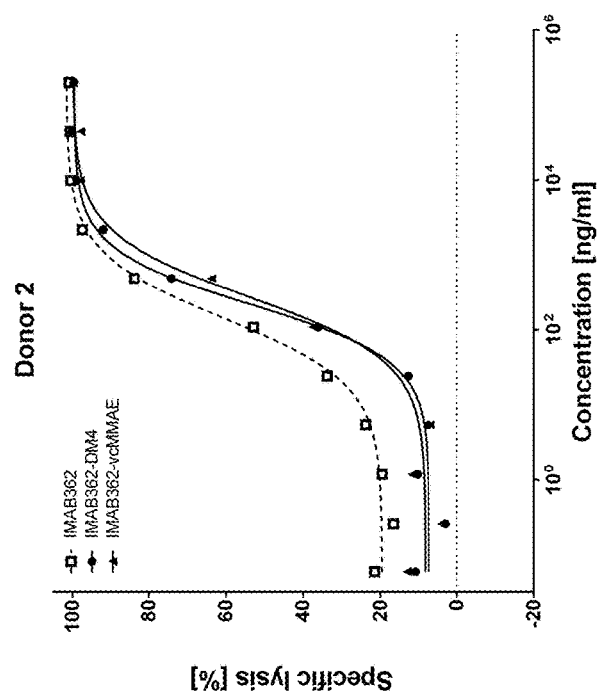
Fig. 25A
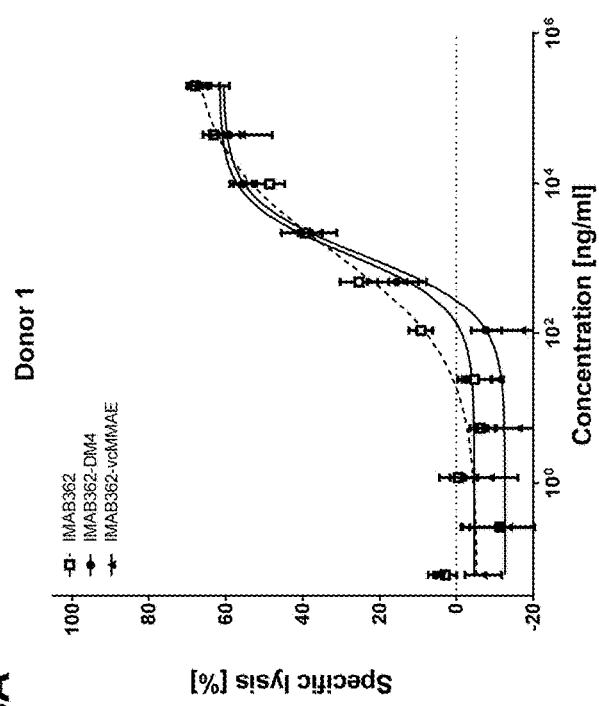
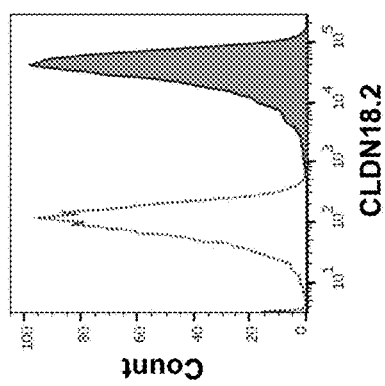
Fig. 25B

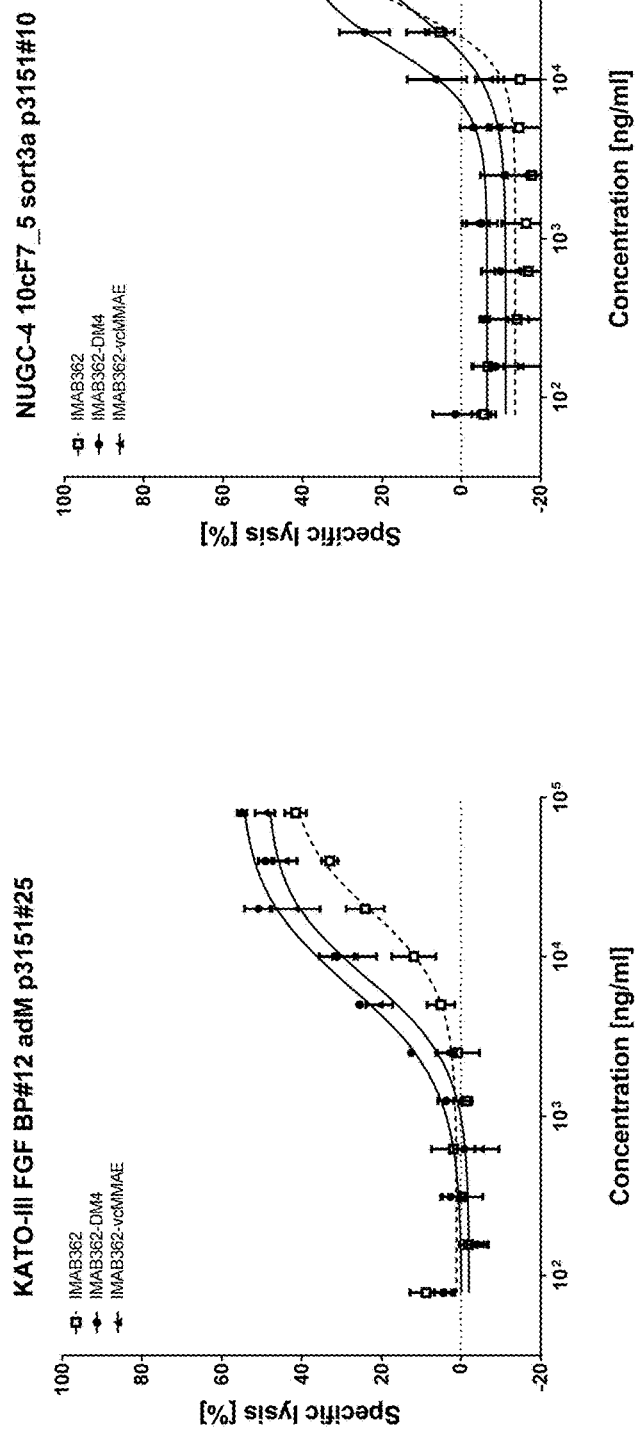
*Fig. 26A*
*Fig. 26B*

DRUG CONJUGATES COMPRISING ANTIBODIES AGAINST CLAUDIN 18.2

CROSS REFERENCE TO RELATED APPLICATIONS

This application is a national stage entry of international application PCT/EP2016/058056, which was filed on Apr. 13, 2016 and claimed priority to international application PCT/EP2015/058206, which was filed on Apr. 15, 2015, the entire contents of which are incorporated herein by reference.

BACKGROUND

Monoclonal antibodies (mABs) have revolutionized the treatment of cancer over the past two decades (Sliwkowski, M. X. et al. (2013) Science 341 (6151), 1192-1198). A critical feature of mABs is their high specificity and their ability to target tumor cells, marking them for immune-effector mediated cell killing (complement-dependent cytotoxicity (CDC), antibody-dependent cellular cytotoxicity (ADCC)) and/or leading to reduced proliferation and apoptosis (Kubota, T. et al. (2009) Cancer Sci. 100 (9), 1566-1572). Conjugation to cytotoxic drugs can expand the utility of mABs and improve their potency and effectiveness (Goldmacher, V. S. et al. (2011) Ther. Deliv. 2 (3), 397-416; Sievers, E. L. (2013) Annu. Rev. Med. 64, 15-29).

Historically, the use of cytotoxic drugs for the treatment of cancer has centered on chemotherapies that target dividing cancer cells. These compounds do not only target cancer cells but also other dividing healthy cells in the body, and patients receiving treatment experience severe side effects that limit the dose. The therapeutic index (maximum tolerated dose/minimum efficacious dose) for these drugs is low, resulting in a narrow therapeutic window (Ismael, G. F. V. et al. (2008) Cancer Treat Rev. 34 (1), 81-91). To circumvent this obstacle in drug development and improve the therapeutic index, antibodies can be used to deliver the cytotoxic drug specifically to the tumor. By combining the unique targeting capabilities of an antibody with the cancer-killing ability of a cytotoxic drug, antibody-drug conjugates (ADCs) exhibit lower side effects and provide a wider therapeutic window compared to traditional chemotherapeutic agents (Gerber, H.-P. et al. (2013) Nat. Prod. Rep. 30 (5), 625-639).

ADCs are designed to kill cancer cells in a target-dependent manner. The first step in this process is binding of the antibody to its antigen. Upon ADC binding, the entire antigen-ADC complex is internalized and the cytotoxic payload is released into the tumor cell resulting in cell death. Factors that influence the therapeutic index for ADCs include the antibody, the tumor target antigen, the cytotoxic drug and the linker (Panowksi, S. et al. (2014) MAbs 6 (1), 34-45). As a basic prerequisite for the development of ADCs, the tumor target antigen has to be localized on the cell surface and accessible to the circulating antibody. Furthermore, the tumor selectivity and the expression level of the target antigen are critical parameters for the design of safe and efficacious ADCs. Currently, a variety of tumor-associated cell surface antigens are being evaluated as ADC targets for cancer therapy (Trail, P. A. (2013) Antibodies 2 (1), 113-129; Teicher, B. A. (2009) Curr. Cancer Drug Targets 9 (8), 982-1004).

The efficiency of an ADC also depends on the cytotoxic drug. As the amount of an antibody that localizes to a tumor is very small compared to the administered dose, toxic compounds with sub-nanomolar potency are required. Auristatins and maytansinoids are two classes of highly potent cytotoxins currently used in ADC development (Trail, P. A. (2013) Antibodies 2 (1), 113-129). Both are antimitotic agents blocking the polymerization of tubulin causing cell death by a G2/M phase cell cycle arrest (Lopus, M. et al. (2010) Mol. Cancer Ther. 9 (10), 2689-2699; Francisco, J. A et al. (2003) Blood 102 (4), 1458-1465). In addition to the specificity of the mAB and potency of the drug, the linker is an important element in ADC development. The linker should be stable to exploit the pharmacokinetic half-life of the mAB and should not release the cytotoxic drug until antigen-mediated internalization. Linkers can be classified by their mechanism of drug release: Cleavable linkers release the drug by hydrolysis or enzymatic cleavage following antigen-specific internalization whereas non-cleavable linkers, release the drug via degradation of the mAB in lysosomes following internalization (Dosio, F. et al. (2011) Toxins (Basel) 3 (7), S. 848-883).

Depending on the linker design, membrane permeable (lipophilic) toxins that are released inside target positive cells can pass the cell membrane and kill other cells that are in close proximity, including neighboring cancer cells that lack antigen expression (bystander effect) (Kovtun, Y. V. et al. (2006) Cancer Res. 66 (6), 3214-3221). The ability of these cytotoxic drugs to mediate local bystander killing is an important selection criteria for those ADCs directed against antigens that are heterogeneously expressed in tumors.

The tight junction molecule claudin 18 isotype 2 (CLDN18.2) is a cancer-associated splice variant of Claudin 18. CLDN18.2 is a 27.8 kDa transmembrane protein comprising four membrane spanning domains with two small extracellular loops (loop1 embraced by hydrophobic region 1 and hydrophobic region 2; loop2 embraced by hydrophobic regions 3 and 4). CLDN18.2 is a highly selective gastric lineage antigen, exclusively expressed on short-lived differentiated gastric epithelial cells and not detectable in any other normal human tissue. The antigen is ectopically expressed at significant levels in a diversity of human cancers including gastroesophageal and pancreatic cancer (Sahin, U., et al., Clin Cancer Res, 2008. 14 (23): p. 7624-34). The CLDN18.2 protein is also frequently detected in lymph node metastases of gastric cancer and in distant metastases. CLDN18.2 seems to be involved in proliferation of CLDN18.2 positive tumor cells, since down regulation of the target by siRNA technology results in inhibition of proliferation of gastric cancer cells.

IMAB362 is a chimeric monoclonal antibody of IgG1 subtype directed against CLDN18.2. IMAB362 recognizes the first extracellular domain of CLDN18.2 with high affinity and specificity and does not bind to any other claudin family member including the closely related splice variant 1 of Claudin 18 (CLDN18.1). In human xenografts expressing CLDN18.2 survival benefit and tumor regressions have been observed in mice after administration of IMAB362. When administered intravenously in relevant animal species, no toxicity in gastric tissue is observed as the target epitope is not accessible. However, the tumor target becomes accessible for IMAB362 during malignant transformation. IMAB362 bundles four independent highly potent mechanisms of action: (i) antibody-dependent cellular cytotoxicity (ADCC), (ii) complement-dependent cytotoxicity (CDC), (iii) induction of apoptosis induced by cross linking of the target at the tumor surface and (iv) direct inhibition of proliferation. A previous phase I trial has evaluated IMAB362 as monotherapy in a single dose in patients with late-stage gastroesophageal cancer. This study shows that a single administration of this antibody is safe and well tolerated in a dosage of up to 1000 mg/m², as no relevant differences in AE profile and other safety parameters between the dose groups could be seen (AE=adverse event). Best results with regard to antitumoral activity were obtained for the 300 mg/m² and 600 mg/m² groups. A phase IIa clinical trial was conducted to determine safety, tolerability and antitumoral activity of repetitive doses of IMAB362 in patients with metastatic, refractory or recurrent disease of advanced adenocarcinoma of the stomach or the lower esophagus proven by histology.

As described above, CLDN18.2 has a restricted expression pattern in normal cells and, thus, appears to be an ideal target for antibody-directed therapy of cancer expressing CLDN18.2. Accordingly, there is a need for a therapy directed against CLDN18.2-expressing cancer cells that is capable of exerting a clinically useful cytotoxic or cytostatic effect on CLDN18.2-expressing cells, particularly without exerting undesirable effects on non-CLDN18.2-expressing cells. Preferably, the therapy should not be associated with disadvantages and undesirable side effects commonly associated with approaches that have been used for increasing the therapeutic efficacy of antibodies such as radiolabeling and combination with chemotherapy. For example, isotope therapy is associated with myelosuppression, and combination therapy with antibodies and chemotherapeutics is associated with immunosuppression. Further, isotopically labeled substances are difficult to produce, and patients often experience relapse after initial treatment with isotopically labeled substances.

The present invention demonstrates the existence of anti-CLDN18.2 monoclonal antibodies that can be highly efficiently internalized upon CLDN18.2 binding on CLND18.2-expressing cells and therefore are suitable for ADC development. Furthermore, the successful conjugation of such antibodies to the drugs DM4 and MMAE using cleavable SPDB or Val-Cit (vc) linkers, respectively, is disclosed. In vitro, the antibody conjugates reduce viability of gastric and pancreatic cancer cells expressing CLDN18.2. IMAB362-vcMMAE and IMAB362-DM4 do not bind to or influence viability of CLDN18.2 negative cells. Both, the DM4 and vcMMAE conjugates exert bystander killing effects on CLDN18.2 negative cancer cells co-cultured with CLDN18.2 positive cancer cells in vitro. Furthermore, in vivo, intravenous administration of the antibody conjugates in nude mice with CLDN18.2-positive gastric or pancreatic xenograft tumors results in dose-dependent tumor growth inhibition, survival benefit and even complete regression of early and advanced tumors. Significant therapeutic effects are observed at single dose intravenous application of ~4-8 mg/kg; optimal therapeutic effects are achieved at 15-16 mg/kg. The maximum tolerated single dose of both conjugates could not be determined as the highest possible tested doses of 15.2 and 16 mg/kg did not result in liver toxicities or other toxic effects.

From the data presented herein it can be concluded that anti-CLDN18.2 antibody-drug conjugates such as those described herein are highly potent drugs for the treatment of CLDN18.2-positive human carcinomas such as gastric and pancreatic carcinomas.

SUMMARY OF THE INVENTION

The present invention generally provides a therapy for effectively treating and/or preventing cancer associated with cells expressing CLDN18.2 such as gastric cancer, esophageal cancer, pancreatic cancer, lung cancer such as non small cell lung cancer (NSCLC), ovarian cancer, colon cancer, hepatic cancer, head-neck cancer, and cancer of the gallbladder and metastases thereof, in particular gastric cancer metastasis such as Krukenberg tumors, peritoneal metastasis and lymph node metastasis. Particularly preferred cancer diseases are adenocarcinomas of the stomach, the esophagus, the pancreatic duct, the bile ducts, the lung and the ovary.

In one aspect, the present invention provides a method of treating or preventing a CLDN18.2-expressing cancer comprising administering an antibody-drug conjugate comprising an antibody having the ability of binding to CLDN18.2 covalently attached to at least one toxin drug moiety to a cancer patient.

In one embodiment, the antibody-drug conjugate is internalized into cells following binding to CLDN18.2 expressed by the cells.

In one embodiment, the antibody having the ability of binding to CLDN18.2 specifically binds to CLDN18.2. In one embodiment, the antibody-drug conjugate specifically binds to CLDN18.2.

In one embodiment, the antibody having the ability of binding to CLDN18.2 is a monoclonal, chimeric or humanized antibody, or a fragment of an antibody. In one embodiment, the antibody having the ability of binding to CLDN18.2 is a monoclonal antibody.

In one embodiment, the antibody having the ability of binding to CLDN18.2 binds to native epitopes of CLDN18.2 present on the surface of living cells. In one embodiment, the antibody having the ability of binding to CLDN18.2 binds to an extracellular domain of CLDN18.2. In one embodiment, the antibody having the ability of binding to CLDN18.2 binds to the first extracellular loop of CLDN18.2.

In one embodiment, the antibody having the ability of binding to CLDN18.2 is an antibody selected from the group consisting of (i) an antibody produced by and/or obtainable from a clone deposited under the accession no. DSM ACC2737, DSM ACC2738, DSM ACC2739, DSM ACC2740, DSM ACC2741, DSM ACC2742, DSM ACC2743, DSM ACC2745, DSM ACC2746, DSM ACC2747, DSM ACC2748, DSM ACC2808, DSM ACC2809, or DSM ACC2810, (ii) an antibody which is a chimerized or humanized form of the antibody under (i), (iii) an antibody having the specificity of the antibody under (i) and (iv) an antibody comprising the antigen binding portion or antigen binding site, in particular the variable region, of the antibody under (i) and preferably having the specificity of the antibody under (i). In one embodiment, the antibody having the ability of binding to CLDN18.2 comprises a heavy chain comprising an amino acid sequence represented by SEQ ID NO: 32 or a fragment thereof or a variant of said amino acid sequence or fragment and a light chain comprising an amino acid sequence represented by SEQ ID NO: 39 or a fragment thereof or a variant of said amino acid sequence or fragment. In one embodiment, the antibody having the ability of binding to CLDN18.2 comprises a heavy chain comprising an amino acid sequence represented by SEQ ID NO: 17 or 51 or a fragment thereof or a variant of said amino acid sequence or fragment and a light chain comprising an amino acid sequence represented by SEQ ID NO: 24 or a fragment thereof or a variant of said amino acid sequence or fragment. In one embodiment, the antibody having the ability of binding to CLDN18.2 comprises a heavy chain comprising an amino acid sequence represented by SEQ ID NO: 30 or a fragment thereof or a variant of said amino acid sequence or fragment and a light chain comprising an amino acid sequence represented by SEQ ID NO: 35 or a fragment thereof or a variant of said amino acid sequence or fragment. In one embodiment, the antibody having the ability of binding to CLDN18.2 comprises a heavy chain comprising an amino acid sequence represented by SEQ ID NO: 15 or a fragment thereof or a variant of said amino acid sequence or fragment and a light chain comprising an amino acid sequence represented by SEQ ID NO: 20 or a fragment thereof or a variant of said amino acid sequence or fragment. In one embodiment, the antibody having the ability of binding to CLDN18.2 recognizes the same or essentially the same epitope as a CLDN18.2-binding antibody comprising a heavy chain comprising an amino acid sequence represented by SEQ ID NO: 32 or a fragment thereof or a variant of said amino acid sequence or fragment and a light chain comprising an amino acid sequence represented by SEQ ID NO: 39 or a fragment thereof or a variant of said amino acid sequence or fragment, and/or competes with said CLDN18.2-binding antibody for binding to CLDN18.2. In one embodiment, the antibody having the ability of binding to CLDN18.2 recognizes the same or essentially the same epitope as a CLDN18.2-binding antibody comprising a heavy chain comprising an amino acid sequence represented by SEQ ID NO: 17 or 51 or a fragment thereof or a variant of said amino acid sequence or fragment and a light chain comprising an amino acid sequence represented by SEQ ID NO: 24 or a fragment thereof or a variant of said amino acid sequence or fragment, and/or competes with said CLDN18.2-binding antibody for binding to CLDN18.2. In one embodiment, the antibody having the ability of binding to CLDN18.2 recognizes the same or essentially the same epitope as a CLDN18.2-binding antibody comprising a heavy chain comprising an amino acid sequence represented by SEQ ID NO: 30 or a fragment thereof or a variant of said amino acid sequence or fragment and a light chain comprising an amino acid sequence represented by SEQ ID NO: 35 or a fragment thereof or a variant of said amino acid sequence or fragment, and/or competes with said CLDN18.2-binding antibody for binding to CLDN18.2. In one embodiment, the antibody having the ability of binding to CLDN18.2 recognizes the same or essentially the same epitope as a CLDN18.2-binding antibody comprising a heavy chain comprising an amino acid sequence represented by SEQ ID NO: 15 or a fragment thereof or a variant of said amino acid sequence or fragment and a light chain comprising an amino acid sequence represented by SEQ ID NO: 20 or a fragment thereof or a variant of said amino acid sequence or fragment, and/or competes with said CLDN18.2-binding antibody for binding to CLDN18.2. An antibody which competes with a second antibody for binding to a target preferably is antagonistic to said second antibody.

In one embodiment, the toxin drug moiety is cell membrane-permeable. In one embodiment, the toxin drug moiety is a cytotoxic or cytostatic agent. In one embodiment, the toxin drug moiety is a maytansinoid or an auristatin. In one embodiment, the maytansinoid is selected from the group consisting of DM1 and DM4. In one embodiment, the auristatin is selected from the group consisting of monomethyl auristatin E (MMAE) and monomethyl auristatin F (MMAF).

In one embodiment, the antibody having the ability of binding to CLDN18.2 is covalently attached to the toxin drug moiety by a linker. In one embodiment, the linker is a cleavable linker. In one embodiment, the linker is cleavable under intracellular conditions. In one embodiment, the linker is hydrolyzable at a pH of less than 5.5. In one embodiment, the linker is cleavable by an intracellular protease. In one embodiment, the linker is a cathepsin-cleavable linker. In one embodiment, the linker comprises a dipeptide. In one embodiment, the dipeptide is val-cit or phe-lys. In one embodiment, the antibody is attached to the linker through a cysteine thiol of the antibody. In one embodiment, the antibody is attached to the linker through amine groups, in particular amine groups of lysine residues of the antibody.

In one embodiment, the antibody-drug conjugate is administered in an amount effective for the treatment or prevention of the CLDN18.2-expressing cancer. In one embodiment, the antibody-drug conjugate is administered at a dose of between 3 to 30 mg/kg body weight, such as between 4 to 25, 5 to 20, 10 to 18, or 15 to 16 mg/kg body weight. In one embodiment, the antibody-drug conjugate is administered at a dose of between 8 to 150, 9 to 100 or 9 to 90 mg/m$^2$ body surface of a human patient, such as between 12 to 75, 15 to 60, 30 to 54, or 45 to 48 mg/m$^2$ body surface of a human patient. In one embodiment, a single dose of the antibody-drug conjugate or two or more doses of the antibody-drug conjugate are administered. In one embodiment, the antibody-drug conjugate is administered by intravenous injection.

In one embodiment, the method of the invention further comprises administering surgery, chemotherapy and/or radiation therapy.

In one embodiment, expression of CLDN18.2 is at the cell surface of cancer cells. In one embodiment, the cancer is an adenocarcinoma, in particular an advanced adenocarcinoma. In one embodiment, the cancer is selected from the group consisting of gastric cancer, esophageal cancer, pancreatic cancer, lung cancer such as non small cell lung cancer (NSCLC), breast cancer, ovarian cancer, colon cancer, hepatic cancer, head-neck cancer, cancer of the gallbladder and the metastasis thereof, a Krukenberg tumor, peritoneal metastasis and/or lymph node metastasis. In one embodiment, the cancer is selected from the group consisting of cancer of the stomach, cancer of the esophagus, in particular the lower esophagus, cancer of the eso-gastric junction and gastroesophageal cancer. In one embodiment, the patient is a HER2/neu negative patient or a patient with HER2/neu positive status but not eligible to trastuzumab therapy.

In one embodiment, CLDN18.2 has the amino acid sequence according to SEQ ID NO: 1.

In a further aspect, the present invention provides an antibody-drug conjugate comprising an antibody having the ability of binding to CLDN18.2 covalently attached to at least one toxin drug moiety.

In one embodiment, the antibody-drug conjugate is internalized into cells following binding to CLDN18.2 expressed by the cells.

In one embodiment, the antibody having the ability of binding to CLDN18.2 specifically binds to CLDN18.2. In one embodiment, the antibody-drug conjugate specifically binds to CLDN18.2.

In one embodiment, the antibody having the ability of binding to CLDN18.2 is a monoclonal, chimeric or humanized antibody, or a fragment of an antibody. In one embodiment, the antibody having the ability of binding to CLDN18.2 is a monoclonal antibody.

In one embodiment, the antibody having the ability of binding to CLDN18.2 binds to native epitopes of CLDN18.2 present on the surface of living cells. In one embodiment, the antibody having the ability of binding to CLDN18.2 binds to an extracellular domain of CLDN18.2. In one embodiment, the antibody having the ability of binding to CLDN18.2 binds to the first extracellular loop of CLDN18.2.

In one embodiment, the antibody having the ability of binding to CLDN18.2 is an antibody selected from the group consisting of (i) an antibody produced by and/or obtainable from a clone deposited under the accession no. DSM ACC2737, DSM ACC2738, DSM ACC2739, DSM ACC2740, DSM ACC2741, DSM ACC2742, DSM ACC2743, DSM ACC2745, DSM ACC2746, DSM ACC2747, DSM ACC2748, DSM ACC2808, DSM ACC2809, or DSM ACC2810, (ii) an antibody which is a chimerized or humanized form of the antibody under (i), (iii) an antibody having the specificity of the antibody under (i) and (iv) an antibody comprising the antigen binding portion or antigen binding site, in particular the variable region, of the antibody under (i) and preferably having the specificity of the antibody under (i). In one embodiment, the antibody having the ability of binding to CLDN18.2 comprises a heavy chain comprising an amino acid sequence represented by SEQ ID NO: 32 or a fragment thereof or a variant of said amino acid sequence or fragment and a light chain comprising an amino acid sequence represented by SEQ ID NO: 39 or a fragment thereof or a variant of said amino acid sequence or fragment. In one embodiment, the antibody having the ability of binding to CLDN18.2 comprises a heavy chain comprising an amino acid sequence represented by SEQ ID NO: 17 or 51 or a fragment thereof or a variant of said amino acid sequence or fragment and a light chain comprising an amino acid sequence represented by SEQ ID NO: 24 or a fragment thereof or a variant of said amino acid sequence or fragment. In one embodiment, the antibody having the ability of binding to CLDN18.2 comprises a heavy chain comprising an amino acid sequence represented by SEQ ID NO: 30 or a fragment thereof or a variant of said amino acid sequence or fragment and a light chain comprising an amino acid sequence represented by SEQ ID NO: 35 or a fragment thereof or a variant of said amino acid sequence or fragment. In one embodiment, the antibody having the ability of binding to CLDN18.2 comprises a heavy chain comprising an amino acid sequence represented by SEQ ID NO: 15 or a fragment thereof or a variant of said amino acid sequence or fragment and a light chain comprising an amino acid sequence represented by SEQ ID NO: 20 or a fragment thereof or a variant of said amino acid sequence or fragment. In one embodiment, the antibody having the ability of binding to CLDN18.2 recognizes the same or essentially the same epitope as a CLDN18.2-binding antibody comprising a heavy chain comprising an amino acid sequence represented by SEQ ID NO: 32 or a fragment thereof or a variant of said amino acid sequence or fragment and a light chain comprising an amino acid sequence represented by SEQ ID NO: 39 or a fragment thereof or a variant of said amino acid sequence or fragment, and/or competes with said CLDN18.2-binding antibody for binding to CLDN18.2. In one embodiment, the antibody having the ability of binding to CLDN18.2 recognizes the same or essentially the same epitope as a CLDN18.2-binding antibody comprising a heavy chain comprising an amino acid sequence represented by SEQ ID NO: 17 or 51 or a fragment thereof or a variant of said amino acid sequence or fragment and a light chain comprising an amino acid sequence represented by SEQ ID NO: 24 or a fragment thereof or a variant of said amino acid sequence or fragment, and/or competes with said CLDN18.2-binding antibody for binding to CLDN18.2. In one embodiment, the antibody having the ability of binding to CLDN18.2 recognizes the same or essentially the same epitope as a CLDN18.2-binding antibody comprising a heavy chain comprising an amino acid sequence represented by SEQ ID NO: 30 or a fragment thereof or a variant of said amino acid sequence or fragment and a light chain comprising an amino acid sequence represented by SEQ ID NO: 35 or a fragment thereof or a variant of said amino acid sequence or fragment, and/or competes with said CLDN18.2-binding antibody for binding to CLDN18.2. In one embodiment, the antibody having the ability of binding to CLDN18.2 recognizes the same or essentially the same epitope as a CLDN18.2-binding antibody comprising a heavy chain comprising an amino acid sequence represented by SEQ ID NO: 15 or a fragment thereof or a variant of said amino acid sequence or fragment and a light chain comprising an amino acid sequence represented by SEQ ID NO: 20 or a fragment thereof or a variant of said amino acid sequence or fragment, and/or competes with said CLDN18.2-binding antibody for binding to CLDN18.2. An antibody which competes with a second antibody for binding to a target preferably is antagonistic to said second antibody.

In one embodiment, the toxin drug moiety is cell membrane-permeable. In one embodiment, the toxin drug moiety is a cytotoxic or cytostatic agent. In one embodiment, the toxin drug moiety is a maytansinoid or an auristatin. In one embodiment, the maytansinoid is selected from the group consisting of DM1 and DM4. In one embodiment, the auristatin is selected from the group consisting of monomethyl auristatin E (MMAE) and monomethyl auristatin F (MMAF).

In one embodiment, the antibody having the ability of binding to CLDN18.2 is covalently attached to the toxin drug moiety by a linker. In one embodiment, the linker is a cleavable linker. In one embodiment, the linker is cleavable under intracellular conditions. In one embodiment, the linker is hydrolyzable at a pH of less than 5.5. In one embodiment, the linker is cleavable by an intracellular protease. In one embodiment, the linker is a cathepsin-cleavable linker. In one embodiment, the linker comprises a dipeptide. In one embodiment, the dipeptide is val-cit or phe-lys. In one embodiment, the antibody is attached to the linker through a cysteine thiol of the antibody. In one embodiment, the antibody is attached to the linker through amine groups, in particular amine groups of lysine residues of the antibody.

In one embodiment, CLDN18.2 has the amino acid sequence according to SEQ ID NO: 1.

In a further aspect, the present invention provides a pharmaceutical formulation comprising the antibody-drug conjugate of the invention, and a pharmaceutically acceptable diluent, carrier or excipient.

In a further aspect, the present invention provides a medical preparation comprising the antibody-drug conjugate of the invention. In one embodiment, the medical preparation is present in the form of a kit comprising a container including the antibody-drug conjugate. In one embodiment, the medical preparation further includes printed instructions for use of the preparation in a method of treating or preventing cancer, in particular a CLDN18.2-expressing cancer.

In a further aspect, the present invention provides the antibody-drug conjugate of the invention, the pharmaceutical composition of the invention or the medical preparation of the invention for use in therapy, in particular for use in a method of treating or preventing cancer, in particular a CLDN18.2-expressing cancer. In one embodiment, the method of treating or preventing cancer is a method of treating or preventing a CLDN18.2-expressing cancer of the invention.

Other features and advantages of the instant invention will be apparent from the following detailed description and claims.

HEK293~CLDN18.2 cells were incubated for 72 h with anti-CLDN18.2 specific antibodies and saporin conjugated anti-human IgG Fab fragment (Fab-ZAP human). Endocytosis of IMAB362, chim mAB294, chim mAB308 and chim mAB359 was determined indirectly by measuring cell viability. Data points (n=3 replicates) are depicted as mean±SD.

Figure 3:
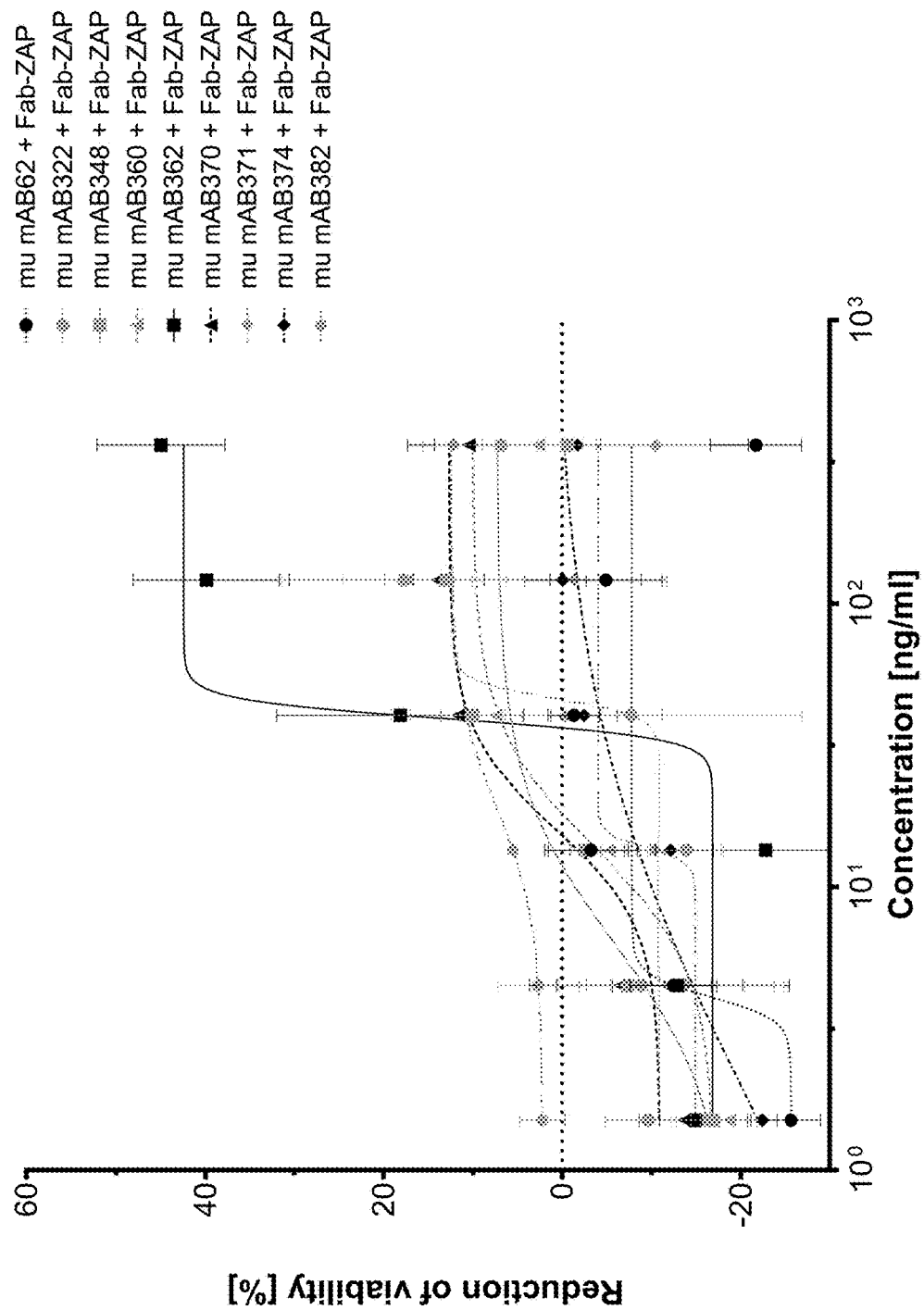

FIG. 3: Reduction of viability after co-incubation of HEK293~CLDN18.2 cells with murine anti-CLDN18.2 antibodies and Fab-ZAP (indirect evaluation of internalization).

HEK293~CLDN18.2 cells were incubated for 72 h with anti-CLDN18.2 reactive murine antibodies and saporin conjugated anti-mouse IgG Fab fragment (Fab-ZAP murine). Endocytosis of different anti-CLDN18.2 reactive murine antibodies was indirectly determined by measuring cell viability.

FIG. 4A-4D: Relative binding affinities of IMAB362-DM4 and IMAB362-vcMMAE to CLDN18.2 positive cells.

Relative binding affinities of IMAB362-toxin conjugates in comparison to unconjugated IMAB362 were determined on (FIG. 4A) NUGC-4 10cF7-5 sort3a and (FIG. 4B) DAN-G 1C5F2 cells endogenously expressing CLDN18.2, (FIG. 4C) NCI-N87~CLDN18.2 and (FIG. 4D) BxPC-3~CLDN18.2 cells ectopically overexpressing CLDN18.2 by flow cytometry at antibody concentrations up to 20 µg/ml. Data points (n=2 replicates) are depicted as mean±SD.

FIG. 5A-5B: CLDN18.2-mediated binding of IMAB362-DM4 and IMAB362-vcMMAE.

CLDN18.2-mediated binding of IMAB362-toxin conjugates was analyzed on (FIG. 5A) NCI-N87~CLDN18.2 cells ectopically overexpressing CLDN18.2 and on (FIG. 5B) the corresponding CLDN18.2 negative human tumor cell line by flow cytometry at antibody concentrations up to 20 µg/ml. Data points (n=2 replicates) are depicted as mean±SD.

FIG. 6A-6C: Binding specificities of IMAB362-DM4 and IMAB362-vcMMAE.

Binding specificities of IMAB362-toxin conjugates were determined on (FIG. 6A) HEK293~CLDN18.2, (FIG. 6B) HEK293~CLDN18.1 or (FIG. 6C) HEK293~mock cells as negative control. Binding was analyzed by flow cytometry at antibody concentrations up to 20 µg/ml. Data points (n=2 replicates) are depicted as mean±SD.

Figure 7A:
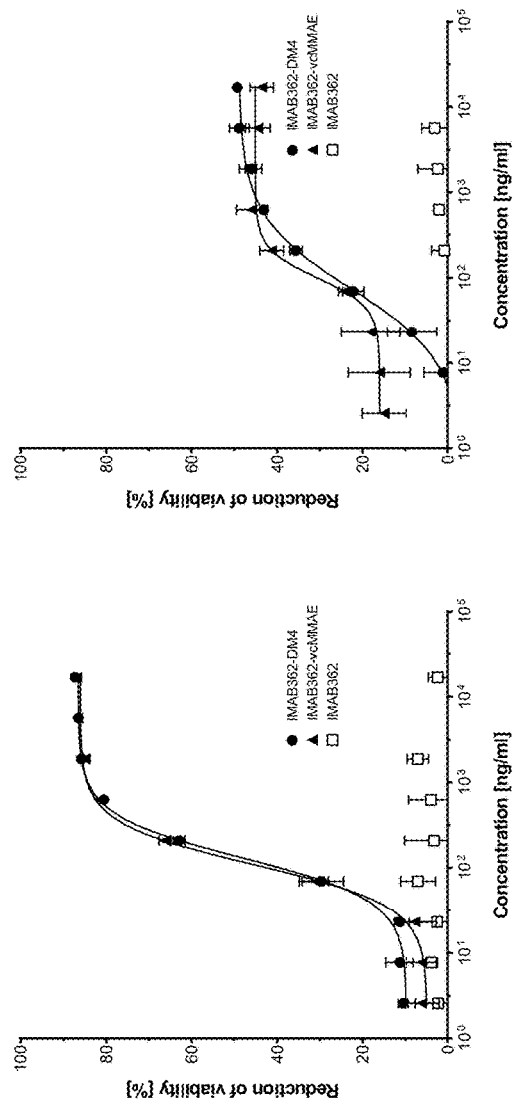
Figure 7B:
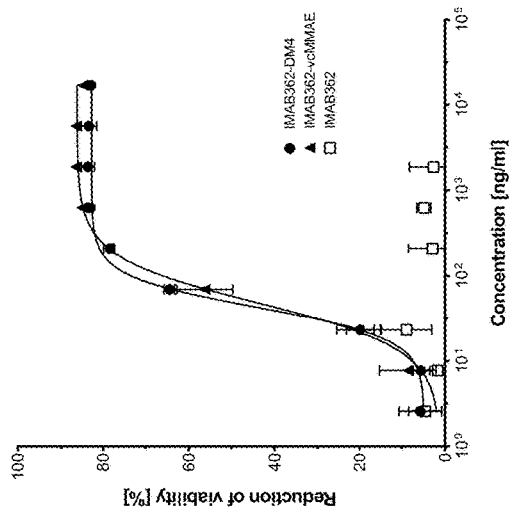
Figure 7C:
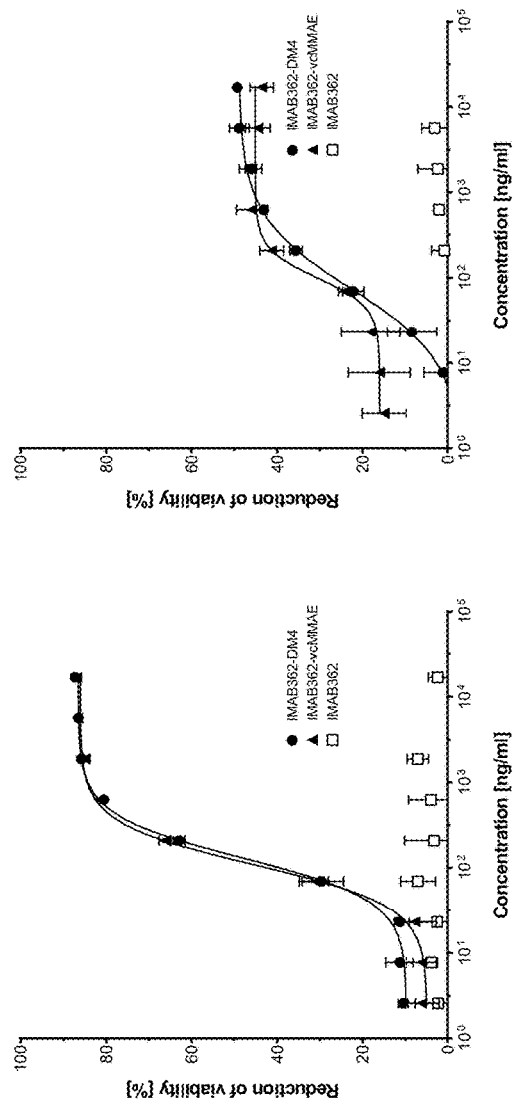

FIG. 7A-7C: Effect of IMAB362-DM4 and IMAB362-vcMMAE on viability of CLDN18.2 expressing human carcinoma cell lines.

Dose-response curves of IMAB362-DM4- and IMAB362-vcMMAE-mediated reduction of (FIG. 7A) NUGC-4 10cF7-5 sort 3a, (FIG. 7B) NCI-N87~CLDN18.2 and (FIG. 7C) BxPC-3~CLDN18.2 cell viability. IMAB362 was used as a negative control (no effect in viability assays under these conditions). Cells were incubated for 72 h in the presence of antibody at concentrations up to 16875 ng/ml. The reduction of cell viability was measured using a XTT-based viability assay. Data points (n=3 replicates) are depicted as mean±SD.

Figure 8:
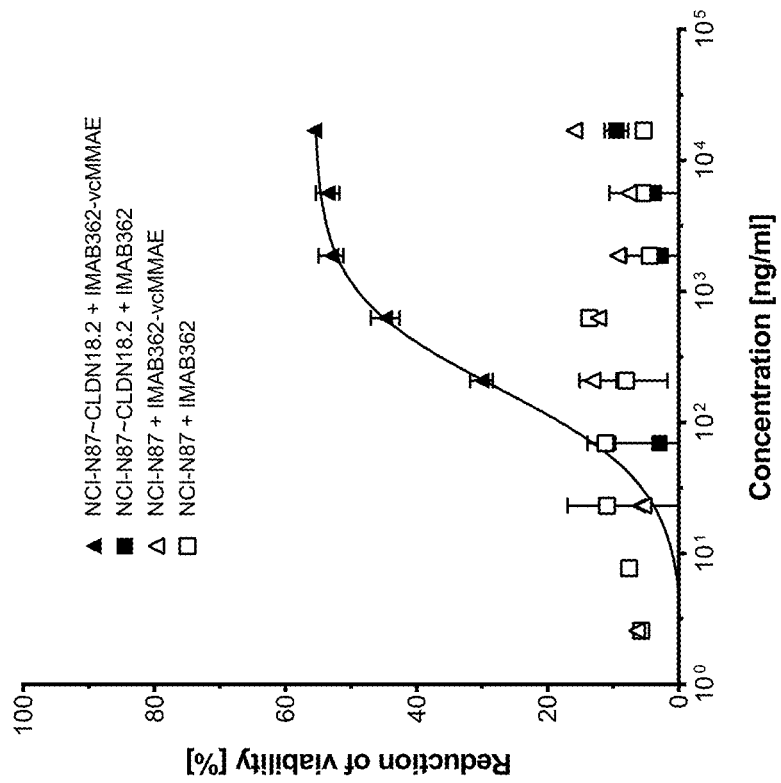

FIG. 8: CLDN18.2 dependency of IMAB362-vcMMAE mediated reduction of tumor cell viability.

Target dependency of IMAB362-vcMMAE-mediated reduction of cell viability was determined on NCI-N87 cells (CLDN18.2 negative) and NCI-N87~CLDN18.2 cells ectopically expressing the target. The cells were incubated for 72 h with IMAB362-vcMMAE or unconjugated IMAB362 at concentrations up to 16875 ng/ml. IMAB362 is known to have no activity under the experimental conditions used here. The reduction of cell viability was measured using a XTT-based viability assay. Data points (n=3 replicates) are depicted as mean±SD.

Figure 9:
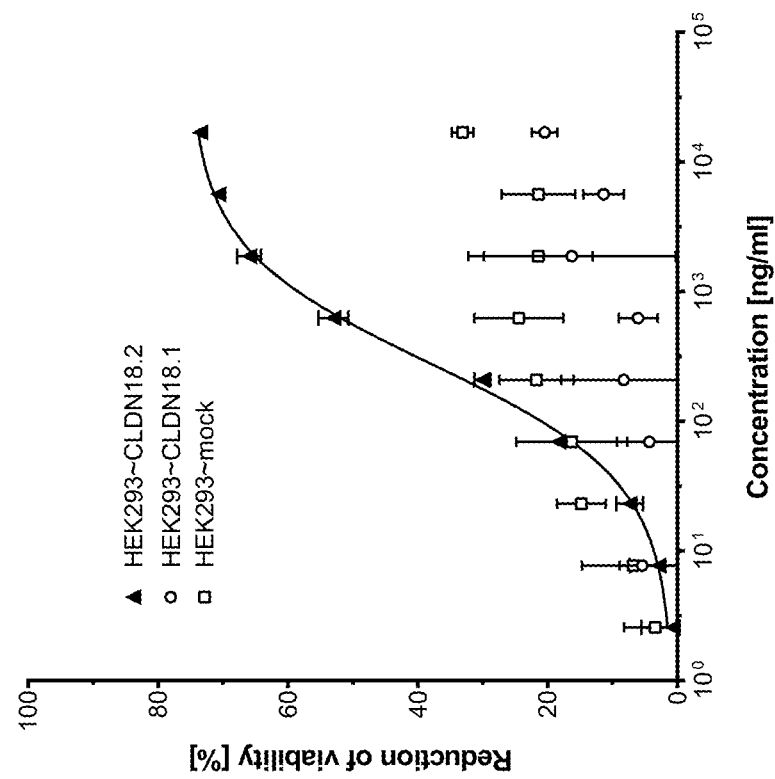

FIG. 9: Specificity of IMAB362-vcMMAE mediated reduction of cell viability.

Target specificity of IMAB362-vcMMAE-mediated reduction of cell viability was tested with stably transfected HEK293~CLDN18.2, HEK293~CLDN18.1 and HEK293~mock cells. Cells were incubated for 72 h in the presence of IMAB362-vcMMAEat concentrations up to 16875 ng/ml. The reduction of cell viability was measured using a XTT-based viability assay. Data points (n=3 replicates) are depicted as mean±SD.

Figure 10:
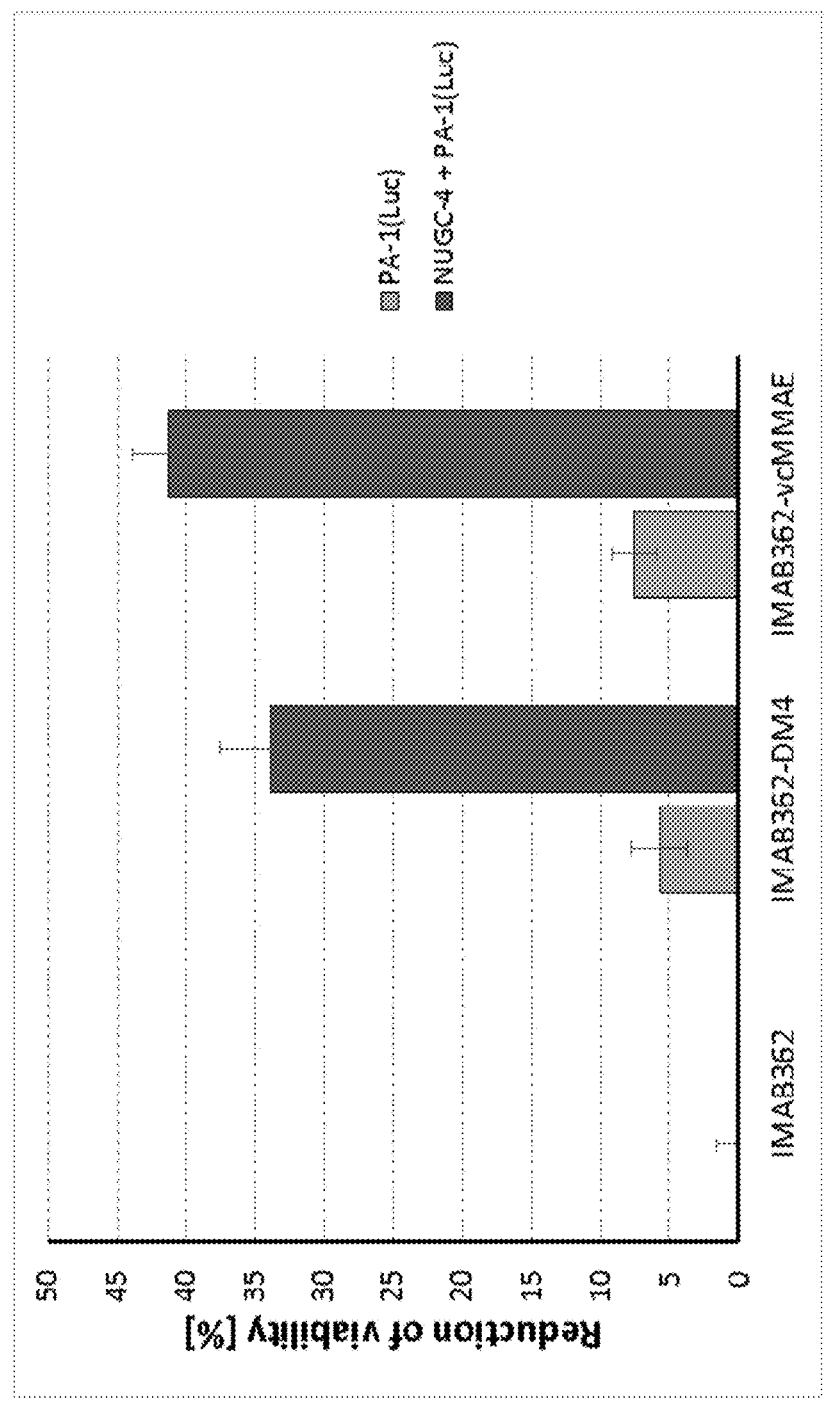

FIG. 10: Bystander activities of IMAB362-DM4 and IMAB362-vcMMAE.

IMAB362-DM4- and IMAB362-vcMMAE-mediated induction of bystander effects were determined in co-culture experiments using PA-1 (Luc) cells (CLDN18.2 negative/luciferase positive) and NUGC-4 10cE8 cells (CLDN18.2 positive/luciferase negative). As background control PA-1 (Luc) cells were incubated with either IMAB362-DM4- or IMAB362-vcMMAE. For treatment, cells were cultivated for 4 days in the presence of 200 ng/ml IMAB362-DM4, 800 ng/ml IMAB362-vcMMAE or 800 ng/ml IMAB362. Luciferase activity was measured.

Figure 11:
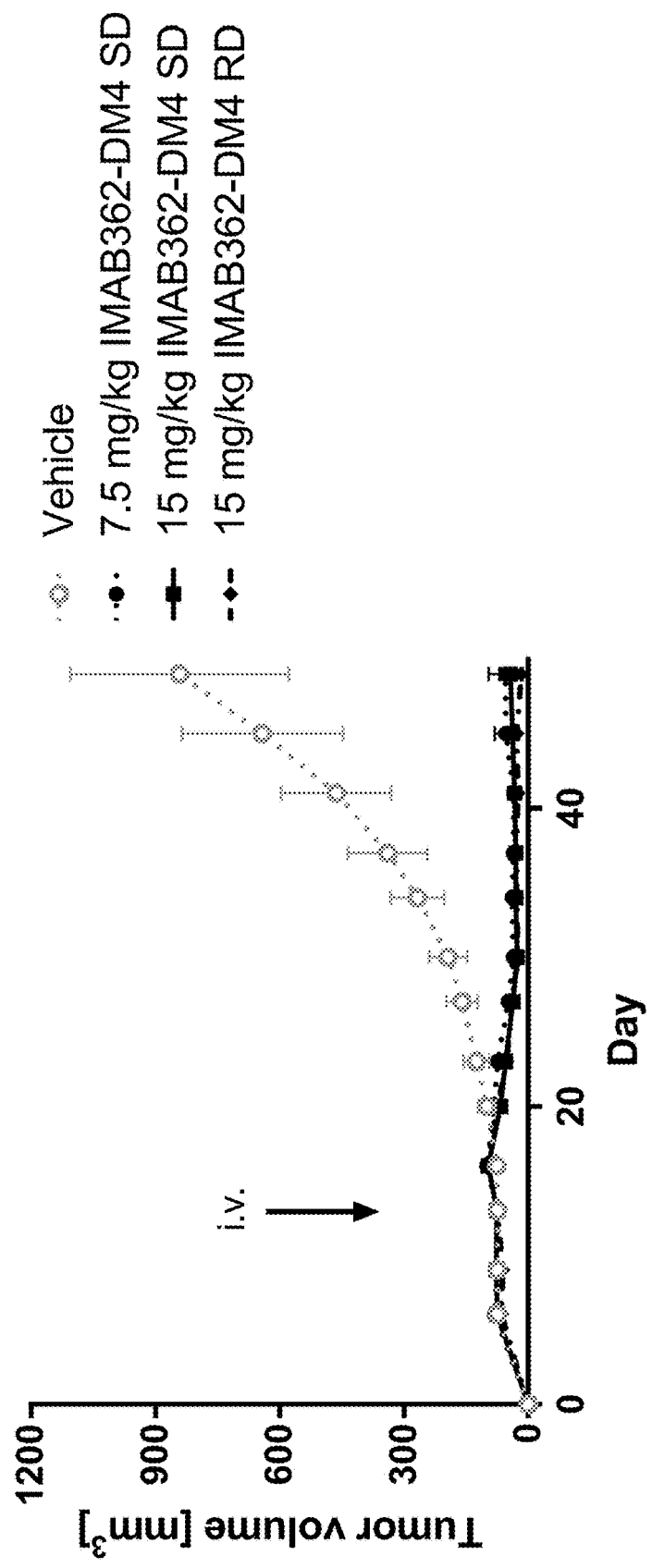

FIG. 11: Tumor growth inhibition of advanced BxPC-3~CLDN18.2 xenograft tumors by IMAB362-DM4.

CLDN18.2-positive BxPC-3~CLDN18.2 cells were engrafted subcutaneously in the flank of female athymic nude mice. On day 14, mice were organized in 4 groups and injected intravenously with a single dose of vehicle, 7.5 mg/kg, 15 mg/kg IMAB362-DM4 or a repeated dose of 15 mg/kg IMAB362-DM4 (day 14 and 21). The size of subcutaneous tumors was measured twice weekly (mean+SEM). Group size n=5. SD: single dose, RD: repeated dose.

Figure 12:
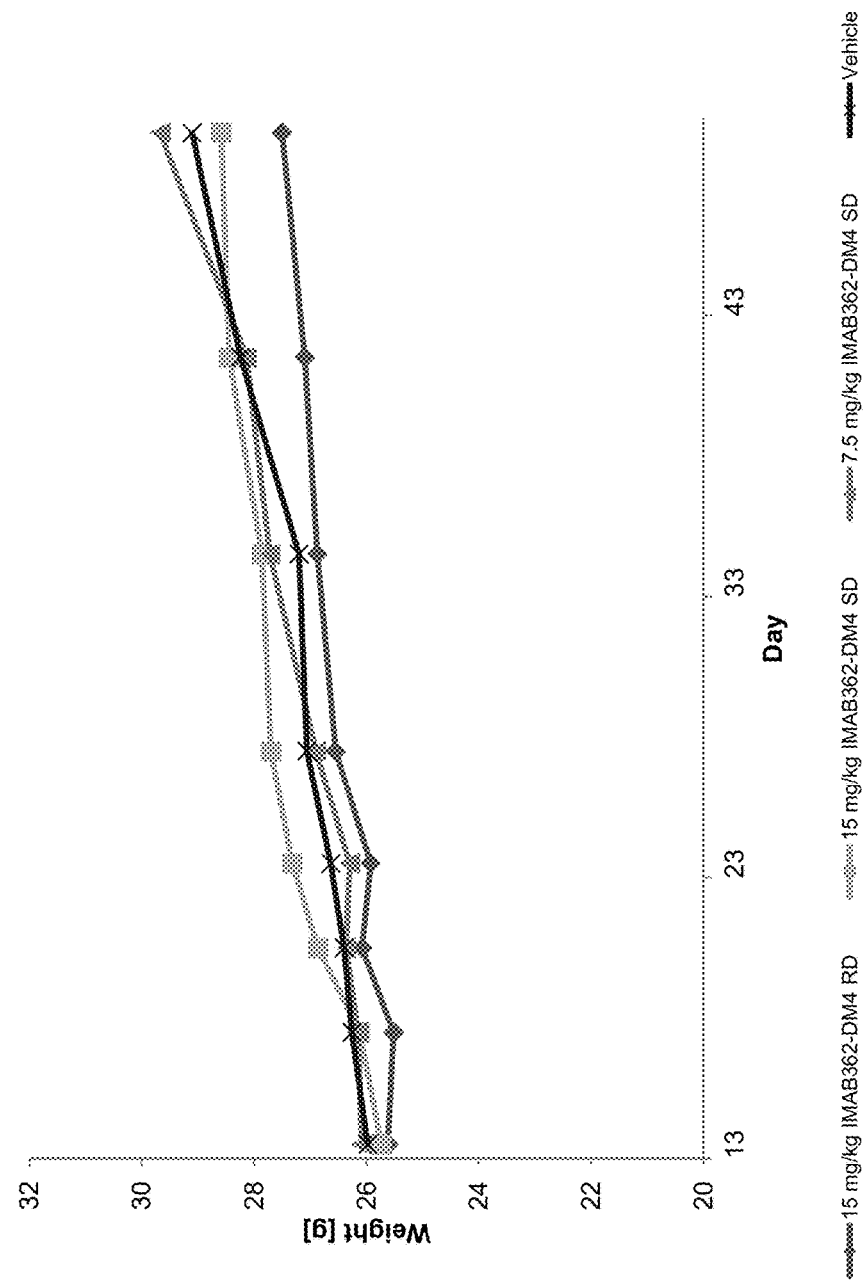
Figure 14A:
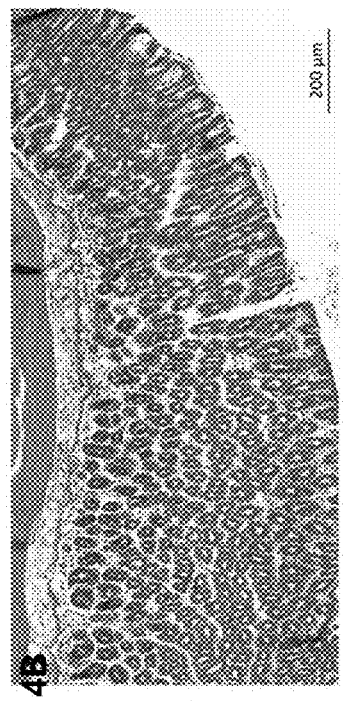
Figure 14B:
Figure 14C:
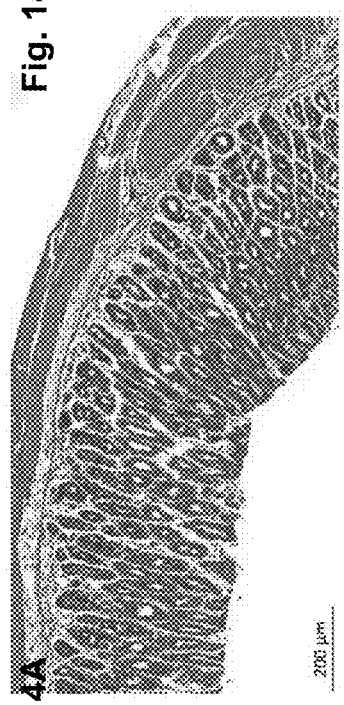
Figure 14D:
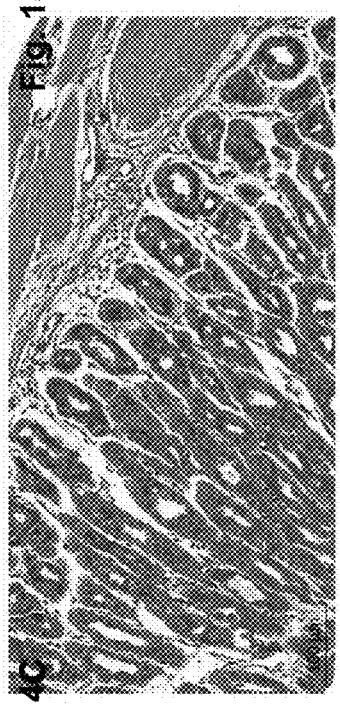

FIG. 12: Mean body weight of mice treated with IMAB362-DM4.

The body weight of BxPC-3~CLDN18.2 tumor bearing nude mice treated with a single dose of vehicle control, 7.5 mg/kg or 15 mg/kg or repeated doses of 15 mg/kg IMAB362-DM4, respectively, was monitored twice a week. The body weight of the 4 groups is presented as mean. Group size n=5.

FIG. 13A-13M: Clinical chemistry parameters from the single and repeated dose administration of IMAB362-DM4 in xenograft nude mice.

Clinical chemistry of BxPC-3~CLDN18.2-tumor bearing female nude mice treated intravenously with a single dose of vehicle, 7.5 mg/kg, 15 mg/kg IMAB362-DM4 or a repeated dose of 15 mg/kg IMAB362-DM4 was analyzed on day 49 after engraftment. 13A) Alanine transaminase (GPT), 13B) aspartate transaminase (GOT), 13C) glutamate dehydrogenase, 13D) alkaline phosphatase, 13E) α-amylase, 13F) cholinesterase, 13G) creatine kinase (CK), 13H) lactate dehydrogenase (LDH), 13I) lipase, 13J) urea, 13K) glucose, 13L) total protein and 13M) albumin.

FIG. 14A-14D: Histological analysis of stomach sections from IMAB362-DM4 and vehicle treated mice.

Mice bearing BxPC-3~CLDN18.2 xenograft tumors were treated with IMAB362-DM4. On day 49 post-graft mice were sacrificed and selected organs dissected and formalin fixed. Sections of these FFPE tissue were stained with hematoxylin-eosin and examined microscopically for morphological alterations. (FIG. 14A, 14C) Stomach tissues of a representative mouse from the treatment group with the highest IMAB362-DM4 exposure (15 mg/kg IMAB362-DM4 on day 14 and day 21 post-graft). (FIG. 14B, 14D) Stomach tissue of mouse of the control group treated with the vehicle only. Magnification: see scale bar.

Figure 15:
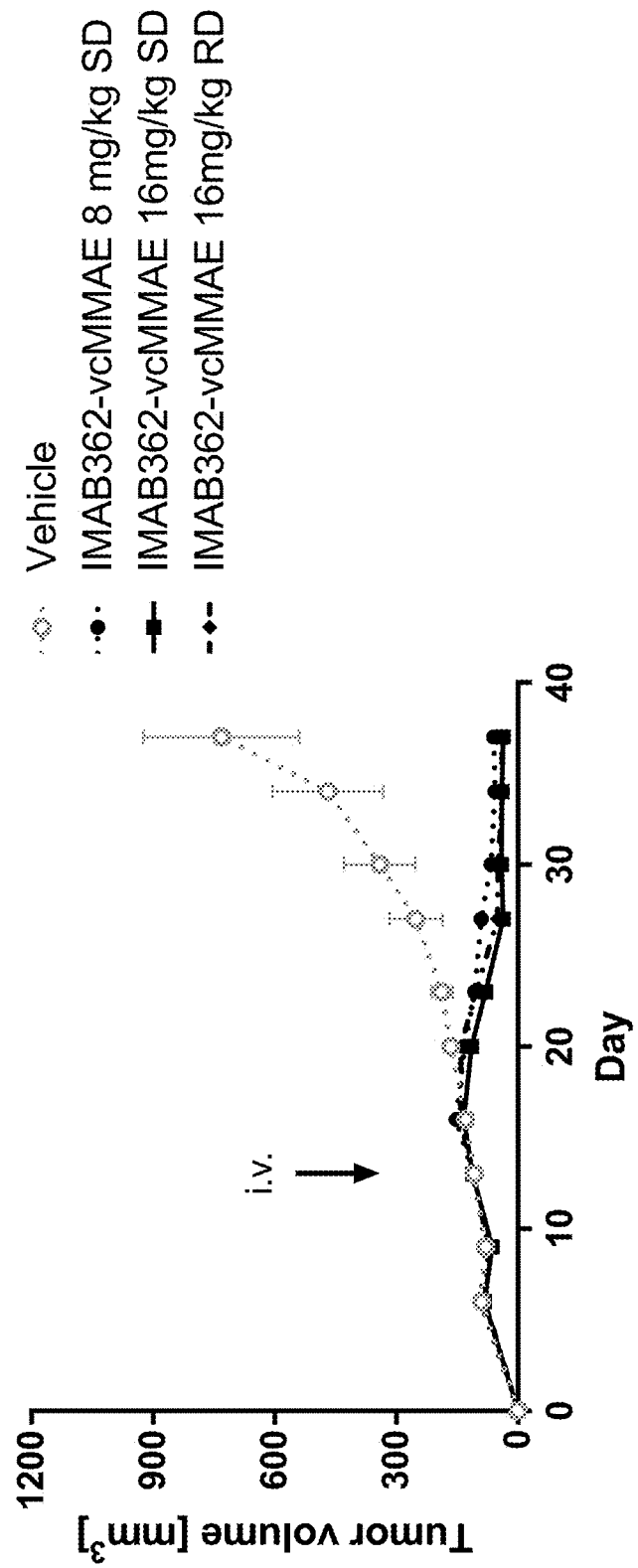

FIG. 15: Tumor growth inhibition of advanced BxPC-3~CLDN18.2 xenograft tumors IMAB362-vcMMAE.

CLDN18.2-positive BxPC-3~CLDN18.2 cells were engrafted subcutaneously into the flank of female nude mice. On day 14, mice were organized in 4 groups and injected intravenously with a single dose of vehicle, 8 mg/kg, 16 mg/kg IMAB362-vcMMAE or a repeated dose of 16 mg/kg IMAB362-vcMMAE (day 14 and 21). The size of subcutaneous tumors was measured twice a week (mean+SEM). Group size n=5.

Figure 16:
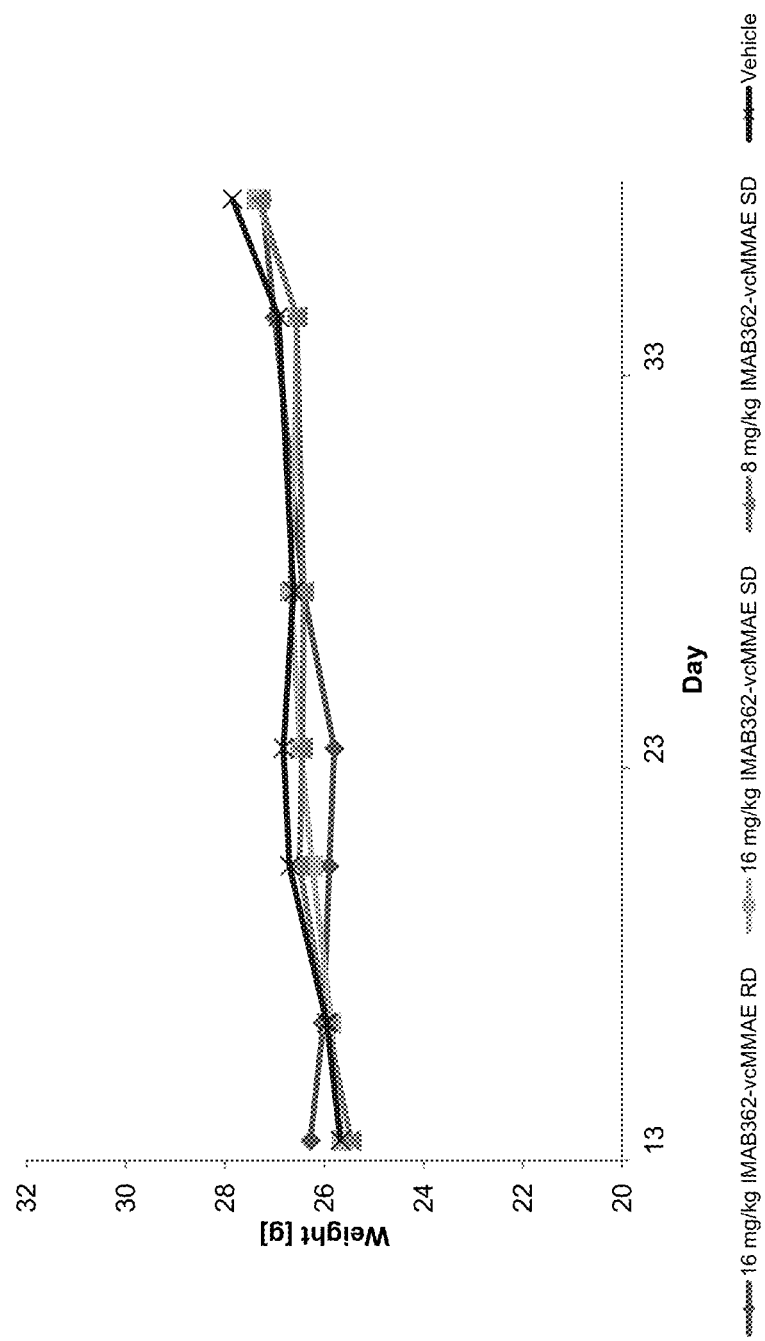

FIG. 16: Mean body weight of mice treated with IMAB362-vcMMAE.

The body weight of tumor bearing female nude mice treated with a single dose of vehicle control, 8 mg/kg or 16 mg/kg, or repeated doses of 16 mg/kg IMAB362-vcMMAE was monitored twice a week. The body weight of the 4 groups is presented as mean. Group size n=5.

FIG. 17A-17M: Clinical chemistry parameters from the single and repeated dose administration of IMAB362-vcMMAE in xenograft nude mice.

Clinical chemistry of BxPC-3~CLDN18.2-tumor bearing female nude mice intravenously treated with a single dose of vehicle, 8 mg/kg, 16 mg/kg IMAB362-vcMMAE or a repeated dose of 16 mg/kg IMAB362-vcMMAE was analyzed on day 37 after engraftment. 17A) Alanine transaminase (GPT), 17B) aspartate transaminase (GOT), 17C) glutamate dehydrogenase, 17D) alkaline phosphatase, 17E) α-amylase, 17F) cholinesterase, 17G) creatine kinase (CK), 17H) lactate dehydrogenase (LDH), 17I) lipase, 17J) urea, 17K) glucose, 17L) total protein and 17M) albumin.

FIG. 18A-18L: Dose-dependent anti-tumoral efficacy of IMAB362-DM4 and IMAB362-vcMMAE in an advanced human NCI-N87~CLDN18.2 gastric xenograft tumor model.

NCI-N87~CLDN18.2 cells ectopically expressing human CLDN18.2 were engrafted subcutaneously into the flank of female nude mice. On day 10 post engraftment, mice were organized into groups and injected intravenously with a single dose of vehicle, 3.8, 7.6 or 15.2 mg/kg IMAB362-DM4 or 4, 8 or 16 mg/kg IMAB362-vcMMAE on day 13. Another control group received repeated doses of ~8 mg/kg IMAB362 twice a week by alternating IV and i.p. injections. Tumor volumes were measured two times a week. Animals were sacrificed when the tumor volume exceeded 1400 mm³ or when the tumors ulcerated. Statistical analysis of tumor growth was performed using Kruskal-Wallis and post-hoc Dunn Test. Survival was analyzed using Mantel Cox Test comparing the vehicle control group with IMAB362-DM4 and IMAB362-vcMMAE, respectively. (FIG. 18A-18H) Tumor growth curves, (FIG. 18I, 18K) mean tumor growth (±SEM) and (FIG. 18J, 18L) survival plots of mice treated with vehicle control, IMAB362 or IMAB362-DM4 or IMAB362-vcMMAE. Group size: n=11; *: $p<0.05$; ***$p<0.001$. The arrow indicates the start of treatment.

FIG. 19A-19F: Anti-tumoral efficacy of IMAB362-DM4 and IMAB362-vcMMAE in an early human NUGC-4 10cF7-5 sort3a gastric xenograft tumor model.

NUGC-4 10cF7-5 sort3a cells endogenously expressing CLDN18.2 were engrafted subcutaneously into the flank of female nude mice. On day 3, mice received vehicle, 15.2 mg/kg IMAB362-DM4 or 16 mg/kg IMAB362-vcMMAE by a single IV injection. Tumor volumes were measured twice a week. Animals were sacrificed when the tumor volume exceeded 1400 mm³ or when the tumors ulcerated or after the pre-defined observation period of 120 days. Statistical analysis of tumor growth was performed using Kruskal-Wallis and post-hoc Dunn Test. Survival was analyzed using Mantel Cox Test. (FIG. 19A-19C) Tumor growth curves, (FIG. 19D) mean tumor growth (±SEM) and (FIG. 19E, 19F) survival plots of mice treated with vehicle control, IMAB362-DM4 or IMAB362-vcMMAE. Group size: n=10; *: $p<0.001$; **: $p<0.0001$. The arrow indicates the time point of treatment.

FIG. 20A-20L: Dose-dependent anti-tumoral efficacy of IMAB362-DM4 and IMAB362-vcMMAE in an advanced human BxPC-3~CLDN18.2 pancreatic xenograft tumor model.

BxPC-3~CLDN18.2 cells ectopically expressing human CLDN18.2 were engrafted subcutaneously into the flank of female nude mice. On day 13, mice were organized into groups and injected intravenously with a single dose of vehicle, 3.8, 7.6 or 15.2 mg/kg IMAB362-DM4 or 4, 8 or 16 mg/kg IMAB362-vcMMAE on day 14. Mice from the antibody control group received ~8 mg/kg unconjugated IMAB362 two times a week by alternating IV and i.p. injections. Tumor size was measured twice a week. Animals were sacrificed when the tumor volume exceeded 1400 mm³ or when the tumors ulcerated. Statistical analysis of tumor growth was performed using Kruskal-Wallis and post-hoc Dunn Test. Survival was analysed using Mantel Cox Test comparing the vehicle control group with IMAB362-DM4 and IMAB362-vcMMAE, respectively. (FIG. 20A-20H) Tumor growth curves (FIG. 20I, 20K) mean tumor growth (±SEM) and (FIG. 20J, 20L) survival plots of mice treated with vehicle control, IMAB362, IMAB362-DM4 or IMAB362-vcMMAE. Group size: n=11; $p<0.05$; : $p<0.01$; *: $p<0.001$; ****: $p<0.0001$. The arrow indicates the time point of treatment.

FIG. 21A-21-F: Anti-tumoral efficacy of IMAB362-DM4 and IMAB362-vcMMAE in an early human DAN-G 1C5F2 pancreatic xenograft tumor model.

DAN-G 1C5F2 cells endogenously expressing CLDN18.2 were engrafted subcutaneously into the flank of female nude mice. On day 3 post engraftment, mice were treated with a single IV injection of vehicle control, 15.2 mg/kg IMAB362-DM4 or 16 mg/kg IMAB362-vcMMAE. Tumor volumes were measured twice a week. Animals were sacrificed when the mice lost more than 10% body weight due to cancer cachexia, when the tumors ulcerated or after the pre-defined observation period of 120 days. Statistical analysis of tumor growth was performed using Kruskal-Wallis and post-hoc Dunn Test. Survival was analyzed using Mantel Cox Test. (FIG. 21A-21C) Tumor growth curves (FIG. 21D) mean tumor growth (±SEM) and (FIG. 21E, 21F) survival plots of mice treated with vehicle control, IMAB362-DM4 or IMAB362-vcMMAE. Group size: n=10; : $p<0.01$; *: $p<0.001$. The arrow indicates the time point of treatment.

FIG. 22A-22D: Histological analysis of stomach sections from IMAB362-vcMMAE and vehicle treated mice.

Mice bearing BxPC-3~CLDN18.2 xenograft tumors were treated with IMAB362-vcMMAE. On day 37 post-graft mice were sacrificed and selected organs dissected and formalin fixed. Sections of these FFPE tissues were stained with hematoxylin-eosin and examined microscopically for morphological alterations. (FIG. 22A, 22C) Stomach tissue of a representative mouse from the treatment group with the highest IMAB362-vcMMAE exposure (16 mg/kg IMAB362-vcMMAE on day 14 and day 21 post-graft). (FIG. 22B, 22D) Stomach tissue of a mouse of the control group treated with the vehicle only. Magnification: see scale bar.

FIG. 23A-23B: Induction of apoptosis by IMAB362-DM4 and IMAB362-vcMMAE.

IMAB362-DM4- and IMAB362-vcMMAE-mediated induction of apoptosis was determined by measuring caspase 3/7 activity and staining with annexin V using target positive NUGC-4 10cE8 cells. FIG. 23A) Caspase 3/7 activity was analyzed after the cells were incubated for 3 days in the presence of 2.5 µg/ml IMAB362 antibodies (n=3 replicates, mean±SD). FIG. 23B) Flow cytometric analysis of cells co-stained with annexin V and propidium iodide (PI) was performed 4 days after treatment with 2.5 µg/ml IMAB362 antibodies (n=3 replicates). Untreated cells served as control.

FIG. 24A-24F: Anti-tumoral efficacy of IMAB362-DM4 and IMAB362-vcMMAE in an advanced human NUGC-4 10cF7-5 sort3a gastric xenograft tumor model.

NUGC-4 10cF7-5 sort3a cells endogenously expressing CLDN18.2 were engrafted subcutaneously into the flank of female nude mice. On day 10, mice received vehicle, 15.2 mg/kg IMAB362-DM4 or 16 mg/kg IMAB362-vcMMAE by a single IV injection. Tumor volumes were measured twice a week. Animals were sacrificed when the tumor volume exceeded 1400 mm3, when tumors ulcerated or after the pre-defined observation period of 120 days. Statistical analysis of tumor growth was performed using Kruskal-Wallis and post-hoc Dunn Test. Survival was analyzed using Mantel Cox Test. (FIG. 24A-24C) Tumor growth curves, (FIG. 24D) mean tumor growth (±SEM) and (FIG. 24E, 24F) survival plots of mice treated with vehicle control, IMAB362-DM4 or IMAB362-vcMMAE. Group size: n=10; *: $p<0.05$; ***: $p<0.001$. The arrow indicates the time point of treatment.

FIG. 25A-25B: IMAB362-DM4 and IMAB362-vcMMAE mediated ADCC on CLDN18.2 expressing human cancer cells.

FIG. 25A) Dose response curves of IMAB362-DM4 (solid black circles), IMAB362-vcMMAE (solid black triangles) and IMAB362 (open black squares) mediated ADCC on endogenously CLDN18.2 expressing NUGC-4 10cF7_5 sort3a p3151 #10 human stomach carcinoma cells. Experiments were performed using an effector to target ratio of ~40:1. Data points (n=4 replicates) are depicted as mean±SD. FIG. 25B) Flow cytometric analysis of CLDN18.2 expression on NUGC-4 10cF7_5 sort3a p3151 #10 cells. Gray filled histogram: anti-CLDN18.2 (IMAB362, 50 µg/ml). Black dotted line: Isotype control.

FIG. 26A-26B: IMAB362-DM4 and IMAB362-vcMMAE mediated CDC on CLDN18.2 expressing human cancer cells. FIG. 26A) Dose response curves of IMAB362-DM4 (solid black circles), IMAB362-vcMMAE (solid black triangles) and IMAB362 (open black squares) mediated CDC on endogenously CLDN18.2 expressing KATO-III FGF BP #12 adM p3151 #25 (left) and NUGC-4 10cF7_5 sort3a p3151 #10 human stomach carcinoma cells (right). Luciferase expressing target cells were incubated for 90 min with 20% human serum (pool from healthy human donors) and the respective antibodies at indicated concentrations. Data points (n=3 replicates) are depicted as mean±SD. FIG. 26B) Flow cytometric analyses of CLDN18.2 expression on KATO-III FGF BP #12 adM p3151 #25 (left) and NUGC-4 10cF7_5 sort3a p3151 #10 cells (right). Gray filled histogram: anti-CLDN18.2 (IMAB362, 50 µg/ml). Black dotted line: Isotype control.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop or domain consists on average of 53 amino acids, and the second extracellular loop or domain consists of around 24 amino acids. Cell surface proteins of the claudin family, such as CLDN18.2, are expressed in tumors of various origins, and are particularly suited as target structures in connection with antibody-mediated cancer immunotherapy due to their selective expression (no expression in a toxicity relevant normal tissue) and localization to the plasma membrane.

The term "CLDN" as used herein means claudin and includes CLDN18.2. Preferably, a claudin is a human claudin.

The term "CLDN18" relates to claudin 18 and includes any variants, including claudin 18 splice variant 1 (claudin 18.1 (CLDN18.1)) and claudin 18 splice variant 2 (claudin 18.2 (CLDN18.2)).

The term "CLDN18.2" preferably relates to human CLDN18.2, and, in particular, to a protein comprising, preferably consisting of the amino acid sequence according to SEQ ID NO: 1 of the sequence listing or a variant of said amino acid sequence. The first extracellular loop or domain of CLDN18.2 preferably comprises amino acids 27 to 81, more preferably amino acids 29 to 78 of the amino acid sequence shown in SEQ ID NO: 1. The second extracellular loop or domain of CLDN18.2 preferably comprises amino acids 140 to 180 of the amino acid sequence shown in SEQ ID NO: 1. Said first and second extracellular loops or domains preferably form the extracellular portion or domain of CLDN18.2.

CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

The term "CLDN18.1" preferably relates to human CLDN18.1, and, in particular, to a protein comprising, preferably consisting of the amino acid sequence according to SEQ ID NO: 2 of the sequence listing or a variant of said amino acid sequence.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

According to the invention, the term "CLDN18.2-expressing cancer" or "CLDN18.2-positive cancer" means a cancer involving cancer cells expressing CLDN18.2, preferably on the surface of said cancer cells.

"Cell surface" is used in accordance with its normal meaning in the art, and thus includes the outside of the cell which is accessible to binding by proteins and other molecules.

CLDN18.2 is expressed on the surface of cells if it is located at the surface of said cells and is accessible to binding by CLDN18.2-specific antibodies added to the cells.

The term "extracellular portion" or "extracellular domain" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1,5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cells.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cells. Preferably, CLDN18.2 expressed in a cell is expressed or exposed on the surface of said cell.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes cancer, in particular those forms of cancer described herein. Any reference herein to cancer or particular forms of cancer also includes cancer metastasis thereof. In a preferred embodiment, a disease to be treated according to the present application involves cells expressing CLDN18.2.

"Disease involving cells expressing CLDN18.2" or "disease associated with cells expressing CLDN18.2" or similar expressions means according to the invention that CLDN18.2 is expressed in cells of a diseased tissue or organ. In one embodiment, expression of CLDN18.2 in cells of a diseased tissue or organ is increased compared to the state in a corresponding healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a corresponding healthy tissue is repressed. According to the invention, diseases associated with cells expressing CLDN18.2 include cancer diseases. Furthermore, according to the invention, cancer diseases preferably are those wherein the cancer cells express CLDN18.2.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing CLDN18.2 and a cancer cell expresses CLDN18.2. A cell expressing CLDN18.2 preferably is a cancer cell, preferably of the cancers described herein.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant. According to the invention, a "cancer disease" preferably is a "tumor disease". However, generally, the terms "cancer" and "tumor" are used interchangeably herein.

In one embodiment, a cancer according to the invention involves cancer cells expressing CLDN18.2. In one embodiment, the cancer is CLDN18.2 positive. In one embodiment, expression of CLDN18.2 is at the surface of the cells. In one embodiment, at least 50%, preferably 60%, 70%, 80% or 90% of the cancer cells are CLDN18.2 positive and/or at least 40%, preferably at least 50% of the cancer cells are positive for surface expression of CLDN18.2. In one embodiment, at least 95% or at least 98% of the cancer cells are CLDN18.2 positive. In one embodiment, at least 60%, at least 70%, at least 80% or at least 90% of the cancer cells are positive for surface expression of CLDN18.2.

In one embodiment, a CLDN18.2-expressing cancer, a cancer involving cancer cells expressing CLDN18.2 or a CLDN18.2 positive cancer is selected from the group consisting of gastric cancer, esophageal cancer, pancreatic cancer, lung cancer such as non small cell lung cancer (NSCLC), ovarian cancer, colon cancer, hepatic cancer, head-neck cancer, and cancer of the gallbladder and metastases thereof, in particular gastric cancer metastasis such as Krukenberg tumors, peritoneal metastasis and lymph node metastasis. In one embodiment, the cancer is an adenocarcinoma, in particular an advanced adenocarcinoma. Particularly preferred cancer diseases are adenocarcinomas of the stomach, the esophagus, the pancreatic duct, the bile ducts, the lung and the ovary. In one embodiment, the cancer is selected from the group consisting of cancer of the stomach, cancer of the esophagus, in particular the lower esophagus, cancer of the eso-gastric junction and gastroesophageal cancer. In a particularly preferred embodiment, the cancer is gastroesophageal cancer such as metastatic, refractory or recurrent advanced gastroesophageal cancer.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy of the invention is metastasis originating from gastric cancer as primary site. In preferred embodiments such gastric cancer metastasis is Krukenberg tumors, peritoneal metastasis and/or lymph node metastasis.

Krukenberg tumor is an uncommon metastatic tumor of the ovary accounting for 1% to 2% of all ovarian tumors. Prognosis of Krukenberg tumor is still very poor and there is no established treatment for Krukenberg tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported. The interval between the diagnosis of a primary carcinoma and the subsequent discovery of ovarian involvement is usually 6 months or less, but longer periods have been reported. In many cases, the primary tumor is very small and can escape detection. A history of a prior carcinoma of the stomach or another organ can be obtained in only 20% to 30% of the cases.

Patients with Krukenberg tumors have an overall mortality rate that is significantly high. Most patients die within 2 years (median survival, 14 months). Several studies show that the prognosis is poor when the primary tumor is identified after the metastasis to the ovary is discovered, and the prognosis becomes worse if the primary tumor remains covert.

No optimal treatment strategy for Krukenberg tumors has been clearly established in the literature. Whether a surgical resection should be performed has not been adequately addressed. Chemotherapy or radiotherapy has no significant effect on prognosis of patients with Krukenberg tumors.

The term "(therapeutic) treatment", in particular in connection with the treatment of cancer as used herein, relates to any treatment which aims at improving the health status and/or prolonging (increasing) the lifespan of a patient. Said treatment may eliminate cancer, reduce the size or the number of tumors in a patient, arrest or slow the development of cancer in a patient, inhibit or slow the development of new cancer in a patient, decrease the frequency or severity of symptoms in a patient, and/or decrease recurrences in a patient who currently has or who previously has had cancer. A (therapeutic) treatment of cancer may be selected from the group consisting of surgery, chemotherapy, radiation therapy and targeted therapy.

The term "surgery", as used herein, includes the removal of tumors in an operation. It is a common treatment for cancer. A surgeon may remove the tumors using local excision.

The term "chemotherapy", as used herein, refers to the use of chemotherapeutic agents or combinations of chemotherapeutic agents, preferably to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the cerebrospinal fluid, an organ, or a body cavity such as the abdomen, the drugs mainly affect cancer cells in those areas (regional chemotherapy).

Chemotherapeutic agents according to the invention include cytostatic compounds and cytotoxic compounds. Traditional chemotherapeutic agents act by killing cells that divide rapidly, one of the main properties of most cancer cells. This means that chemotherapy also harms cells that divide rapidly under normal circumstances such as cells in the bone marrow, digestive tract, and hair follicles. This results in the most common side-effects of chemotherapy. According to the invention, the term "chemotherapy" preferably does not include antibodies that target proteins that are abnormally expressed in cancer cells (tumor antigens such as CLDN18.2) and act through recruiting the patient's immune system to destroy tumor cells. Antibodies that target proteins that are abnormally expressed in cancer cells (tumor antigens such as CLDN18.2) and act through a therapeutic moiety or agent conjugated to the antibody, however, can be viewed as a form of chemotherapy. However, in the strictest sense, the term "chemotherapy" according to the invention does not include targeted therapy.

According to the invention, the term "targeted therapy" relates to any therapy that can be used to target preferentially diseased cells such as cancer cells while non-diseased cells are not targeted or targeted to a lesser extent. Targeting of diseased cells preferably results in killing and/or impairment of proliferation or viability of diseased cells. Such therapy includes i) antibodies, antibody fragments, and proteins that are either naked or conjugated to a therapeutic moiety that target certain cell surface targets on diseased cells, such as tumor antigens, for example, CLDN18.2, (e.g. antibodies or antibody conjugates against CLDN18.2 as described herein) or ii) small molecules which impair proliferation or viability of diseased cells. In a specific embodiment, the agent binds to an antigen that is expressed at a greater level on diseased than on normal stem cells. In a specific embodiment, the agent binds specifically to a tumor antigen. Traditional chemotherapy or radiotherapy is not considered a "targeted therapy" despite its often being aimed at the tumours. Furthermore, the term "antibody therapy" according to the invention preferably does not include therapy with antibodies, fragments or derivatives thereof that are conjugated to a therapeutic moiety but merely relates to therapy with antibodies, fragments or derivatives thereof acting through recruiting the patient's immune system to destroy tumor cells.

In the context of the present invention, terms such as "protect", "prevent" or "prophylactic" relate to the prevention of the occurrence and/or the propagation of a disease in a subject and, in particular, to minimizing the chance that a subject will develop a disease or to delaying the development of a disease. For example, a subject at risk for cancer would be a candidate for therapy to prevent cancer.

By "being at risk" is meant a subject that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

The term "antigen" relates to an agent such as a protein or peptide comprising an epitope against which an immune response is directed and/or is to be directed. In a preferred embodiment, an antigen is a tumor-associated antigen, such as CLDN18.2, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the term "tumor-associated antigen" or "tumor antigen" preferably relates to proteins that are under normal conditions specifically expressed in a limited number of tissues and/or organs or in specific developmental stages and are expressed or aberrantly expressed in one or more tumor or cancer tissues. In the context of the present invention, the tumor-associated antigen is preferably associated with the cell surface of a cancer cell and is preferably not or only rarely expressed in normal tissues.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein such as CLDN18.2 preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "antibody" includes a glycoprotein comprising at least two heavy (H) chains and two light (L) chains inter-connected by disulfide bonds, and any molecule comprising an antigen-binding portion of such glycoprotein. The term "antibody" includes monoclonal antibodies, recombinant antibodies, human antibodies, humanized antibodies, chimeric antibodies, molecules comprising binding fragments or derivatives of antibodies, including, without limitation, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')2 fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

Naturally occurring antibodies are generally monospecific, i.e. they bind to a single antigen. The present invention comprises antibodies binding to a target cell (by engaging a tumor antigen) and a second entity such as a cytotoxic cell (e.g. by engaging the CD3 receptor). The antibodies of the present invention may be bispecific or multispecific such as trispecific, tetraspecific and so on.

The term "bispecific molecule" is intended to include an agent which has two different binding specificities. For example, the molecule may bind to, or interact with (a) a cell surface antigen such as CLDN18.2, and (b) a receptor such as an Fc receptor on the surface of an effector cell. The term "multispecific molecule" is intended to include an agent which has more than two different binding specificities. For example, the molecule may bind to, or interact with (a) a cell surface antigen such as CLDN18.2, (b) a receptor such as an Fc receptor on the surface of an effector cell, and (c) at least one other component. Accordingly, the term "antibody" includes, but is not limited to, bispecific, trispecific, tetraspecific, and other multispecific molecules which are directed to a tumor antigen, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

Antibodies may be derived from different species, including but not limited to mouse, rat, rabbit, guinea pig and human.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The antibodies described herein are preferably isolated. An "isolated antibody" as used herein, is intended to refer to an antibody which is substantially free of other antibodies having different antigenic specificities (e.g., an isolated antibody that specifically binds to a tumor antigen is substantially free of antibodies that specifically bind antigens other than the tumor antigen). An isolated antibody that specifically binds to an epitope, isoform or variant of a human tumor antigen may, however, have cross-reactivity to other related antigens, e.g., from other species (e.g., tumor antigen species homologs). Moreover, an isolated antibody may be substantially free of other cellular material and/or chemicals. In one embodiment of the invention, a combination of "isolated" monoclonal antibodies relates to antibodies having different specificities and being combined in a well defined composition or mixture.

In the context of the present invention, an antibody is capable of acting through recruiting the patient's immune system to destroy tumor cells if the antibody, in particular when bound to its target such as a tumor antigen on a diseased cell, elicits immune effector functions as described herein. Preferably, said immune effector functions are directed against cells such as cancer cells carrying a tumor antigen such as CLDN18.2 on their surface.

The term "immune effector functions" in the context of the present invention includes any functions mediated by components of the immune system that result e.g. in the inhibition of tumor growth and/or inhibition of tumor development, including inhibition of tumor dissemination and metastasis. Preferably, immune effector functions result in killing of cancer cells. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor antigen, cytolysis of the cells carrying the tumor antigen, and/or inhibition of proliferation of the cells carrying the tumor antigen.

Antibody-Dependent Cell-Mediated Cytotoxicity

ADCC describes the cell-killing ability of effector cells, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-Dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the CH2 domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

It has surprisingly been found that antibody-drug conjugates described herein are able to mediate killing of cells, in particular cells expressing CLDN18.2, such as cancer cells, by inducing complement dependent cytotoxicity (CDC) mediated lysis and/or antibody dependent cellular cytotoxicity (ADCC) mediated lysis. Thus, in one embodiment, the antibody-drug conjugates of the invention mediate killing of cells by inducing complement dependent cytotoxicity (CDC) mediated lysis and/or antibody dependent cellular cytotoxicity (ADCC) mediated lysis, preferably by inducing CDC mediated lysis and ADCC mediated lysis.

As used herein, an antibody is "derived from" a particular germline sequence if the antibody is obtained from a system by immunizing an animal or by screening an immunoglobulin gene library, and wherein the selected antibody is at least 90%, more preferably at least 95%, even more preferably at least 96%, 97%, 98%, or 99% identical in amino acid sequence to the amino acid sequence encoded by the germline immunoglobulin gene. Typically, an antibody derived from a particular germline sequence will display no more than 10 amino acid differences, more preferably, no more than 5, or even more preferably, no more than 4, 3, 2, or 1 amino acid difference from the amino acid sequence encoded by the germline immunoglobulin gene.

As used herein, the term "heteroantibodies" refers to two or more antibodies, derivatives thereof, or antigen binding regions linked together, at least two of which have different specificities. These different specificities include a binding specificity for an Fc receptor on an effector cell, and a binding specificity for an antigen or epitope on a target cell, e.g., a tumor cell.

The term "transfectoma", as used herein, includes recombinant eukaryotic host cells expressing an antibody, such as CHO cells, NS/0 cells, HEK293 cells, HEK293T cells, plant cells, or fungi, including yeast cells.

The invention includes all antibodies and derivatives of antibodies as described herein which for the purposes of the invention are encompassed by the term "antibody". The term "antibody derivatives" refers to any modified form of an antibody, e.g., a conjugate of the antibody and another agent or antibody, or an antibody fragment.

The term "antibody against a tumor antigen" or similar terms relates to an antibody directed to or having the ability of binding to the tumor antigen. The term "binding" according to the invention preferably relates to a specific binding.

According to the present invention, an antibody or antibody-drug conjugate is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An antibody or antibody-drug conjugate is not (substantially) capable of binding to a target if it has no significant affinity for said target and does not bind significantly, in particular does not bind detectably, to said target in standard assays. Preferably, the antibody or antibody-drug conjugate does not detectably bind to said target if present in a concentration of up to 2, preferably 10, more preferably 20, in particular 50 or 100 µg/ml or higher. Preferably, an antibody or antibody-drug conjugate has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody or antibody-drug conjugate is capable of binding. For example, if the $K_D$ for binding of an antibody or antibody-drug conjugate to the target to which the antibody or antibody-drug conjugate is capable of binding is $10^{-7}$ M, the $K_D$ for binding to a target for which the antibody or antibody-drug conjugate has no significant affinity would be is at least $10^{-6}$ M, $10^{-5}$ M, $10^{-4}$ M, $10^{-3}$ M, $10^{-2}$ M, or $10^{-1}$ M.

An antibody or antibody-drug conjugate is specific for a predetermined target if it is capable of binding to said predetermined target while it is not capable of binding to other targets, i.e. has no significant affinity for other targets and does not significantly bind to other targets in standard assays. According to the invention, an antibody or antibody-drug conjugate is specific for a tumor antigen such as CLDN18.2 if it is capable of binding to the tumor antigen but is not (substantially) capable of binding to other targets. Preferably, an antibody or antibody-drug conjugate is specific for a tumor antigen if the affinity for and the binding to such other targets does not significantly exceed the affinity for or binding to tumor antigen-unrelated proteins such as bovine serum albumin (BSA), casein, human serum albumin (HSA) or non-tumor antigen transmembrane proteins such as MHC molecules or transferrin receptor or any other specified polypeptide. Preferably, an antibody or antibody-drug conjugate is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody or antibody-drug conjugate to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIACORE®2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

According to the invention an antibody having the ability of binding to CLDN18.2 is an antibody capable of binding to an epitope present in CLDN18.2, preferably an epitope located within the extracellular domains of CLDN18.2, in particular the first extracellular domain, preferably amino acid positions 29 to 78 of CLDN18.2. In particular embodiments, an antibody having the ability of binding to CLDN18.2 is an antibody capable of binding to (i) an epitope on CLDN18.2 which is not present on CLDN18.1, preferably SEQ ID NO: 3, 4, and 5, (ii) an epitope localized on the CLDN18.2-loop1, preferably SEQ ID NO: 8, (iii) an epitope localized on the CLDN18.2-loop2, preferably SEQ ID NO: 10, (iv) an epitope localized on the CLDN18.2-loopD3, preferably SEQ ID NO: 11, (v) an epitope, which encompass CLDN18.2-loop1 and CLDN18.2-loopD3, or (vi) a non-glycosylated epitope localized on the CLDN18.2-loopD3, preferably SEQ ID NO: 9.

According to the invention an antibody having the ability of binding to CLDN18.2 preferably is an antibody having the ability of binding to CLDN18.2 but not to CLDN18.1. Preferably, an antibody having the ability of binding to CLDN18.2 is specific for CLDN18.2. Preferably, an antibody having the ability of binding to CLDN18.2 preferably is an antibody having the ability of binding to CLDN18.2 expressed on the cell surface. In particular preferred embodiments, an antibody having the ability of binding to CLDN18.2 binds to native epitopes of CLDN18.2 present on the surface of living cells. Preferably, an antibody having the ability of binding to CLDN18.2 binds to one or more peptides selected from the group consisting of SEQ ID NOs: 1, 3-11, 44, 46, and 48-50. Preferably, an antibody having the ability of binding to CLDN18.2 is specific for the afore mentioned proteins, peptides or immunogenic fragments or derivatives thereof. An antibody having the ability of binding to CLDN18.2 may be obtained by a method comprising the step of immunizing an animal with a protein or peptide comprising an amino acid sequence selected from the group consisting of SEQ ID NOs: 1, 3-11, 44, 46, and 48-50, or a nucleic acid or host cell expressing said protein or peptide. Preferably, the antibody binds to cancer cells, in particular cells of the cancer types mentioned above and, preferably, does not bind substantially to non-cancerous cells.

In a particularly preferred embodiment, an antibody having the ability of binding to CLDN18.2 is produced by a hybridoma deposited at the DSMZ (Mascheroder Weg 1b, 31824 Braunschweig, Germany; new address: Inhoffenstr. 7B, 31824 Braunschweig, Germany) and having the following designation and accession number:

a. 182-D1106-055, accession no. DSM ACC2737, deposited on Oct. 19, 2005
b. 182-D1106-056, accession no. DSM ACC2738, deposited on Oct. 19, 2005
c. 182-D1106-057, accession no. DSM ACC2739, deposited on Oct. 19, 2005 d. 182-D1106-058, accession no. DSM ACC2740, deposited on Oct. 19, 2005
e. 182-D1106-059, accession no. DSM ACC2741, deposited on Oct. 19, 2005
f. 182-D1106-062, accession no. DSM ACC2742, deposited on Oct. 19, 2005,
g. 182-D1106-067, accession no. DSM ACC2743, deposited on Oct. 19, 2005
h. 182-D758-035, accession no. DSM ACC2745, deposited on Nov. 17, 2005
i. 182-D758-036, accession no. DSM ACC2746, deposited on Nov. 17, 2005
j. 182-D758-040, accession no. DSM ACC2747, deposited on Nov. 17, 2005
k. 182-D1106-061, accession no. DSM ACC2748, deposited on Nov. 17, 2005
l. 182-D1106-279, accession no. DSM ACC2808, deposited on Oct. 26, 2006
m. 182-D1106-294, accession no. DSM ACC2809, deposited on Oct. 26, 2006,
n. 182-D1106-362, accession no. DSM ACC2810, deposited on Oct. 26, 2006.

Preferred antibodies according to the invention are those produced by and obtainable from the above-described hybridomas; i.e. 37G11 in the case of 182-D1106-055, 37H8 in the case of 182-D1106-056, 38G5 in the case of 182-D1106-057, 38H3 in the case of 182-D1106-058, 39F11 in the case of 182-D1106-059, 43A11 in the case of 182-D1106-062, 61C2 in the case of 182-D1106-067, 26B5 in the case of 182-D758-035, 26D12 in the case of 182-D758-036, 28D10 in the case of 182-D758-040, 42E12 in the case of 182-D1106-061, 125E1 in the case of 182-D1106-279, 163E12 in the case of 182-D1106-294, and 175D10 in the case of 182-D1106-362; and the chimerized and humanized forms thereof.

In one embodiment, an antibody having the ability of binding to CLDN18.2 is an antibody selected from the group consisting of (i) an antibody produced by and/or obtainable from a clone deposited under the accession no. DSM ACC2737, DSM ACC2738, DSM ACC2739, DSM ACC2740, DSM ACC2741, DSM ACC2742, DSM ACC2743, DSM ACC2745, DSM ACC2746, DSM ACC2747, DSM ACC2748, DSM ACC2808, DSM ACC2809, or DSM ACC2810, (ii) an antibody which is a chimerized or humanized form of the antibody under (i), (iii) an antibody having the specificity of the antibody under (i), and (iv) an antibody comprising the antigen binding portion or antigen binding site, in particular the variable region, of the antibody under (i) and preferably having the specificity of the antibody under (i).

Preferred antibodies, in particular chimerized antibodies and their sequences are shown in the following table.

In preferred embodiments, antibodies, in particular chimerised forms of antibodies according to the invention include antibodies comprising a heavy chain constant region (CH) comprising an amino acid sequence derived from a human heavy chain constant region such as the amino acid sequence represented by SEQ ID NO: 13 or a fragment thereof. In further preferred embodiments, antibodies, in particular chimerised forms of antibodies according to the invention include antibodies comprising a light chain constant region (CL) comprising an amino acid sequence derived from a human light chain constant region such as the amino acid sequence represented by SEQ ID NO: 12 or a fragment thereof. In a particular preferred embodiment, antibodies, in particular chimerised forms of antibodies according to the invention include antibodies which comprise a CH comprising an amino acid sequence derived from a human CH such as the amino acid sequence represented by SEQ ID NO: 13 or a fragment thereof and which comprise a CL comprising an amino acid sequence derived from a human CL such as the amino acid sequence represented by SEQ ID NO: 12 or a fragment thereof.

In one embodiment, an antibody having the ability of binding to CLDN18.2 is a chimeric mouse/human IgG1 monoclonal antibody comprising kappa, murine variable light chain, human kappa light chain constant region allotype Km (3), murine heavy chain variable region, human IgG1 constant region, allotype G1m (3).

In certain preferred embodiments, chimerised forms of antibodies include antibodies comprising a heavy chain comprising an amino acid sequence selected from the group consisting of SEQ ID NOs: 14, 15, 16, 17, 18, 19, 51, and a fragment thereof and/or comprising a light chain comprising an amino acid sequence selected from the group consisting of SEQ ID NOs: 20, 21, 22, 23, 24, 25, 26, 27, 28, and a fragment thereof.

In certain preferred embodiments, chimerised forms of antibodies include antibodies comprising a combination of heavy chains and light chains selected from the following possibilities (i) to (ix):

(i) the heavy chain comprises an amino acid sequence represented by SEQ ID NO: 14 or a fragment thereof and the light chain comprises an amino acid sequence represented by SEQ ID NO: 21 or a fragment thereof, (ii) the heavy chain comprises an amino acid sequence represented by SEQ ID NO: 15 or a fragment thereof and the light chain comprises an amino acid sequence represented by SEQ ID NO: 20 or a fragment thereof, (iii) the heavy chain comprises an amino acid sequence represented by SEQ ID NO: 16 or a fragment thereof and the

|  | clone | mAb | Isotype | variable region | chimerized antibody |
|---|---|---|---|---|---|
| heavy chain | 43A11 | 182-D1106-062 | IgG2a | SEQ ID NO: 29 | SEQ ID NO: 14 |
|  | 163E12 | 182-D1106-294 | IgG3 | SEQ ID NO: 30 | SEQ ID NO: 15 |
|  | 125E1 | 182-D1106-279 | IgG2a | SEQ ID NO: 31 | SEQ ID NO: 16 |
|  | 166E2 | 182-D1106-308 | IgG3 | SEQ ID NO: 33 | SEQ ID NO: 18 |
|  | 175D10 | 182-D1106-362 | IgG1 | SEQ ID NO: 32 | SEQ ID NO: 17 |
|  | 45C1 | 182-D758-187 | IgG2a | SEQ ID NO: 34 | SEQ ID NO: 19 |
| light chain | 43A11 | 182-D1106-062 | IgK | SEQ ID NO: 36 | SEQ ID NO: 21 |
|  | 163E12 | 182-D1106-294 | IgK | SEQ ID NO: 35 | SEQ ID NO: 20 |
|  | 125E1 | 182-D1106-279 | IgK | SEQ ID NO: 37 | SEQ ID NO: 22 |
|  | 166E2 | 182-D1106-308 | IgK | SEQ ID NO: 40 | SEQ ID NO: 25 |
|  | 175D10 | 182-D1106-362 | IgK | SEQ ID NO: 39 | SEQ ID NO: 24 |
|  | 45C1 | 182-D758-187 | IgK | SEQ ID NO: 38 | SEQ ID NO: 23 |
|  | 45C1 | 182-D758-187 | IgK | SEQ ID NO: 41 | SEQ ID NO: 26 |
|  | 45C1 | 182-D758-187 | IgK | SEQ ID NO: 42 | SEQ ID NO: 27 |
|  | 45C1 | 182-D758-187 | IgK | SEQ ID NO: 43 | SEQ ID NO: 28 | light chain comprises an amino acid sequence represented by SEQ ID NO: 22 or a fragment thereof, (iv) the heavy chain comprises an amino acid sequence represented by SEQ ID NO: 18 or a fragment thereof and the light chain comprises an amino acid sequence represented by SEQ ID NO: 25 or a fragment thereof, (v) the heavy chain comprises an amino acid sequence represented by SEQ ID NO: 17 or a fragment thereof and the light chain comprises an amino acid sequence represented by SEQ ID NO: 24 or a fragment thereof, (vi) the heavy chain comprises an amino acid sequence represented by SEQ ID NO: 19 or a fragment thereof and the light chain comprises an amino acid sequence represented by SEQ ID NO: 23 or a fragment thereof, (vii) the heavy chain comprises an amino acid sequence represented by SEQ ID NO: 19 or a fragment thereof and the light chain comprises an amino acid sequence represented by SEQ ID NO: 26 or a fragment thereof, (viii) the heavy chain comprises an amino acid sequence represented by SEQ ID NO: 19 or a fragment thereof and the light chain comprises an amino acid sequence represented by SEQ ID NO: 27 or a fragment thereof, (ix) the heavy chain comprises an amino acid sequence represented by SEQ ID NO: 19 or a fragment thereof and the light chain comprises an amino acid sequence represented by SEQ ID NO: 28 or a fragment thereof, and (x) the heavy chain comprises an amino acid sequence represented by SEQ ID NO: 51 or a fragment thereof and the light chain comprises an amino acid sequence represented by SEQ ID NO: 24 or a fragment thereof.

The antibodies according to (ii), (v) or (x) are preferred embodiments of an "antibody having the ability of binding to CLDN18.2". The antibody according to (v) or (x) is particularly preferred.

"Fragment" or "fragment of an amino acid sequence" as used above relates to a part of an antibody sequence, i.e. a sequence which represents the antibody sequence shortened at the N- and/or C-terminus, which when it replaces said antibody sequence in an antibody retains binding of said antibody to CLDN18.2. Preferably, a fragment of an amino acid sequence comprises at least 80%, preferably at least 90%, 95%, 96%, 97%, 98%, or 99% of the amino acid residues from said amino acid sequence. A fragment of an amino acid sequence selected from the group consisting of SEQ ID NOs: 14, 15, 16, 17, 18, 19, 20, 21, 22, 23, 24, 25, 26, 27, 28 and 51 preferably relates to said sequence wherein 17, 18, 19, 20, 21, 22 or 23 amino acids at the N-terminus are removed.

In a preferred embodiment, an antibody having the ability of binding to CLDN18.2 comprises a heavy chain variable region (VH) comprising an amino acid sequence selected from the group consisting of SEQ ID NOs: 29, 30, 31, 32, 33, 34, and a fragment thereof.

In a preferred embodiment, an antibody having the ability of binding to CLDN18.2 comprises a light chain variable region (VL) comprising an amino acid sequence selected from the group consisting of SEQ ID NO: 35, 36, 37, 38, 39, 40, 41, 42, 43, and a fragment thereof.

In certain preferred embodiments, an antibody having the ability of binding to CLDN18.2 comprises a combination of heavy chain variable region (VH) and light chain variable region (VL) selected from the following possibilities (i) to (ix):

(i) the VH comprises an amino acid sequence represented by SEQ ID NO: 29 or a fragment thereof and the VL comprises an amino acid sequence represented by SEQ ID NO: 36 or a fragment thereof, (ii) the VH comprises an amino acid sequence represented by SEQ ID NO: 30 or a fragment thereof and the VL comprises an amino acid sequence represented by SEQ ID NO: 35 or a fragment thereof, (iii) the VH comprises an amino acid sequence represented by SEQ ID NO: 31 or a fragment thereof and the VL comprises an amino acid sequence represented by SEQ ID NO: 37 or a fragment thereof, (iv) the VH comprises an amino acid sequence represented by SEQ ID NO: 33 or a fragment thereof and the VL comprises an amino acid sequence represented by SEQ ID NO: 40 or a fragment thereof, (v) the VH comprises an amino acid sequence represented by SEQ ID NO: 32 or a fragment thereof and the VL comprises an amino acid sequence represented by SEQ ID NO: 39 or a fragment thereof, (vi) the VH comprises an amino acid sequence represented by SEQ ID NO: 34 or a fragment thereof and the VL comprises an amino acid sequence represented by SEQ ID NO: 38 or a fragment thereof, (vii) the VH comprises an amino acid sequence represented by SEQ ID NO: 34 or a fragment thereof and the VL comprises an amino acid sequence represented by SEQ ID NO: 41 or a fragment thereof, (viii) the VH comprises an amino acid sequence represented by SEQ ID NO: 34 or a fragment thereof and the VL comprises an amino acid sequence represented by SEQ ID NO: 42 or a fragment thereof, (ix) the VH comprises an amino acid sequence represented by SEQ ID NO: 34 or a fragment thereof and the VL comprises an amino acid sequence represented by SEQ ID NO: 43 or a fragment thereof.

The antibodies according to (ii) or (v) are preferred embodiments of an "antibody having the ability of binding to CLDN18.2". The antibody according to (v) is particularly preferred.

According to the invention, the term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In a preferred embodiment, an antibody having the ability of binding to CLDN18.2 comprises a VH comprising a set of complementarity-determining regions CDR1, CDR2 and CDR3 selected from the following embodiments (i) to (vi):

(i) CDR1: positions 45-52 of SEQ ID NO: 14, CDR2: positions 70-77 of SEQ ID NO: 14, CDR3: positions 116-125 of SEQ ID NO: 14, (ii) CDR1: positions 45-52 of SEQ ID NO: 15, CDR2: positions 70-77 of SEQ ID NO: 15, CDR3: positions 116-126 of SEQ ID NO: 15, (iii) CDR1: positions 45-52 of SEQ ID NO: 16, CDR2: positions 70-77 of SEQ ID NO: 16, CDR3: positions 116-124 of SEQ ID NO: 16, (iv) CDR1: positions 45-52 of SEQ ID NO: 17, CDR2: positions 70-77 of SEQ ID NO: 17, CDR3: positions 116-126 of SEQ ID NO: 17, (v) CDR1: positions 44-51 of SEQ ID NO: 18, CDR2: positions 69-76 of SEQ ID NO: 18, CDR3: positions 115-125 of SEQ ID NO: 18, and (vi) CDR1: positions 45-53 of SEQ ID NO: 19, CDR2: positions 71-78 of SEQ ID NO: 19, CDR3: positions 117-128 of SEQ ID NO: 19.

In a preferred embodiment, an antibody having the ability of binding to CLDN18.2 comprises a VL comprising a set of complementarity-determining regions CDR1, CDR2 and CDR3 selected from the following embodiments (i) to (ix):

(i) CDR1: positions 47-58 of SEQ ID NO: 20, CDR2: positions 76-78 of SEQ ID NO: 20, CDR3: positions 115-123 of SEQ ID NO: 20, (ii) CDR1: positions 49-53 of SEQ ID NO: 21, CDR2: positions 71-73 of SEQ ID NO: 21, CDR3: positions 110-118 of SEQ ID NO: 21, (iii) CDR1: positions 47-52 of SEQ ID NO: 22, CDR2: positions 70-72 of SEQ ID NO: 22, CDR3: positions 109-117 of SEQ ID NO: 22, (iv) CDR1: positions 47-58 of SEQ ID NO: 23, CDR2: positions 76-78 of SEQ ID NO: 23, CDR3: positions 115-123 of SEQ ID NO: 23, (v) CDR1: positions 47-58 of SEQ ID NO: 24, CDR2: positions 76-78 of SEQ ID NO: 24, CDR3: positions 115-123 of SEQ ID NO: 24, (vi) CDR1: positions 47-58 of SEQ ID NO: 25, CDR2: positions 76-78 of SEQ ID NO: 25, CDR3: positions 115-122 of SEQ ID NO: 25, (vii) CDR1: positions 47-58 of SEQ ID NO: 26, CDR2: positions 76-78 of SEQ ID NO: 26, CDR3: positions 115-123 of SEQ ID NO: 26, (viii) CDR1: positions 47-58 of SEQ ID NO: 27, CDR2: positions 76-78 of SEQ ID NO: 27, CDR3: positions 115-123 of SEQ ID NO: 27, and (ix) CDR1: positions 47-52 of SEQ ID NO: 28, CDR2: positions 70-72 of SEQ ID NO: 28, CDR3: positions 109-117 of SEQ ID NO: 28.

In a preferred embodiment, an antibody having the ability of binding to CLDN18.2 comprises a combination of VH and VL each comprising a set of complementarity-determining regions CDR1, CDR2 and CDR3 selected from the following embodiments (i) to (ix):

(i) VH: CDR1: positions 45-52 of SEQ ID NO: 14, CDR2: positions 70-77 of SEQ ID NO: 14, CDR3: positions 116-125 of SEQ ID NO: 14, VL: CDR1: positions 49-53 of SEQ ID NO: 21, CDR2: positions 71-73 of SEQ ID NO: 21, CDR3: positions 110-118 of SEQ ID NO: 21, (ii) VH: CDR1: positions 45-52 of SEQ ID NO: 15, CDR2: positions 70-77 of SEQ ID NO: 15, CDR3: positions 116-126 of SEQ ID NO: 15, VL: CDR1: positions 47-58 of SEQ ID NO: 20, CDR2: positions 76-78 of SEQ ID NO: 20, CDR3: positions 115-123 of SEQ ID NO: 20, (iii) VH: CDR1: positions 45-52 of SEQ ID NO: 16, CDR2: positions 70-77 of SEQ ID NO: 16, CDR3: positions 116-124 of SEQ ID NO: 16, VL: CDR1: positions 47-52 of SEQ ID NO: 22, CDR2: positions 70-72 of SEQ ID NO: 22, CDR3: positions 109-117 of SEQ ID NO: 22, (iv) VH: CDR1: positions 44-51 of SEQ ID NO: 18, CDR2: positions 69-76 of SEQ ID NO: 18, CDR3: positions 115-125 of SEQ ID NO: 18, VL: CDR1: positions 47-58 of SEQ ID NO: 25, CDR2: positions 76-78 of SEQ ID NO: 25, CDR3: positions 115-122 of SEQ ID NO: 25, (v) VH: CDR1: positions 45-52 of SEQ ID NO: 17, CDR2: positions 70-77 of SEQ ID NO: 17, CDR3: positions 116-126 of SEQ ID NO: 17, VL: CDR1: positions 47-58 of SEQ ID NO: 24, CDR2: positions 76-78 of SEQ ID NO: 24, CDR3: positions 115-123 of SEQ ID NO: 24, (vi) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 23, CDR2: positions 76-78 of SEQ ID NO: 23, CDR3: positions 115-123 of SEQ ID NO: 23, (vii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 26, CDR2: positions 76-78 of SEQ ID NO: 26, CDR3: positions 115-123 of SEQ ID NO: 26, (viii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 27, CDR2: positions 76-78 of SEQ ID NO: 27, CDR3: positions 115-123 of SEQ ID NO: 27, and (ix) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-52 of SEQ ID NO: 28, CDR2: positions 70-72 of SEQ ID NO: 28, CDR3: positions 109-117 of SEQ ID NO: 28.

The antibodies according to (ii) or (v) are preferred embodiments of an "antibody having the ability of binding to CLDN18.2". The antibody according to (v) is particularly preferred.

In further preferred embodiments, an antibody having the ability of binding to CLDN18.2 preferably comprises one or more of the complementarity-determining regions (CDRs), preferably at least the CDR3 variable region, of the heavy chain variable region (VH) and/or of the light chain variable region (VL) of a monoclonal antibody against CLDN18.2, preferably of a monoclonal antibody against CLDN18.2 described herein, and preferably comprises one or more of the complementarity-determining regions (CDRs), preferably at least the CDR3 variable region, of the heavy chain variable regions (VH) and/or light chain variable regions (VL) described herein. In one embodiment said one or more of the complementarity-determining regions (CDRs) are selected from a set of complementarity-determining regions CDR1, CDR2 and CDR3 described herein. In a particularly preferred embodiment, an antibody having the ability of binding to CLDN18.2 preferably comprises the complementarity-determining regions CDR1, CDR2 and CDR3 of the heavy chain variable region (VH) and/or of the light chain variable region (VL) of a monoclonal antibody against CLDN18.2, preferably of a monoclonal antibody against CLDN18.2 described herein, and preferably comprises the complementarity-determining regions CDR1, CDR2 and CDR3 of the heavy chain variable regions (VH) and/or light chain variable regions (VL) described herein.

In one embodiment an antibody comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of antibodies made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment an antibody comprising one or more CDRs, a set of CDRs or a combination of sets of CDRs as described herein comprises said CDRs in a human antibody framework.

Reference herein to an antibody comprising with respect to the heavy chain thereof a particular chain, or a particular region or sequence preferably relates to the situation wherein all heavy chains of said antibody comprise said particular chain, region or sequence. This applies correspondingly to the light chain of an antibody.

In one embodiment, an antibody having the ability of binding to CLDN18.2 according to the invention relates to an antibody which recognizes, i.e. binds to, the same or essentially the same epitope as a CLDN18.2-binding antibody described herein, and/or competes with said CLDN18.2-binding antibody for binding to CLDN18.2.

According to the invention, an antibody having the ability of binding to CLDN18.2, in particular when present in the antibody-drug conjugate, preferably has an affinity and/or specificity for CLDN18.2 appropriate to allow endocytosis of the antibody and/or the antibody-drug conjugate.

The term "endocytosis" refers to the process where eukaryotic cells internalize segments of plasma membrane, cell-surface receptors and components from the extracellular fluid. Endocytosis mechanisms include receptor mediated endocytosis. The term "receptor-mediated endocytosis" refers to a biological mechanism by which a ligand, upon binding to its target, triggers membrane invagination and pinching, gets internalized and delivered into cytosol or transferred to appropriate intracellular compartments.

The present invention also envisions embodiments, wherein an "antibody having the ability of binding to CLDN18.2" has a meaning which encompasses any "binding agent to CLDN18.2". According to the invention, a "binding agent to CLDN18.2" includes any compound that has a binding capacity to CLDN18.2. Preferably, such binding agent comprises at least one binding domain for CLDN18.2. The term includes all artificial binding molecules (scaffolds) having a binding capacity to CLDN18.2 including but not limited to nanobodies, affibodies, anticalins, DARPins, monobodies, avimers, and microbodies. In one embodiment said binding agent binds to an extracellular domain of CLDN18.2. In one embodiment said binding agent binds to native epitopes of CLDN18.2 present on the surface of living cells. In one embodiment said binding agent binds to the first extracellular loop of CLDN18.2. In one embodiment said binding to CLDN18.2 is a specific binding.

The term "binding domain" characterizes in connection with the present invention a structure, e.g. of an antibody, which binds to/interacts with a given target structure/antigen/epitope. Thus, the binding domain according to the invention designates an "antigen-interaction-site".

Any agent that exerts a therapeutic effect on cancer cells can be used as the drug for conjugation to an anti-CLDN18.2 antibody or derivative thereof. Preferably, conjugation of the drug does not alter or significantly alter the binding characteristics, in particular the specificity, of the antibody, as discussed herein. Thus, the antibody-drug conjugate according to the invention preferably has the same or essentially the same binding characteristics, in particular the specificity, as the antibody used for conjugation. Accordingly, if certain binding characteristics are described herein for the antibody used for conjugation, it is preferred that also the antibody-drug conjugate has such binding characteristics. For example, if it is described that the antibody having the ability of binding to CLDN18.2 binds to an extracellular domain of CLDN18.2 and/or binds to the first extracellular loop of CLDN18.2, it is preferred that also the antibody-drug conjugate binds to an extracellular domain of CLDN18.2 and/or binds to the first extracellular loop of CLDN18.2.

Typically, the drug is a cytotoxic or cytostatic agent. A cytotoxin or cytotoxic agent includes any agent that is detrimental to and, in particular, kills cells.

Useful classes of cytotoxic agents include, for example, antitubulin agents, DNA minor groove binders (e.g., enediynes and lexitropsins), DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, nitrosoureas, platinols, pre-forming compounds, purine antimetabolites, puromycins, radiation sensitizers, steroids, taxanes (e.g., paclitaxel and docetaxel), topoisomerase inhibitors, *vinca* alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

Examples of anti-tubulin agents include, but are not limited to, dolastatins (e.g., auristatin E, AFP, MMAF, MMAE, AEB, AEVB), maytansinoids, taxanes (e.g., paclitaxel, docetaxel), T67 (Tularik), vinca alkyloids (e.g., vincristine, vinblastine, vindesine, and vinorelbine), baccatin derivatives, taxane analogs (e.g., epothilone A and B), nocodazole, colchicine and colcimid, estramustine, cryptophysins, cemadotin, combretastatins, discodermolide, and eleutherobin.

In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE.

In certain embodiments, the cytotoxic or cytostatic agent is a maytansinoid, another group of anti-tubulin agents. For example, in specific embodiments, the maytansinoid is maytansine, DM-1 or DM-4.

Maytansinoids are potent microtubule-targeted compounds that inhibit proliferation of cells at mitosis. Maytansinoids are derivatives of maytansine which is a 19-membered ansa macrolide structure attached to a chlorinated benzene ring. Maytansine has the following formula:

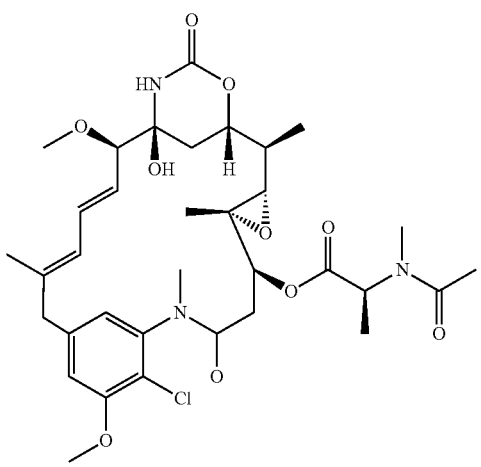 [SMILES: COc1cc2cc(c1Cl)N(C)C(O)C[C@H](OC(=O)[C@H](C)N(C)C(C)=O)[C@]1(C)O[C@H]1[C@H](C)[C@@H]1C[C@@](O)(NC(=O)O1)[C@H](OC)/C=C/C=C(\C)C2]

It was discovered that certain microbes also produce maytansinoids, such as maytansinol and C-3 maytansinol esters (U.S. Pat. No. 4,151,042). Synthetic maytansinol and maytansinol analogues have been reported, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,362,663; and 4,371,533, and Kawai et al (1984) Chem. Pharm. Bull. 3441-3451, herein incorporated by reference.

Maytansinoids are well known in the art and can be synthesized by known techniques or isolated from natural sources. Particularly preferred maytansinoids according to the invention are the thiol-containing derivatives of maytansine, such as DM1 and DM4. Such thiol-containing derivatives of maytansine include compounds wherein the methyl group bound to the carbonyl group is replaced by a group containing a free sulfhydryl group such as the group —R—SH where R represents an alkylene group or other carbon-containing group of atoms.

DM1, also known as mertansine, is a maytansinoid having the following formula:

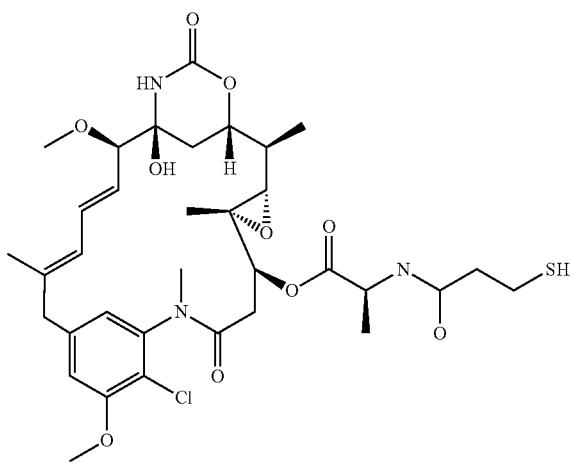 [SMILES: COc1cc2cc(c1Cl)N(C)C(=O)C[C@H](OC(=O)[C@H](C)NC(O)CCS)[C@]1(C)O[C@H]1[C@H](C)[C@@H]1C[C@@](O)(NC(=O)O1)[C@H](OC)/C=C/C=C(\C)C2]

In particular, the term "mertansine" or "DM1" refers to the compound $N^{2'}$-deacetyl-$N^{2'}$-(3-mercapto-1-oxopropyl)-maytansine.

"DM4" refers to the compound $N^{2'}$-deacetyl-$N^{2'}$-(4-methyl-4-mercapto-1-oxopentyl)-maytansine.

Anti-CLDN18.2 antibody-maytansinoid conjugates may be prepared by chemically linking an anti-CLDN18.2 antibody to a maytansinoid molecule without significantly diminishing the biological activity of either the antibody or the maytansinoid molecule. An average of 3-4 maytansinoid molecules may be conjugated per antibody molecule, although even one molecule of toxin/antibody is expected to enhance cytotoxicity over the use of naked antibody.

In this respect, the term "antibody covalently attached to at least one toxin drug moiety" includes situations where one or more molecules of the same drug are covalently attached to an antibody molecule as well as where different drugs are covalently attached to an antibody molecule. In the latter situation, one or more molecules of each of the different drugs may be attached to an antibody molecule, or a combination thereof (e.g. one molecule of one drug is attached while several molecules of another drug are attached).

In some embodiments of the invention, an antibody is conjugated to dolastatins or dolostatin peptidic analogs and derivatives, the auristatins (U.S. Pat. Nos. 5,635,483; 5,780,588, herein incorporated by reference). Auristatins are synthetic analogs of dolostatin 10, a natural product derived from a marine mollusk, Dolabela auricularia. Like the maytansinoids, auristatins are microtubule disruptors. The dolastatin or auristatin drug moiety may be attached to the antibody through the N (amino) terminus or the C (carboxyl) terminus of the peptidic drug moiety.

Exemplary auristatin embodiments include monomethylauristatin drug moieties such as MMAE and MMAF which preferably are N-terminus linked.

MMAE, also known as Monomethyl auristatin E, has the following formula:

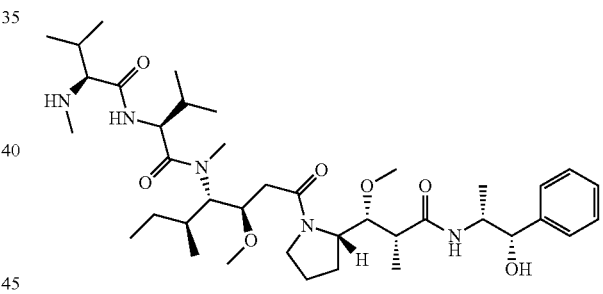

In particular, the term "MMAE" refers to the compound (S)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino) butanamido)butanamide. MMAE is actually desmethyl-auristatin E, i.e., the N-terminal amino group has only one methyl substituent instead of two as in auristatin E itself.

Particularly preferred according to the invention are antibody-vcAuristatin conjugates such as antibody-vcMMAE conjugates. According to the invention, the term "antibody-vcAuristatin" or "vcMMAE" refers to an antibody-drug conjugate (ADC) comprising an auristatin such as MMAE, linked via a linker comprising the lysosomally cleavable dipeptide, valine-citrulline (vc), to the antibody.

MMAF, also known as Monomethyl auristatin F, refers to the compound (S)-2-((2R,3R)-3-((S)-1-((3R,4S,5S)-4-((S)-N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid.

The generation of antibody-drug conjugates can be accomplished by any technique known to the skilled artisan. Antibody-drug conjugates can be prepared by binding the drug to an antibody in accordance with a conventional technique. An antibody and a drug may be directly bound to each other via their own linker groups or indirectly via a linker or other substance.

A number of different reactions are available for covalent attachment of drugs to antibodies. This is often accomplished by reaction of the amino acid residues of the antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of the antibody molecule. Also available for attachment of drugs to antibodies is the Schiff base reaction. This method involves the periodate oxidation of a drug that contains glycol or hydroxy groups, thus forming an aldehyde which is then reacted with the antibody molecule. Attachment occurs via formation of a Schiff base with amino groups of the antibody molecule. Isothiocyanates can also be used as coupling agents for covalently attaching drugs to antibodies. Other techniques are known to the skilled artisan and within the scope of the present invention.

There are many linking groups known in the art for making antibody-drug conjugates. A linker preferably comprises one or more functional groups that react with either or both of the antibody and the drug. Examples of functional groups include amino, carboxyl, mercapto, maleimide, and pyridinyl groups.

In one embodiment of the invention, an antibody is linked with a drug via a bifunctional crosslinking reagent. As used herein, a "bifunctional crosslinking reagent" refers to a reagent that possesses two reactive groups one of which is capable of reacting with an antibody, while the other one is capable of reacting with the drug to link the antibody with the drug, thereby forming a conjugate. Any suitable bifunctional crosslinking reagent can be used in connection with the invention, so long as the linker reagent provides for retention of the drug, e.g., cytotoxicity, and targeting characteristics of the antibody. Preferably, the linker molecule joins the drug to the antibody through chemical bonds, such that the drug and the antibody are chemically coupled (e.g., covalently bonded) to each other.

In one embodiment, the bifunctional crosslinking reagent comprises non-cleavable linkers. A non-cleavable linker is any chemical moiety that is capable of linking a drug, such as a maytansinoid, to an antibody in a stable, covalent manner. Preferably, a non-cleavable linker is not cleavable under physiological conditions, in particular inside a cell. Thus, non-cleavable linkers are substantially resistant to acid-induced cleavage, light-induced cleavage, peptidase-induced cleavage, esterase-induced cleavage, and disulfide bond cleavage, at conditions under which the drug or the antibody remains active. Suitable crosslinking reagents that form non-cleavable linkers between a drug and an antibody are well known in the art. In one embodiment, the drug is linked to the antibody through a thioether bond.

In one particularly preferred embodiment, the linking reagent is a cleavable linker. Preferably, a cleavable linker is cleavable under physiological conditions, in particular inside a cell. Examples of suitable cleavable linkers include disulfide linkers, acid labile linkers, photolabile linkers, peptidase labile linkers, and esterase labile linkers.

Examples of linkers include, but are not limited to, N-succinimidyl-3-(2-pyridyldithio)butyrate (SPDB), N-succinimidyl-3-(2-pyridyldithio)propionate (SPDP), sulfosuccinimidyl-4-(N-maleimidomethyl)cyclohexane-1-carboxylate (Sulfo-SMCC), N-succinimidyl-4-(maleimidomethyl) cyclohexanecarboxylate (SMCC), N-succinimidyl-4-(N-maleimidomethyl)-cyclohexane-1-carboxy-(6-amidocaproate) (LC-SMCC), 4-maleimidobutyric acid N-hydroxysuccinimide ester (GMBS), 3-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl-4-(p-maleimidophenyl)-butyrate (SMPB), N-(p-maleimidophenyl)isocyanate (PMPI), 6-maleimidocaproyl (MC), maleimidopropanoyl (MP), p-aminobenzyloxycarbonyl (PAB), N-succinimidyl-4-(2-pyridylthio)pentanoate (SPP), and N-succinimidyl (4-iodoacetyl)aminobenzoate (SIAB). A peptide linker such as valine-citrulline (Val-Cit) or alanine-phenylalanine (ala-phe) may also be used, and any of the aforementioned linkers may be used in adequate combination.

Disulfide containing linkers are linkers cleavable through disulfide exchange, which can occur under physiological conditions. In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene).

Acid labile linkers are linkers cleavable at acid pH. For example, certain intracellular compartments, such as endosomes and lysosomes, have an acidic pH (pH 4-5), and provide conditions suitable to cleave acid labile linkers. Acid labile linkers are relatively stable under neutral pH conditions, such as those in the blood, but are unstable at below pH 5.5 or 5.0. For example, a hydrazone, semicarbazone, thiosemicarbazone, cis-aconitic amide, orthoester, acetal, ketal, or the like can be used.

Photolabile linkers are useful at the body surface and in many body cavities that are accessible to light. Furthermore, infrared light can penetrate tissue.

Peptidase labile linkers can be used to cleave certain peptides inside or outside cells. In one embodiment, the cleavable linker is cleaved under mild conditions, i.e., conditions within a cell under which the activity of the cytotoxic agent is not affected.

The linker can be or can comprise, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). In specific embodiments, the peptidyl linker cleavable by an intracellular protease is a valine-citrulline (Val-Cit; vc) linker or a phenylalanine-lysine (Phe- Lys) linker. One advantage of using intracellular proteolytic release of the therapeutic agent is that the agent is typically attenuated when conjugated and the serum stabilities of the conjugates are typically high.

In one particularly preferred embodiment, the linker according to the invention comprises or consists of the dipeptide valine (Val)—citrulline (Cit) (vc), which is cleaved by cathepsin inside tumour cells.

Figure 1:
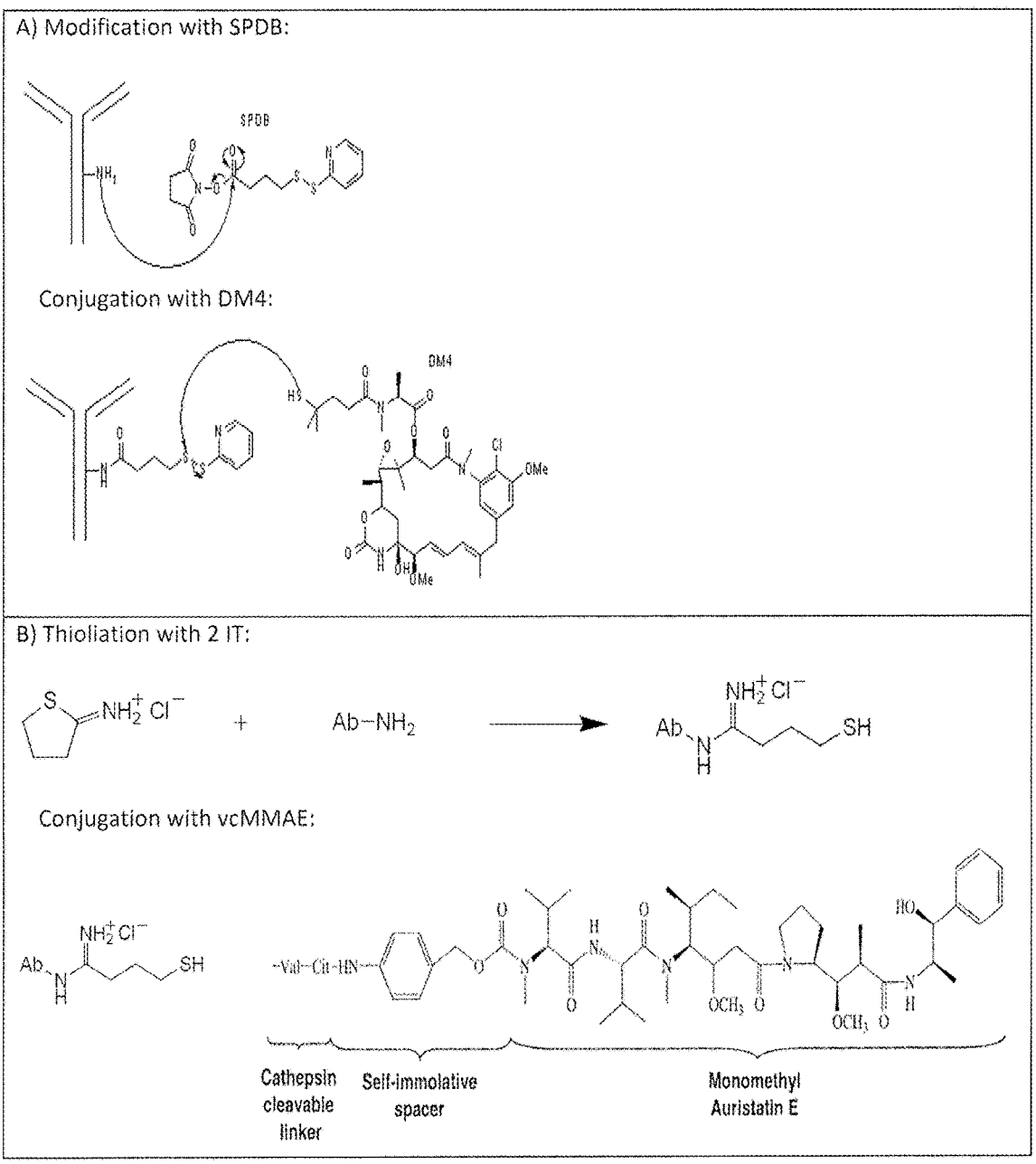
FIG. 1: Antibody drug conjugation.

In one embodiment, the drug is a maytansinoid such as DM4 which is coupled to an antibody having the ability of binding to CLDN18.2 via an amino and sulfhydryl reactive heterobifunctional protein crosslinker which reacts with primary amines (as found in lysine side chains or the N-terminus of proteins) of the antibody and with the sulhydryl group of the maytansinoid to yield a reversible disulfide bond. In one embodiment, the amino and sulfhydryl reactive heterobifunctional protein crosslinker is SPDB (N-succinimidyl-3-(2-pyridyldithio)butyrate), which reacts via an N-hydroxysuccinimide (NHS) ester with primary amines (as found in lysine side chains or the N-terminus of proteins) of the antibody and via a pyridinyldisulfide group with the sulhydryl group of DM4 to yield a reversible disulfide bond (FIG. 1).

In one embodiment, the drug is an auristatin such as MMAE which is coupled to an antibody having the ability of binding to CLDN18.2 via a peptide linker such as a cathepsin cleavable peptide linker, in particular Val-Cit (vc). In one embodiment, the antibody having the ability of binding to CLDN18.2 is thiolated, e.g. with the heterobifunctional linker 2-IT (2-iminothiolane) which reacts with free amines of lysine residues.

In one particularly preferred embodiment, an antibody-drug conjugate according to the invention comprises an antibody comprising a heavy chain comprising an amino acid sequence represented by SEQ ID NO: 32 or a fragment thereof or a variant of said amino acid sequence or fragment and a light chain comprising an amino acid sequence represented by SEQ ID NO: 39 or a fragment thereof or a variant of said amino acid sequence or fragment coupled (preferably through its amino groups) to DM4 (preferably through its sulfhydryl group). In one embodiment, the antibody is coupled to DM4 through a SPDB linker.

In one embodiment, an antibody-drug conjugate according to the invention comprises an antibody comprising a heavy chain comprising an amino acid sequence represented by SEQ ID NO: 17 or 51 or a fragment thereof or a variant of said amino acid sequence or fragment and a light chain comprising an amino acid sequence represented by SEQ ID NO: 24 or a fragment thereof or a variant of said amino acid sequence or fragment coupled (preferably through its amino groups) to DM4 (preferably through its sulfhydryl group). In one embodiment, the antibody is coupled to DM4 through a SPDB linker.

In one particularly preferred embodiment, an antibody-drug conjugate according to the invention comprises an antibody comprising a heavy chain comprising an amino acid sequence represented by SEQ ID NO: 32 or a fragment thereof or a variant of said amino acid sequence or fragment and a light chain comprising an amino acid sequence represented by SEQ ID NO: 39 or a fragment thereof or a variant of said amino acid sequence or fragment coupled (preferably through its amino groups) to MMAE (preferably through its N-terminal amino group). In one embodiment, the antibody is coupled to MMAE through a linker comprising the dipeptide vc.

In one particularly preferred embodiment, an antibody-drug conjugate according to the invention comprises an antibody comprising a heavy chain comprising an amino acid sequence represented by SEQ ID NO: 17 or 51 or a fragment thereof or a variant of said amino acid sequence or fragment and a light chain comprising an amino acid sequence represented by SEQ ID NO: 24 or a fragment thereof or a variant of said amino acid sequence or fragment coupled (preferably through its amino groups) to MMAE (preferably through its N-terminal amino group). In one embodiment, the antibody is coupled to MMAE through a linker comprising the dipeptide vc.

The term "nucleic acid", as used herein, is intended to include DNA and RNA. A nucleic acid may be single-stranded or double-stranded, but preferably is double-stranded DNA.

According to the invention, the term "expression" is used in its most general meaning and comprises the production of RNA or of RNA and protein/peptide. It also comprises partial expression of nucleic acids. Furthermore, expression may be carried out transiently or stably.

The teaching given herein with respect to specific amino acid sequences, e.g. those shown in the sequence listing, in particular those referred to herein by indicating a SEQ ID NO: is to be construed so as to also relate to variants of said specific sequences. Such variant sequences may be functionally equivalent to said specific sequences, e.g. amino acid sequences exhibiting properties identical or similar to those of the specific amino acid sequences. One important property is to retain binding of an antibody to its target. Preferably, a sequence which is a variant with respect to a specific sequence, when it replaces the specific sequence in an antibody retains binding of said antibody to CLDN18.2.

It will be appreciated by those skilled in the art that in particular the sequences of the CDR, hypervariable and variable regions can be modified without losing the ability to bind CLDN18.2. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence, such as an amino acid sequence referred to herein by indicating a SEQ ID NO: and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-CLDN18.2 antibodies when immunized with CLDN18.2 antigen and/or cells expressing CLDN18.2. The human heavy chain transgene can be integrated into the chromosomal DNA of the mouse, as is the case for transgenic mice, e.g., HuMAb mice, such as HCo7 or HCo12 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to CLDN18.2 (e.g., IgG, IgA and/or IgE) by undergoing V-D-J recombination and isotype switching.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

Antibodies described herein can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined specificity e.g. see Babcock et al., 1996; A novel strategy for generating monoclonal antibodies from single, isolated lymphocytes producing antibodies of defined specificities. For details of recombinant antibody engineering see also Welschof and Kraus, Recombinant antibodies for cancer therapy ISBN-0-89603-918-8 and Benny K. C. Lo Antibody Engineering ISBN 1-58829-092-1.

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Antibodies also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimerization

The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerization of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The ability of antibodies to bind an antigen can be determined using standard binding assays (e.g., ELISA, Western Blot, Immunofluorescence and flow cytometric analysis).

To purify antibodies, selected hybridomas can be grown in two-liter spinner-flasks for monoclonal antibody purification. Alternatively, antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected monoclonal antibodies bind to unique epitopes, site-directed or multi-site directed mutagenesis can be used.

To determine the isotype of antibodies, isotype ELISAs with various commercial kits (e.g. Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

In order to demonstrate presence of antibodies in sera of immunized mice or binding of monoclonal antibodies to living cells expressing antigen, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from non-specific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate presence of antibodies in sera of immunized mice or binding of monoclonal antibodies to living cells expressing antigen, immunofluorescence microscopy analysis can be used. For example, cell lines expressing either spontaneously or after transfection antigen and negative controls lacking antigen expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against the antigen for 30 min. at 25° C. After washing, cells can be reacted with an Alexa555-labelled anti-mouse IgG secondary antibody (Molecular Probes) under the same conditions. Cells can then be examined by fluorescence microscopy.

Cell extracts from cells expressing antigen and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Antibodies can be further tested for reactivity with antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection antigen. For immunostaining, antibodies reactive to antigen can be incubated followed by horseradish-peroxidase conjugated goat anti-mouse or goat anti-rabbit antibodies (DAKO) according to the vendors instructions.

Antibody conjugates which bind to CLDN18.2 also can be tested in an in vivo model (e.g. in immune deficient mice carrying xenografted tumors inoculated with cell lines expressing CLDN18.2, e.g. DAN-G, SNU-16, or KATO-III, or after transfection, e.g. HEK293) to determine their efficacy in controlling growth of CLDN18.2-expressing tumor cells.

Antibody conjugates can be administered to tumor free mice followed by injection of tumor cells to measure the effects of the antibody conjugates to prevent formation of tumors or tumor-related symptoms. Antibody conjugates can be administered to tumor-bearing mice to determine the therapeutic efficacy of respective antibody conjugates to reduce tumor growth, metastasis or tumor related symptoms. Antibody conjugate application can be combined with application of other substances as cystostatic drugs, growth factor inhibitors, cell cycle blockers, angiogenesis inhibitors or other antibodies to determine synergistic efficacy and potential toxicity of combinations. To analyze toxic side effects mediated by antibody conjugates animals can be inoculated with antibody conjugates or control reagents and thoroughly investigated for symptoms possibly related to CLDN18.2 antibody conjugate therapy. Possible side effects of in vivo application of CLDN18.2 antibody conjugates particularly include toxicity at CLDN18.2 expressing tissues including stomach.

Mapping of epitopes recognized by antibodies can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

The compounds and agents described herein may be administered in the form of any suitable pharmaceutical composition.

Pharmaceutical compositions are preferably sterile and contain an effective amount of the antibody conjugates described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions provided herein may be used alone or in combination with conventional therapeutic regimens such as surgery, irradiation, chemotherapy and/or bone marrow transplantation (autologous, syngeneic, allogeneic or unrelated).

Treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment may be effectively combined with various other drugs. Among those are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neoangiogenesis, survival of malignant cells or metastases, potentially converting cancer into a chronic disease.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by an altered expression pattern of CLDN18.2.

For example, in one embodiment, the agents and compositions described herein can be used to treat a patient with a cancer disease, e.g., a cancer disease such as described herein characterized by the presence of cancer cells expressing CLDN18.2.

The pharmaceutical compositions and methods of treatment described according to the invention may also be used for immunization or vaccination to prevent a disease described herein.

The present invention is further illustrated by the following examples which are not be construed as limiting the scope of the invention.

EXAMPLES

Example 1: Materials and Methods

1. Endocytosis

Endocytosis of CLDN18.2 bound IMAB362 was determined using a cytotoxicity based endocytosis assay that relies on the co-internalization of the target bound antibody and a saporin-conjugated anti-human or anti-mouse IgG Fab fragment (Fab-ZAP human, Advanced Targeting Systems, IT-51, Lot: #93-23; Fab-ZAP mouse, Advanced Targeting Systems, IT-48, Lot: #93-21). Saporin is a ribosome-inactivating protein, which upon internalization inhibits protein biosynthesis and therefore results in cell death. To guarantee optimal cell lysis, Fab-ZAP antibody was applied in at least 6-fold molarity compared to the target antibody.

Stably transfected HEK293~CLDN18.2 cells were harvested with 0.05% Trypsin/EDTA (Gibco®, 25300-054) and $2.5 \times 10^3$ cells/well were seeded in 50 µl growth medium in a 96-well cell culture plate. After 24 h, 25 µl of Fab-ZAP and 25 µl of anti-CLDN18.2 mAB or isotype control antibody diluted in cell culture medium were added to the cells (Table 1). Cells were cultured for additional 72 h.

TABLE 1

Anti-CLDN18.2 mAB and Fab-ZAP concentrations for endocytosis assay.

| Dilution | Final Concentration [ng/ml] | |
| --- | --- | --- |
| | anti-CLDN18.2 | Fab-ZAP |
| D1 | 187.5 | 825 |
| D2 | 75.0 | 825 |
| D3 | 30.0 | 825 |
| D4 | 12.0 | 825 |
| D5 | 4.800 | 825 |
| D6 | 1.920 | 825 |
| D7 | 0.768 | 825 |
| D8 | 0.307 | 825 |
| D9 | 0.123 | 825 |

Molecular weight: ~150 kDa for IMAB362 and 110 kDa for FabZAP.

Cell viability was analyzed as described in 6. Cells incubated without antibodies in the presence of Fab-ZAP were used as control.

2. Epitope Mapping

The antigenic epitope responsible for CLDN18.2 specificity was analyzed by flow cytometry (see 5) on HEK293T cells transiently overexpressing CLDN18.2 mutants. A total of eight CLDN18.2 mutants with single amino acid substitutions within the first extracellular domain were generated by PCR. Therefore, amino acids of CLDN18.2 were substituted with amino acids of the homologous protein CLDN18.1 at corresponding positions. HEK293T cells were co-transfected with plasmids coding for a specific CLDN18.2 mutant and EGFP as reporter gene. Purified antibodies were tested at a concentration of 5 µg/ml, whereas antibodies derived from hybridoma supernatants were diluted up to 1:4 before testing. To determine whether the antibody binding was influenced by a specific amino acid substitution, the mean fluorescence intensity (MFI) measured in the transfected (EGFP positive) cell population was compared between a mutant exhibiting the highest MFI value and the mutant of interest. If MFI of the mutant of interest was below 50% the amino acid residue was characterized to be essential for antibody binding and CLDN18.2 specificity.

3. Antibody Drug Conjugates

The conjugations of DM4 and vcMMAE to the monoclonal antibody IMAB362 (batch #p412118) and the analytical characterization were performed at Piramal Healthcare (Grangemouth, UK). The methods are briefly described in the next section:

DM4 was coupled to IMAB362 via SPDB (N-succinimidyl-3-(2-pyridyldithio)butyrate). The SPDB reagent is an amino and sulfhydryl reactive heterobifunctional protein crosslinker which reacts via an N-hydroxysuccinimide (NHS) ester with primary amines (as found in lysine side chains or the N-terminus of proteins) of the antibody and via a pyridinyldisulfide group with the sulhydryl group of DM4 to yield a reversible disulfide bond (FIG. 1). In brief, for DM4 conjugation, IMAB362 was diafiltered into PBS buffer (pH 7.2) using an ultra centrifugal filter and coupled to SPDB at a molar ratio of 1:6 (IMAB362:SPDB) for 1 h at RT. The modified antibody was dialyzed against 35 mM citrate buffer (pH 5.5) and the linker to antibody ratio was determined. DM4 was conjugated to IMAB362-SPDB at a molar ratio of 1:6 (IMAB362-SPDB:DM4) for 19 h at 2-8° C. The conjugated antibody was adjusted to the storage buffer (20 mM His, 85 mg/ml sucrose, pH 5.8) and stored at −80° C. Drug antibody ratio was analyzed by UV spectrometry, the monomer content by SEC-HPLC and free drug content by RP-HPLC. vcMMAE was coupled to thiolated IMAB362. Therefore, IMAB362 was initially thiolated with the heterobifunctional linker 2-IT (2-iminothiolane) which reacts with free amines of lysine residues. Then, vcMMAE, containing the cathepsin cleavable peptide linker Val-Cit (vc), was conjugated via valine to the sulfhydryl group of the thiolated antibody (FIG. 1). In brief, IMAB362 was diafiltered into PBS buffer (pH 7.2) using an ultra centrifugal filter and incubated with 2-IT at a molar ratio of 1:20 (IMAB362:2-IT) for 2 h at RT. The modified antibody was dialyzed into 35 mM citrate buffer (pH 5.5) and the linker to antibody ratio was determined. Thereafter, vcMMAE was conjugated to thiolated IMAB362 at a molar ratio of 1:6 (IMAB362-SH:vcMMAE) by incubation for 20 h at 2-8° C. Conjugated antibodies were dialyzed into storage buffer (20 mM His, 85 mg/mL sucrose, pH 5.8) and stored at −80° C. Drug antibody ratio was analyzed by UV spectrometry, the monomer content by SEC-HPLC and free drug content by RP-HPLC.

4. Cell Culture

Cell lines were cultivated in accordance with the suppliers' instructions and Ganymed's cell line data sheets in cell-type specific medium at 37° C. in humidified incubators with 5% or 7.5% $CO_2$ (Table 2). Cell culture media and supplements were obtained from Invitrogen®, Gibco® and Sigma®.

TABLE 2

Cell model systems.

| Cell line | Species/tissue/disease | Medium | Incubation |
|---|---|---|---|
| HEK293~mock | human embryonic kidney | DMEM/F12 (10% FCS, 1% pen/strep, 1.5 mg/ml geneticin) | 7.5% $CO_2$, 37° C. |
| HEK293~CLDN18.2 | human embryonic kidney (stably transfected with human CLDN18.2) | DMEM/F12 (10% FCS, 1% pen/strep, 1.5 mg/ml geneticin) | 7.5% $CO_2$, 37° C. |
| HEK293~CLDN18.1 | human embryonic kidney (stably transfected with human CLDN18.1) | DMEM/F12 (10% FCS, 1% pen/strep, 1.5 mg/ml geneticin) | 7.5% $CO_2$, 37° C. |
| BxPC-3 | human pancreas adenocarcinoma | RPMI (10 mM HEPES, 1 mM sodium pyruvate, 4.5 g/l glucose, 10% FCS) | 5% CO2, 37° C. |
| BxPC-3~CLDN18.2 | human pancreas adenocarcinoma (stably transduced with human CLDN18.2) | RPMI (10 mM HEPES, 1 mM sodium pyruvate, 4.5 g/l glucose, 1x sodium bicarbonate, 10% FCS, 0.5 μg/ml blasticidin) | 5% CO2, 37° C. |
| NCI-N87 | human gastric carcinoma | RPMI (10 mM HEPES, 1 mM sodium pyruvate, 4.5 g/l glucose, 10% FCS) | 5% $CO_2$, 37° C. |
| NCI-N87~CLDN18.2 | human gastric carcinoma (stably transduced with human CLDN18.2) | RPMI (10 mM HEPES + 1 mM sodium pyruvate, 4.5 g/l glucose, 10% FCS, 1.5 μg/ml blasticidin) | 5% $CO_2$, 37° C. |
| DAN-G 1C5F2 | human pancreas adenocarcinoma | RPMI (10% FCS, 1% pen/strep) | 5% $CO_2$, 37° C. |
| NUGC-4 10cF7-5 sort 3a | human gastric adenocarcinoma | RPMI (10% FCS, 1% pen/strep) | 5% $CO_2$, 37° C. |
| NUGC-4 10cE8 | human gastric adenocarcinoma | RPMI (10% FCS, 1% pen/strep) | 5% $CO_2$, 37° C. |
| PA-1(Luc) | human ovarian teratocarcinoma | EMEM (1 mM sodium pyruvate, 0.1 mM NEAA; 1.5 g/l sodium bicarbonate, 10% FCS) | 5% $CO_2$, 37° C. |

5. Flow Cytometry

The relative binding affinities and specificities of anti-CLDN18.2 naked antibodies and antibody drug conjugates were determined by flow cytometry using CLDN18.2 positive and negative cell lines.

Cells from an exponentially growing culture were harvested with 0.05% Trypsin/EDTA (Gibco®, 25300-054), and counted using a Neubauer counting chamber. Cells were centrifuged 5 min at 1,500 rpm (468×g), the supernatant was discarded and cells were resuspended in FACS buffer (PBS containing 2% FCS (Gibco®, 10270-106) for analysis with toxin-conjugated antibodies, PBS containing 2% FCS and 2 mM EDTA for screening of CLDN18.2 reactive naked antibodies) at $2 \times 10^6$ cells/ml. 100 μl of the cell suspension per well (correspond to $2 \times 10^5$ cells/well) were transferred to a round bottom 96-well microtiter plate. After centrifugation for 1 min at 1500 rpm, supernatant was discarded and cells were resuspended in FACS buffer containing toxin-conjugated or naked antibodies at appropriate concentrations (up to 20 μg/ml for relative affinity measurement or 50 μg/ml for expression control) and incubated for 30-45 min at 4° C. (Table 3). The cells were centrifuged for 1 min at 1500 rpm and the supernatant was discarded. After the cells were washed three times with FACS buffer, they were resuspended in FACS buffer containing APC-conjugated anti-human IgG (Jackson Immuno Research, 109-136-170) or APC-conjugated goat-anti-mouse IgG (Jackson Immuno Research, 115-136-146) or Protein L-FITC (1 μg/ml, analysis of chim mAB294) and incubated for 30 min at 4° C. (Table 3). After incubation, 100 μl FACS buffer were added to each sample, the cells were centrifuged for 1 min at 1500 rpm and the supernatant was discarded. The washing step with FACS buffer was repeated twice. Finally, the cells were resuspended in 100 μl FACS buffer and binding was determined using a BD FACSArray™ Bioanalyzer.

It should be noted that toxin-conjugated and naked antibodies were applied at equal concentrations. Differences between the molecular weight of the antibodies were neglected.

TABLE 3

Flow cytometry experimental details.

| Analysis | Primary antibody | Secondary antibody |
|---|---|---|
| Comparison of IMAB362 with IMAB362-DM4 and IMAB362-vcMMAE | 100 μl<br>0.1, 0.3, 0.9, 3.1, 10.9, 38.1<br>133.3, 466.5, 1632.7,<br>5714.3, 20000 ng/ml<br>45 min 4° C. | 50 μl<br>dilution 1:200<br>30 min |
| Comparison of IMAB362 with murine or chimeric CLDN18.2 reactive antibodies | 50 μl<br>19.5, 39.1, 78.1, 156.3, 312.6,<br>625, 1250, 2500, 5000,<br>10000, 20000 ng/ml<br>30 min 4° C. | 30 μl<br>dilution 1:100<br>30 min |
| Comparison of IMAB362 with chim mAB294 | 50 μl<br>19.5, 39.1, 78.1, 156.3, 312.6,<br>625, 1250, 2500, 5000,<br>10000, 20000 ng/ml<br>30 min 4° C. | 50 μl<br>1 μg/ml<br>30 min |

6. Viability Assay

The effect of IMAB362-DM4 and IMAB362-vcMMAE on cell viability was determined using a colorimetric assay that detects cellular metabolic activities. The assay is based on the ability of metabolically active cells to reduce yellow XTT (2,3-Bis-(2-methoxy-4-nitro-5-sulfophenyl)-2H-tetrazolium-5-carboxanilide) to an orange colored formazan compound which can be detected by spectrophotometry. The intensity of the dye is proportional to the number of living cells.

Cells were harvested with 0.05% Trypsin/EDTA (Gibco®, 25300-054), resuspended in cell culture medium (Table 2) and 50 μl of the cell suspension with the corresponding amount of cells were seeded per well in 96-well cell culture plates (Table 4). After 24 h, toxin-conjugated IMAB362 or control antibodies diluted in 50 μl medium at appropriate concentrations were added and cells were cultured for another 72 h.

TABLE 4

Overview of cell lines used in viability assays.

| Cell line | Cell number per 96 well |
| --- | --- |
| NCI-N87~CLDN18.2 | 6000 |
| NCI-N87 | 6000 |
| NUGC-4 10cE8 | 3000 |
| NUGC-4 10cF7-5 sort3a | 3000 |
| BxPC-3~CLDN18.2 | 3000 |
| HEK293~CLDN18.2 | 2000 |
| HEK293~CLDN18.1 | 2000 |
| HEK293(CLDN6) | 2000 |

Cell viability was analyzed using the AppliChem®Cell proliferation Kit II (AppliChem®, A8088, 1000) according to the manufacturer's instructions. After 3-5 h incubation with XTT reagent, the absorbance at 480 nm was measured (reference 630 nm) using a spectrophotometer (Tecan). Reduction of viability was calculated using the following equation:

$$\text{Reduction of viability [\%]} = 100 - \left[\frac{\text{sample} - \text{blank}}{\text{control} - \text{blank}} * 100\right]$$

blank: medium control
control: cells without antibody
sample: cells with antibody The EC50 values were determined with GraphPad Prism 6 using non-linear regression.

7. Bystander Assay

The bystander activity of toxin-conjugated IMAB362 antibodies on target negative cells was analyzed in vitro by co-culturing the CLDN18.2 negative, luciferase expressing cell line PA-1 (Luc) in the presence or absence of the CLDN18.2 positive cell line NUGC-4 10cE8. Therefore, $1.5 \times 10^3$ PA-1 (Luc) cells per well were seeded for single culture or together with $1.5 \times 10^3$ NUGC-4 10cE8 cells per well for co-culture in RPMI medium supplemented with 10% FCS and 1% pen/strep. After 24 h, IMAB362-DM4, IMAB362-vcMMAE or unconjugated IMAB362 as negative control were added and cells were cultured for another 72 h. Cell viability was analyzed as described in 6. Lysis of target negative cells was determined by measuring the bioluminescence of luciferase expressing PA-1 (Luc) cells. Therefore, 50 µl luciferin mix (1.92 mg/ml D-luciferin (Sigma®, 50227) and 160 mM HEPES in ddH$_2$O) were added per well. The plate was incubated in the dark at RT for 90 min and bioluminescence was measured using a luminometer (Infinite® M200, TECAN). Results are expressed as integrated digital relative light units (RLU). Reduction of viability was calculated as described in 6.

8. Animal Experiments

All xenograft studies were carried out in compliance with the national regulations and ethical guidelines for experimental animal studies. All animals were maintained under specific pathogen-free conditions in individual ventilated cages and under a 12 h artificial light-dark cycle. Food and water was provided ad libitum. Before start of studies mice were allowed to acclimate for a minimum of 6 days.

8.1. Maximum Tolerated Dose (MTD) Study

Xenograft tumors were inoculated by subcutaneous injection of $8.5 \times 10^6$ BxPC-3~CLDN18.2 human pancreatic tumor cells in 200 µl PBS into the flanks of female Hsd:Athymic Nude-Foxn1nu mice. To determine MTD and efficacy of anti-CLDN18.2 antibody drug conjugates, tumor-bearing mice received different doses of IMAB362-DM4 or IMAB362-vcMMAE. The maximal applicable dose was limited by the antibody concentration and the injection volume recommended from GV-SOLAS for intravenous injection in mice (~200 µl). Both antibodies were applied in the maximal concentration as single and repeated dose (i.e. 15 and 16 mg/kg, respectively) as well as half of this concentration (i.e. 7.5 and 8 mg/kg respectively) or vehicle control (group size: n=5). Antibodies were injected intravenously on day 14 post graft and for repeated dose additionally on day 21 post graft. Body weight, animal health, behavior and tumor size were monitored twice a week with a caliper and tumor volumes were calculated according to the following formula: [length×width×(width/2)]. All animals were dissected when the first tumor of the vehicle group reached a maximum of 1400 mm$^3$ or when the tumor became ulcerous (day 49 post graft for IMAB362-DM4, day 37 post graft for IMAB362-vcMMAE). Blood samples for clinical chemistry were collected under general anesthesia initiated with 250 µl i.p. of a mixture consisting of 1.25 ml ketamine, 1 ml xylazine (2%) and 7.75 ml H$_2$O. Subsequently, mice were perfused with PBS followed by a perfusion with 4% formalin under general anesthesia. Selected organs and tissues (stomach, esophagus, brain, heart, kidney, liver, lung, pancreas, spleen, duodenum, ileum, colon, uterus and ovaries) were dissected and fixed in 4% formalin, stored at 4° C. and finally paraffin embedded. Three-micrometer tissue sections were cut from each FFPE (formalin fixated paraffin embedded) sample and mounted on adhesive slides (SuperFrost® Ultra Plus, Thermo Fisher Scientific). After baking for 60 min at 58° C. the FFPE tissue sections were deparaffinized using xylene and rehydrated through a graded ethanol series (2×100%, 2×96%, 2×70% ethanol for 3 min each). Nuclei were stained with for 5 min at RT with Mayer's hematoxyline, followed by blueing in tap H$_2$O. Subsequently the cytoplasm was counterstained with aqueous 0.5% eosin for 2 min at RT. After dehydration through a graded ethanol series and xylene sections were mounted using non-aqueous mounting media X-TRA Kit.

8.2. Clinical Biochemistry

To test for possible organ toxicity, relevant markers for pancreas-, nephron- and hepatotoxicity were analyzed in serum samples.

Levels of alanine aminotransferase/glutamic-pyruvic transaminase (GPT), aspartate aminotransferase/glutamic-oxaloacetic transaminase (GOT), gamma-glutamyltransferase (gamma-GT), alkaline phosphatase (AP), glutamate dehydrogenase (GLDH), creatinine, creatinine kinase (CK), urea, cholinesterase, bilirubin, lipase, alpha-amylase, lactate dehydrogenase (LDH), albumin and total protein were determined at the Universitätsmedizin der Johannes Gutenberg Universität (Mainz, Germany). Serum samples were prepared from blood obtained after final bleeding. Blood was collected by retrobulbar venipuncture after mice were anesthetized with ketamin/xylazine.

8.3. Efficacy Studies

For establishing human xenograft tumors an appropriate number of cells were suspended in a volume of 200 µl PBS and were injected subcutaneously into the flank of female Hsd:Athymic Nude-Foxn1nu mice. Tumor bearing mice were treated with a single intravenous injection of IMAB362-DM4 or IMAB362-vcMMAE at doses not exceeding the MTD. The naked antibody control was administered semi-weekly by alternating IV/i.p. injections of ~8 mg/kg IMAB362. In early treatment studies, treatment was initiated 3 days post graft. In advanced treatment studies, tumors were grown to a volume between 50 and 200 mm$^3$ and mice were redistributed into control and antibody groups with homogenous tumor mean volumes before treatment. Body weight, animal health, behavior and tumor size were monitored semi-weekly with a caliper. Tumor volumes were calculated by the following formula: [length×width× (width/2)]. An abort criterion was a tumor size with >16 mm in length or width or with a calculated volume of >1400 mm³. Further abort criterions were ulcerating tumors or when the animal lost more than 10% body weight. In case of complete tumor growth inhibition, mice were observed for 120 days after treatment. Persisting tumors were prepared and fixated in 4% formalin for subsequent IHC studies.

9. Antibody-Dependent Cellular Cytotoxicity (ADCC)

Antibody-dependent cellular cytotoxicity (ADCC) was determined by measuring the content of intracellular ATP in non-lysed cells after the addition of human PBMCs to the target cells in presence of IMAB362 toxin-conjugates. Luciferase-generated bioluminescence was used for quantification of ATP.

NUGC-4 10cF7_5 sort3a p3151 #10 target cells were seeded with defined cell numbers ($8\times10^6$ cells) two days before the assay to obtain reproducible confluences.

Target cells were harvested with 0.05% Trypsin/EDTA (Gibco®, 25300-054) and adjusted to a concentration of $1.6\times10^5$ cells/ml in growth medium containing 20 mM HEPES (Gibco®, 15630-056). $8\times10^3$ cells per well were seeded into a white 96-well PP-plate and incubated for ~5 h at 37° C. and 5% $CO_2$.

PBMCs were prepared from fresh buffy coats obtained from healthy donors. About 20-25 ml blood was diluted (1:2) with PBS in 3 Falcon™ tubes and carefully layered onto 15 ml Ficoll-Paque® PLUS (GE Healthcare, 17144003) in four 50 ml Falcon™ tubes. Gradients were centrifuged (25 min, 700× g, w/o brakes). After centrifugation PBMC were collected from the interphase, washed in 50 ml PBS/2 mM EDTA, centrifuged (5 min, 468× g), again resuspended in 50 ml PBS/2 mM EDTA and centrifuged again (10 min, 208× g) to remove platelets. Pellets were resuspended in 50 ml PBS/2 mM EDTA and cells were counted. Subsequently, PBMCs were centrifuged (5 min, 468× g), resuspended in X-VIVO™ 15 culture medium (Lonza, BE04-418Q) containing 5% human serum and cultured for 1.5 h at 37° C., 5% $CO_2$. PBMCs were harvested, centrifuged (5 min, 468×g) and resuspended in X-VIVO™ 15 culture medium (Lonza®, BE04-418Q) adjusting the cell concentration (for an E:T ratio of 40:1) to $1.28\times10^7$ cells/ml. IMAB362-DM4, IMAB362-vcMMAE and IMAB362 were serially diluted (4.5 fold dilution steps) 11 times resulting in a concentration range between 160 μg/ml and 0.05 ng/ml (final concentration of 40 μg/ml to 0.01 ng/ml). 25 μl of each dilution was added to the target cells and for each condition quadruplicates were used. PBS without antibodies was added to the medium and total lysis control wells. Subsequently, 25 μl of the prepared PBMCs ($3.2\times10^5$ cells) were added to each well to achieve an E:T ratio of 40:1 and plates were incubated for 15 h+1 h at 37° C., 5% $CO_2$. After the overnight incubation, 10 μl 8% Triton™ X-100/PBS solution was added to the maximum lysis control wells and 10 μl PBS to the other wells. Finally, 50 μl freshly prepared luciferin stock solution was added (160 mM HEPES, 1x PBS, 3.84 mg/ml D-Luciferin (Sigma Aldrich, 50227)) to each well and plates were incubated for 90 min at RT in the dark. Bioluminescence was measured using a luminometer (Infinite® M200, TECAN). Results are expressed as integrated digital relative light units (RLU).

The specific lysis is calculated as:

$$\text{specific lysis } [\%] = 100 - \left[\frac{(\text{sample} - \text{total lysis})}{(\text{max viable cells} - \text{total lysis})} \times 100\right]$$

(max viable cells: 10 μl PBS, without antibody; total lysis: 10 μl 8% (v/v) Triton™ X-100 in PBS, without antibody)

All ADCC data were processed with GraphPad Prism® 6 using the "log(agonist) vs response-find EC anything" function. Maximal lysis was defined as span (difference top to bottom) of the dose response curve, but maximum 100%.

10. Complement-Dependent Cytotoxicity (CDC)

Complement-dependent cytotoxicity (CDC) was determined by measuring the content of intracellular ATP in non-lysed cells after the addition of human complement to target cells in the presence of IMAB362 toxin-conjugates. As readout the ATP-dependent bioluminescence generated by luciferase was measured.

NUGC-4 10cF7_5 sort3a p3151 #10 or KATO-III FGF-BP #12 adM p3151 #25 target cells were seeded with defined cell numbers ($8\times10^6$ and $9\times10^6$ cells, respectively) two days before the assay to obtain reproducible confluences.

Target cells were harvested with 0.05% Trypsin/EDTA and adjusted to a concentration of $1.6\times10^5$ cells/ml in their respective culture medium containing 10% (v/v) FCS. $8\times10^3$ cells were seeded into a white 96-well plate and incubated at 37° C. and 5% $CO_2$. After 24 h, 50 μl antibodies serially diluted in assay medium (60% RPMI, containing 20 mM HEPES; 40% human serum, pooled from several healthy donors) were added (final concentration 80 μg/ml to 78.13 ng/ml) and cells were incubated for 80 min at 37° C. and 5% $CO_2$. Subsequently, 10 μl 8% (v/v) Triton™ X-100 in PBS were added to the total lysis controls, whereas 10 μl PBS were added to all other wells (max viable cells controls and the actual samples). Luciferase reaction was started by adding 50 μl luciferin mix (3.84 mg/ml D-luciferin, 160 mM HEPES in dd$H_2$O) per well. The plate was kept in the dark at RT for 90 min and bioluminescence was measured using a luminometer (Infinite® M200, TECAN). Results are expressed as integrated digital relative light units (RLU).

The specific lysis is calculated as:

$$\text{specific lysis } [\%] = 100 - \left[\frac{(\text{sample} - \text{total lysis})}{(\text{max viable cells} - \text{total lysis})} \times 100\right]$$

(max viable cells: 10 μl PBS, without antibody; total lysis: 10 μl 8% (v/v) Triton™ X-100 in PBS, without antibody)

All CDC data were processed with GraphPad® 6 using the "log(agonist) vs response—find EC anything" function. Maximal lysis was defined as span (difference top to bottom) of the dose response curve, but maximum 100%.

Example 2: Endocytosis Screening of Anti-CLDN18.2 Specific Antibodies

While in tumor therapy with naked antibodies, the internalization of target bound antibodies can reduce the number of membrane bound antibodies accessible for the mayor mode of actions, e.g. ADCC and CDC, endocytosis is an essential feature for the development of antibody-drug conjugates (ADC). One important property of the ADCs is the endocytosis of the target-ADC complex. Therefore, the endocytosis rate of the naked antibody is one of the essential key factors for the development of toxin-conjugated antibodies.

Binding properties, i.e. relative affinity to CLDN18.2, cross-reactivity to CLDN18.1 and antigenic epitope mediating CLDN18.2 specificity, were determined for different murine and chimeric anti-CLDN18.2 antibodies by flow cytometric analysis (Table 5 and Table 6). Antibodies demonstrating high binding to CLDN18.2 were selected for further endocytosis screening.

The efficiency of endocytosis of different CLDN18.2 specific and CLDN18.2/CLDN18.1 reactive antibodies was tested in vitro by co-incubating the antibodies with saporin conjugated Fab fragments (Fab-ZAP) together with CLDN18.2 expressing HEK293-CLDN18.2 cells. Upon co-internalization with the target bound antibody, saporin inhibits the protein biosynthesis of the cell resulting in cell death which can be monitored by a cell viability assay. This method is an indirect way to assess the endocytosis of the target-antibody complex. Antibodies were tested as chimeric antibodies when available, otherwise endocytosis screening was performed with murine antibodies.

Figure 2:
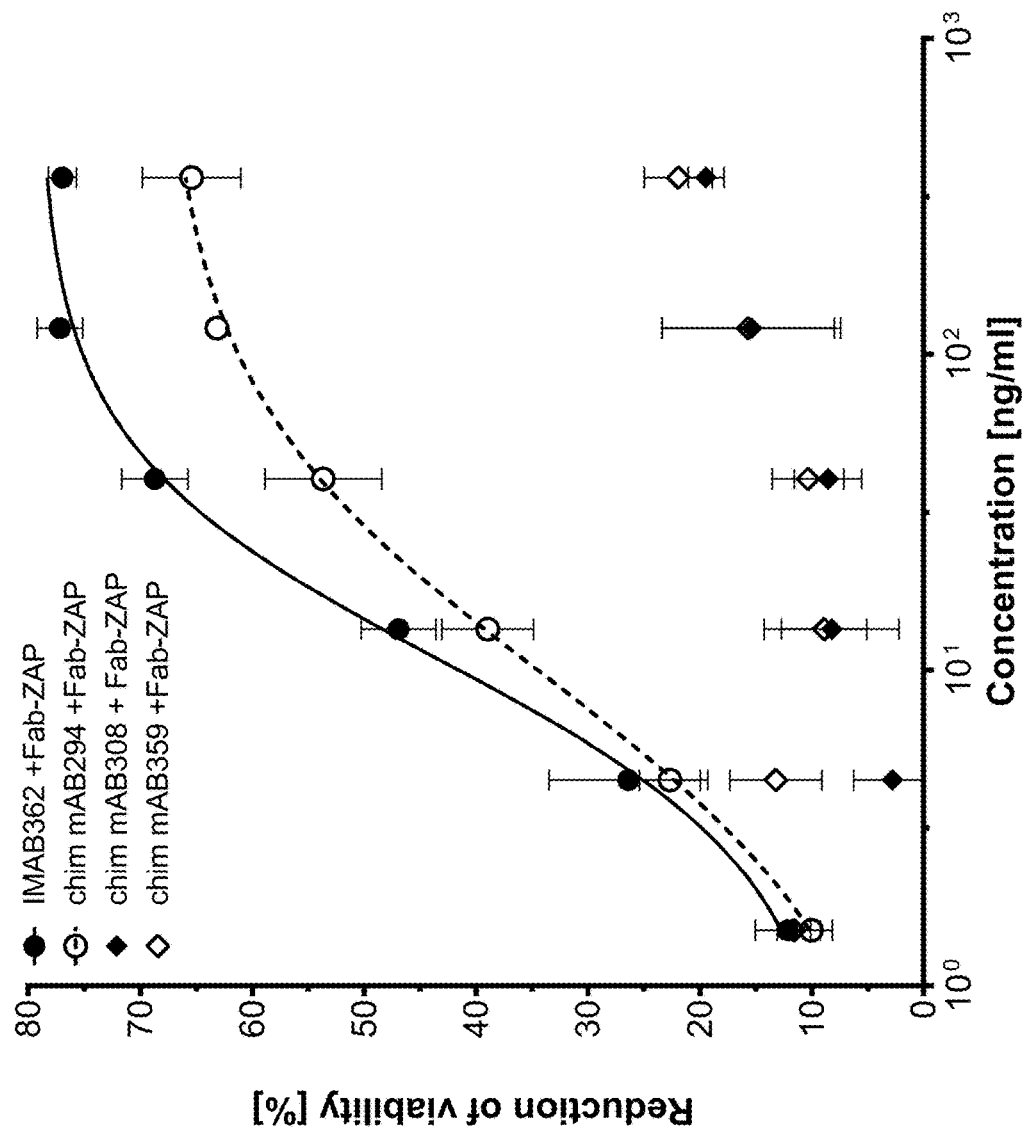
FIG. 2: Reduction of viability after co-incubation of HEK293~CLDN18.2 cells with chimeric anti-CLDN18.2 mAbs and Fab-ZAP (indirect evaluation of internalization).

The chim mAb362 (IMAB362) as well as chim mAB294 can be efficiently internalized upon CLDN18.2 binding, leading to a reduction of HEK293-CLDN18.2 cell viability even at very low antibody concentrations (IMAB362: EC50=11 ng/ml; chim mAB294: EC50=10 ng/ml). In contrast, chim mAB308 and chim mAB359 did not reduce cell viability (FIG. 2). As chim mAB294 and chim mAB359 exhibiting similar relative binding affinities and show considerable discrepancies in internalization (chim mAB294: EC50=10 ng/ml; chim mAB359: no endocytosis), the efficiency of endocytosis seems not only to correlate with antibody binding affinity but also to be dependent on the binding epitope.

Even the internalization of mu mAB362 was superior to all other tested murine CLDN18.2 reactive antibodies which did not reveal substantial endocytosis in Fab-Zap assay (FIG. 3).

In summary, the CLDN18.2 specific antibodies IMAB362 and chim mAB294 were efficiently internalized upon binding to CLDN18.2 and are suitable for the further evaluation as antibody drug conjugates.

TABLE 5

Relative binding affinity and specificity of CLDN18.2 reactive antibodies.

| Antibody | Isotype | EC50 [ng/ml] | EC50 normalized [%] | Max. binding [MFI] | Max. binding normalized [%] | CLDN18.1 reactive | Identified amino acids of human CLDN18.2 recognized by the antibodies |
|---|---|---|---|---|---|---|---|
| IMAB362[1] | human IgG1 | 520 | 100 | 15797 | 100 | No | A42S, N45Q, E56Q |
| IMAB362[2] | | 584 | 100 | 18496 | 100 | | |
| IMAB362[3] | | 652 | 100 | 7952 | 100 | | |
| IMAB362[4] | | 1242 | 100 | 5319 | 100 | | |
| mu mAB362[3] | mouse IgG1 | 2238 | 343 | 8826 | 111 | | A42S, N45Q, E56Q |
| mu mAB362[4] | | 4286 | 345 | 5913 | 111 | | |
| mu mAB362[4] | mouse IgG2a | 654 | 53 | 4880 | 92 | | n.a. |
| mu mAB359[3] | mouse IgG2b | 4474 | 686 | 4297 | 54 | No | n.a. |
| mu mAB325[3] | mouse IgG1 | 33263 | 5102 | 3672 | 46 | No | A42S, E56Q, G65P, L69I |
| mu mAB62[3] | mouse IgG2a | 27932 | 4284 | 2800 | 35 | No | n.a. |
| mu mAB187[3] | mouse IgG2a | 26597 | 4079 | 2428 | 31 | No | N37D, N45Q, Q47E |
| mu mAB294[3] | mouse IgG2a | 348 | 53 | 989 | 12 | No | A42S, E56Q |
| mu mAB370[1] | mouse IgG2a | 7877 | 1514 | 1405 | 9 | No | n.a. |
| mu mAB330[2] | mouse IgG3 | 11054 | 1894 | 1707 | 9 | No | n.a. |
| mu mAB374[1] | mouse IgG2a | 8262 | 1588 | 468 | 3 | No | n.a. |
| mu mAB385[1] | mouse IgG1 | 8534 | 1640 | 471 | 3 | No | A42S, N45Q, E56Q, G65P, L69I |
| mu mAB177[3] | mouse IgG1 | 50 | 8 | 136 | 2 | No | N37D, A42S, N45Q, Q47E, E56Q, L69I |
| mu mAB55[3] | mouse IgG2a | 1945 | 298 | 241 | 3 | n.a. | A42S, N45Q, E56Q, G65P, L69I |
| mu mAB317[3] | mouse IgG1 | 41 | 6 | 106 | 1 | No | Q29M, A42S, N45Q, Q47E, E56Q, G65P, L69I |
| mu mAB279[3] | mouse IgG2a | 27 | 4 | 118 | 1 | No | n.a. |
| mu mAB363[3] | mouse IgG1 | 15405 | 2363 | 877 | 11 | Yes | N37D |
| mu mAB360[1] | mouse IgG2a | 19319 | 3713 | 1405 | 9 | Yes | n.a. |
| mu mAB371[1] | mouse IgG1 | 11361 | 2184 | 747 | 5 | Yes | — |
| mu mAB382[2] | mouse IgG2b | 12424 | 2129 | 842 | 5 | Yes | — |
| mu mAB348[2] | mouse IgG2a | 13573 | 2326 | 703 | 4 | Yes | — |
| mu mAB322[2] | mouse IgG2a | 12770 | 2189 | 818 | 4 | Yes | — |
| mu mAB321[2] | mouse IgG2a | 8082 | 1385 | 505 | 3 | Yes | n.a. |
| mu mAB339[1] | mouse IgG2a | 608 | 117 | 180 | 1 | Yes | n.a. |
| mu mAB338[2] | mouse IgG1 | 3966 | 680 | 244 | 1 | Yes | N37D |

Binding to CLDN18.2 (EC50 normalized [%] and max. binding normalized [%] are normalized to IMAB362) and CLDN18.1 reactivity were determined by flow cytometry on HEK293 cells stably expressing the respective protein.
The antigenic epitope responsible for CLDN18.2 specificity was analyzed by flow cytometry on HEK293T cells transiently overexpressing the corresponding CLDN18.2 mutant.
n.a.: not analyzed.
Antibodies marked with the same number (1, 2, 3 or 4) were tested in the same binding assay.
[1-3]detection with APC-conjugated secondary antibody;
[4]detection with ProteinL-FITC;
n.a:. not analyzed.

TABLE 6

Relative binding affinity and endocytosis of CLDN18.2 specific antibodies.

| | Binding | | | | Cell viability | | | Identified amino |
|---|---|---|---|---|---|---|---|---|
| | | EC50 | | Max. binding | | | Max. viability reduction | acids of human CLDN18.2 |
| Antibody | EC50 [ng/ml] | normalized [%] | Max. binding [MFI] | normalized [%] | EC50 [ng/ml] | EC50 [%] | normalized [%] | recognized by the antibodies |
| IMAB362[1] | 584 | 100 | 18496 | 100 | 11 | 100 | 100 | A42S, N45Q, E56Q |
| IMAB362[2] | 1242 | 100 | 5319 | 100 | | | | |
| IMAB362[3] | | | | | 13 | 100 | 100 | |
| mu muAB362[3] (IgG2a) | 4286 | 345 | 5913 | 111 | ~30 | 231 | 66 | n.a. |
| mu muAB362[3] (IgG1) | 654 | 53 | 4880 | 92 | 2.2 | 17 | 66 | A42S, N45Q, E56Q |
| chim mAB294[2] | 5701 | 459 | 3089 | 58 | 10 | 91 | 86 | A42S, N45Q, E56Q |
| chim mAB359[1] | 2752 | 472 | 11618 | 63 | no effect | no effect | no effect | A42S, N45Q, E56Q |
| chim mAB308[1] | 18883 | 3236 | 15016 | 81 | no effect | no effect | no effect | N37D, A42S, E56Q |
| chim mAB62[1] | 32313 | 5538 | 4079 | 22 | no effect | no effect | no effect | n.a. |
| chim mAB279[1] | 60046 | 10291 | 4394 | 24 | no effect | no effect | no effect | n.a. |

Relative binding affinity [%], max. binding [%] or max. viability reduction [%] normalized to IMAB362 are shown for binding and endocytosis using flow cytometry and Fab-ZAP assay, respectively.
Antibodies marked with the same number (1 or 2) were tested in the same binding assay.
Indirect assessment of internalization with antibodies marked with 1 or 2 were performed together in one and with antibodies marked with 3 in a second cell viability assay.
[1] detection with APC-conjugated secondary antibody;
[2] and [3] detection with ProteinL-FITC.

Example 3: Toxin-Conjugation of IMAB362

Piramal Healthcare performed the toxin conjugation including final buffer exchange. Stability studies were performed to show that the ADCs remain within specification during a certain period if stored under defined storage conditions. IMAB362 was conjugated to MMAE via the cleavable valine-citrulline linker (vc linker) or to DM4 via the cleavable N-succinimidyl-4-(2-pyridyldithio)butyrate linker (SPDB linker). The IMAB362 toxin conjugates were stored in storage buffer (20 mM histidine and 85 mg/ml sucrose, pH 5.8) at 2-8° C.

TABLE 7

28-day stability testing of IMAB362-DM4 and IMAB362-vcMMAE.

| | Result | | | |
|---|---|---|---|---|
| | IMAB362-DM4 | | IMAB362-vcMMAE | |
| Analysis | Day 1 | Day 28 | Day 1 | Day 28 |
| DAR | 3.2 | 3.2 | 4.5 | 4.0 |
| Monomer [%] | 96 | 95 | 95 | 93 |
| Free drug [%] | 0.4 | 1.0 | not detected | 0.3 |

DAR: drug antibody ratio

IMAB362-DM4 and IMAB362-vcMMAE both demonstrate a high monomer content of ≥95% and only low amounts of free drug (≤1%). The 28-day stability testing of toxin-conjugated IMAB362 antibodies at a storage temperature of 2-8° C. show only a small decrease of the monomer content and a low increase in free drug for both ADCs. Both antibodies were efficiently conjugated and exhibit a drug to antibody ratio of 3.2 for IMAB362-DM4 and 4.5 for IMAB362-vcMMAE (Table 7).

Example 4: Binding of IMAB362-ADCS

The binding properties of IMAB362 have been tested in detail before:
- IMAB362 binds to the first extracellular loop of claudin 18 splice variant 2 (CLDN18.2).
- Affinity to CLDN18.2 is in the low nanomolar range.
- No cross-reactivity with any CLDN18.2 negative cell or tissue type was observed.
- No cross-reactivity with the closest related family member claudin 18 splice variant-1 (CLDN18.1).

The relative binding affinities of DM4- and MMAE-conjugated IMAB362 antibodies were compared with unconjugated IMAB362 by flow cytometry using cell lines endogenously and ectopically expressing CLDN18.2. Binding properties were tested at different antibody concentrations in a range of 0.1 to 20 μg/ml (FIG. 4, Table 8).

TABLE 8

Overview of binding assays performed with IMAB362-toxin conjugates on CLDN18.2 positive cell lines.

| | IMAB362 | | IMAB362-DM4 | | IMAB362-vcMMAE | |
|---|---|---|---|---|---|---|
| Cell line | Bmax [MFI] | EC50 [ng/ml] | Bmax [MFI] | EC50 [ng/ml] | Bmax [MFI] | EC50 [ng/ml] |
| HEK293~mock | — | — | — | — | — | — |
| HEK293~CLDN18.2 | 18318 | 1121 | 19481 | 1472 | 14159 | 1594 |
| HEK293~CLDN18.1 | — | — | — | — | — | — |
| DAN-G 1C5F2 | — | — | — | — | — | — |
| NCI-N87 | — | — | — | — | — | — |
| NCI-N87~CLDN18.2 | 33678 | 310 | 28605 | 274 | 16569 | 103 |

TABLE 8-continued

Overview of binding assays performed with IMAB362-
toxin conjugates on CLDN18.2 positive cell lines.

|  | IMAB362 | | IMAB362-DM4 | | IMAB362-vcMMAE | |
| --- | --- | --- | --- | --- | --- | --- |
| Cell line | Bmax [MFI] | EC50 [ng/ml] | Bmax [MFI] | EC50 [ng/ml] | Bmax [MFI] | EC50 [ng/ml] |
| NUGC-4 10cF7-5 sort 3a | 67484 | 1671 | 77500 | 2600 | 68009 | 2520 |
|  | 54277 | 2384 | 69633 | 3909 | 45597 | 4049 |
| NUGC-4 10cE8 | 34805 | 1570 | 35799 | 3046 | 29103 | 2826 |
|  | 28336 | 3673 | 36049 | 7487 | 25785 | 5464 |
| BxPC-3~CLDN18.2 | 51380 | 104 | 76629 | 507 | 47197 | 183 |
|  | 28664 | 113 | 35700 | 425 | 25404 | 261 |

Bmax: maximum binding,
MFI: mean fluorescence intensity

Compared with unconjugated IMAB362, DM4- and MMAE-conjugated IMAB362 showed slightly reduced relative binding affinities on cells endogenously and ectopically expressing CLDN18.2 (FIG. 4, Table 8). Both toxin-conjugated antibodies had very similar EC50 values, but slightly different maximum binding values in which IMAB362-DM4 exhibited higher maximum binding (Table 8).

CLDN18.2-mediated binding of IMAB362-toxin conjugated antibodies was tested on ectopically CLDN18.2 overexpressing cells and on the corresponding CLDN18.2 negative parental cell lines (FIG. 5, Table 8).

Binding of IMAB362-DM4 and IMAB362-vcMMAE strictly depends on the presence of its target molecule CLDN18.2 (FIG. 5). The binding specificity was analyzed by flow cytometry using HEK293 transfectants engineered to overexpress human CLDN18.2 or the highly homologous protein human CLDN18.1. HEK293~mock cells were used as negative controls (FIG. 6, Table 8).

IMAB362 and the toxin-conjugated antibodies IMAB362-DM4 and IMAB362-vcMMAE bound with similar relative affinities to HEK293~CLDN18.2 cells ectopically expressing human CLDN18.2 (Table 8). Moreover, IMAB362, DM4- and MMAE-conjugated IMAB362 did not show cross-reactivity to human CLDN18.1 or mock transfected cells (FIGS. 6B and C).

Example 5: Efficacy and Specificity of IMAB362-ADCS In Vitro

1. Influence on Cell Viability

The influence of IMAB362-DM4 and IMAB362-vcMMAE on cell viability was tested with several human gastric and pancreatic cancer cell lines endogenously and ectopically expressing CLDN18.2 using a colorimetric XTT-based assay for the spectrophotometric quantification of metabolically active cells. The anti-tumoral activities were tested at different antibody concentrations in a range of 3 to 16875 ng/ml (FIG. 7, Table 9).

IMAB362-DM4 and IMAB362-vcMMAE efficiently inhibited the viability of the gastric cancer cell line NUGC-4, NCI-N87~CLDN18.2 and the pancreatic cell line BxPC-3~CLDN18.2 in vitro (FIG. 7). Both IMAB362-toxin conjugates inhibited cell viabilities of endogenously CLDN18.2 expressing NUGC-4 cells (EC50 values: 155-631 ng/ml, maximum reduction of viability: ≥85%) and ectopically CLDN18.2 expressing BxPC-3~CLDN18.2 cells (EC50 values: 43-54 ng/ml, maximum reduction of viability: ≥83%) and NCI-N87~CLDN18.2 cells (EC50 values: 75-180 ng/ml, maximum reduction of viability: 45-61%) at similar concentrations (FIG. 7, Table 9).

TABLE 9

Overview of cell viability assays performed with IMAB362-
toxin conjugates on CLDN18.2 positive cell lines.

|  | IMAB362-DM4 | | IMAB362-vcMMAE | |
| --- | --- | --- | --- | --- |
| Cell line | EC50 [ng/ml] | Reduction viability [%] | EC50 [ng/ml] | Reduction viability [%] |
| NCI-N87~CLDN18.2 | 75 | 49 | 100 | 45 |
|  | 108 | 61 | 180 | 56 |
| NUGC-4 10cF7-5 sort 3a | 155 | 88 | 338 | 86 |
| NUGC-4 10cE8 | 372 | 69 | 631 | 67 |
| BxPC-3~CLDN18.2 | 43 | 83 | 48 | 86 |
|  | 54 | 87 | 43 | 84 |

In addition, the target-mediated anti-tumoral activity of an IMAB362-toxin conjugate was tested in vitro using the NCI-N87 CLDN18.2 negative cell line and the stably transfected NCI-N87~CLDN18.2 cell line (FIG. 8). IMAB362-vcMMAE inhibited cell viability only on CLDN18.2 positive but not on CLDN18.2 negative cells. Therefore, the activity of IMAB362-vcMMAE strictly depends on CLDN18.2 expression (FIG. 8).

The specificity of toxin-conjugated IMAB362 antibodies was analyzed using HEK293 transfectants overexpressing human CLDN18.2 or the highly homologous protein human CLDN18.1. HEK293 cells stably transfected with the empty vector were used as negative controls (FIG. 9). IMAB362-vcMMAE reduces cell viability on CLDN18.2 positive but not on CLDN18.2 negative cells. The effect is strictly CLDN18.2 specific because no inhibition of cell proliferation could be observed on cells expressing the homologous protein 18.1 (FIG. 9).

In summary, IMAB362-vcMMAE and IMAB362-DM4 showed similar efficacies in vitro and both ADCs highly efficiently inhibited cell viability of several human gastric and pancreatic cancer cell lines. The effect strictly depends on target expression.

2. Bystander Effect

The bystander activity of IMAB362-DM4 and IMAB362-vcMMAE in vitro was determined using mixed tumor cell cultures consisting of CLDN18.2 positive and negative cell lines. Target-negative PA-1 (Luc) cells stably expressing firefly luciferase were used as reporter cells to measure cell lysis.

Luciferase activity of co-cultures of luciferase expressing PA-1 (Luc) and luciferase negative NUGC-4 cells showed that treatment with IMAB362-DM4 or IMAB362-vcMMAE eliminated target negative PA-1 (Luc) cells very effectively in the presence of target positive NUGC-4 cells. Moreover, PA-1 (Luc) cells were unaffected in the absence of CLDN18.2 expressing cells (FIG. 10).

In summary, IMAB362-DM4 and IMAB362-vcMMAE ADCs were able to induce a bystander effect on neighboring CLDN18.2-negative tumor cells. Both toxins were efficiently released from IMAB362 within CLDN18.2 positive cancer cells and, due to their membrane permeability, are able to exert cytotoxic activity on bystander cells.

Example 6: Anti-Tumoral Efficacy of IMAB362-ADCS In Vivo

1. Maximum Tolerated Dose Studies

In a first in vivo experiment, the maximum tolerated dose (MTD) of IMAB362-DM4 and IMAB362-vcMMAE was determined in nude mice with advanced human BxPC-3~CLDN18.2 pancreatic xenograft tumors. The MTD refers to the highest dose in a treatment that will produce the desired effect without unacceptable toxicity.

1.1. MTD of IMAB362-DM4

BxPC-3~CLDN8.2 cells ectopically expressing human CLDN18.2 were injected subcutaneously into the flank of female Hsd:Athymic Nude-Foxn1nu mice. After the tumors reached an average size of 75±13 mm$^3$ (mean±SD) on day 13, mice were grouped into control and antibody groups. Mice received a single dose of 7.5 or 15 mg/kg IMAB362-DM4 by IV bolus injection on day 14 or repeated doses of 15 mg/kg IMAB362-DM4 by IV bolus injections on day 14 and day 21, respectively. Mice of the control group got vehicle on day 14. On day 49 after engraftment, animals were sacrificed. To test for toxicity, blood samples were collected and organs were prepared and stored for further histopathological studies.

Tumor Growth:

IMAB362-DM4 inhibited tumor growth in mice with advanced human BxPC-3~CLDN8.2 xenograft tumors. IMAB362-DM4 single or repeated treatments resulted in nearly complete tumor regressions in all treated mice during the observation period of the study (49 days), independently of the dose. Thus, a single dose of 7.5 mg/kg IMAB362-DM4 might be sufficient for complete tumor remission (FIG. 11).

Health status:

Bodyweight, animal behavior and general health status were monitored twice a week. All animals showed normal body weight throughout the experiments (FIG. 12). No behavioral abnormalities were observed. However, one animal died after intravenous application of the second dose of 15 mg/kg IMAB362-DM4 for unknown reason.

Clinical chemistry:

We determined serum levels of alanine transaminase (GPT), aspartate transaminase (GOT), glutamate dehydrogenase (GLDH) alkaline phosphatase (AP), α-amylase, cholinesterase, creatinine kinase (CK), lactate dehydrogenase (LDH), lipase, urea, glucose, total protein and albumin. No differences between the vehicle and the IMAB362-DM4 groups were detected (FIG. 13). Creatinine and gamma-glutamyl transferase were below the detection limit in all groups (data not shown). All animals in all groups showed normal serum levels of tested surrogate markers for hepato-, nephron- or pancreatic toxicity even after repeated doses of 15 mg/kg IMAB362-DM4.

In summary, 15 mg/kg IMAB362-DM4 (equivalent to 45 mg/m$^2$ in human) as single administration were well tolerated in mice and demonstrated high anti-tumoral efficacy in the treatment of CLDN18.2 positive xenografts. Due to limitations of concentration and injection volume the intravenous injection of higher doses was not feasible and the maximum tolerated single dose could not be determined.

Histological Analysis:

For histological analysis, paraffin sections from brain, heart, kidney, liver lung, pancreas, spleen and stomach were hematoxylin-eosin stained and microscopically examined for IMAB362-vcMMAE mediated morphological changes. No morphological changes could be observed in tissue sections from IMAB362-DM4 treated animals compared to vehicle treated mice. Notably, stomach, the only tissue expressing murine Cldn18.2 did not demonstrate antibody therapy mediated tissue damage (FIG. 14).

1.2. MTD of IMAB362-vcMMAE

The MTD of IMAB362-vcMMAE was tested using the same mouse model as for IMAB362-DM4 (1.1). Mice were grouped after the tumors reached an average size of 111±27 mm$^3$ (mean±SD) on day 13 and treated with a single IV bolus injection of 8 or 16 mg/kg IMAB362-vcMMAE (equivalent to 24 and 48 mg/m$^2$ in human) on day 14 or with repeated doses IV bolus injections of 16 mg/kg IMAB362-vcMMAE on days 14 and 21. Mice of the control group received vehicle control on day 14. Animals were sacrificed on day 37. Clinical biochemistry was determined and organs were collected and stored for further histopathological studies.

Tumor Growth:

IMAB362-vcMMAE treatment induced tumor regression and further inhibited tumor growth in mice with advanced human BxPC-3~CLDN8.2 xenograft tumors. At the end of the study (37 days), IMAB362-vcMMAE single or repeated treatments resulted in nearly complete tumor regressions in all treated mice, independently of the dose. Thus, a single dose of 8 mg/kg IMAB362-vcMMAE might be sufficient for complete tumor remission (FIG. 15).

Health Status:

Bodyweight, animal behavior and general health status were monitored twice a week. All animals showed normal body weight throughout the experiments (FIG. 16). Two animals (one mouse from the SD and the RD group) were apathetic for a short time directly after the first injection of 16 mg/kg IMAB362-vcMMAE. However, this abnormal behavior was not observed in any other animal or after the second application of IMAB362-vcMMAE.

Figure 17:
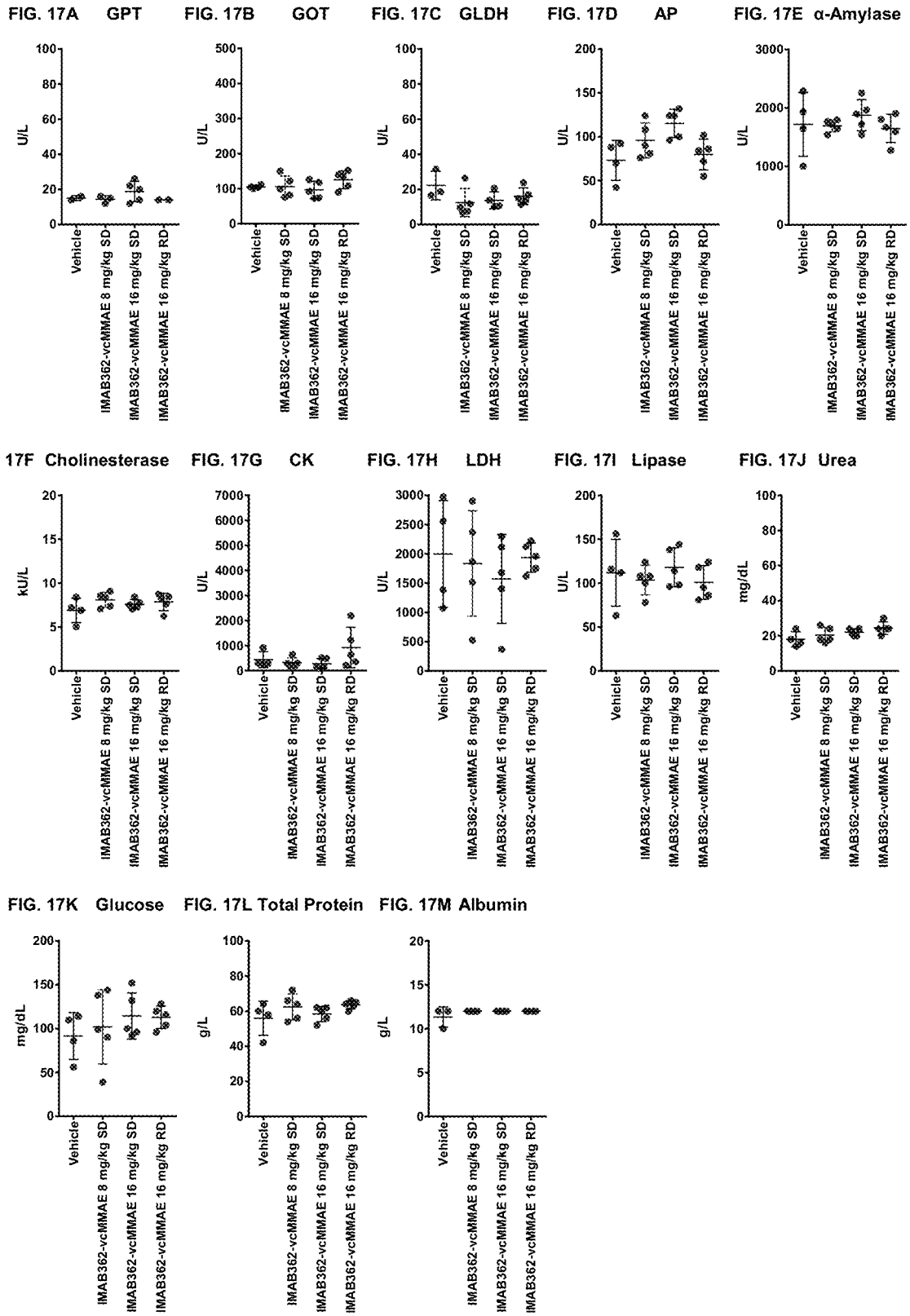

Clinical Chemistry:

We determined serum levels of surrogate markers for hepato-, nephro- or pancreatic toxicity (alanine transaminase (GPT), aspartate transaminase (GOT), glutamate dehydrogenase (GLDH) alkaline phosphatase (AP), alpha-amylase, cholinesterase, creatinine kinase (CK), lactate dehydrogenase (LDH), lipase, urea, glucose, total protein and albumin). Compared to the vehicle control group, no major deviations of the serum surrogate markers were observed in animals treated with IMAB362-vcMMAE (FIG. 17). Creatinine and gamma-glutamyl transferase were below the detection limit in all groups. Thus no signs of liver, pancreas or nephrotoxicity are observed in clinical biochemistry in the dose range evaluated.

Histological Analysis:

For histological analysis, paraffin sections from brain, heart, kidney, liver lung, pancreas, spleen and stomach were hematoxylin-eosin stained and microscopically examined for IMAB362-vcMMAE mediated morphological changes.

No IMAB362-vcMMAE related morphological changes could be observed in tissue sections from IMAB362-vcMMAE treated animals compared to vehicle treated mice, indicating that IMAB362-vcMMAE does neither induce tissue damage nor inflammation. Notably, even stomach, the only tissue expressing murine Cldn18.2 did not demonstrate antibody therapy mediated tissue damage (FIG. 22).

2. Efficacy Studies

Figure 18:
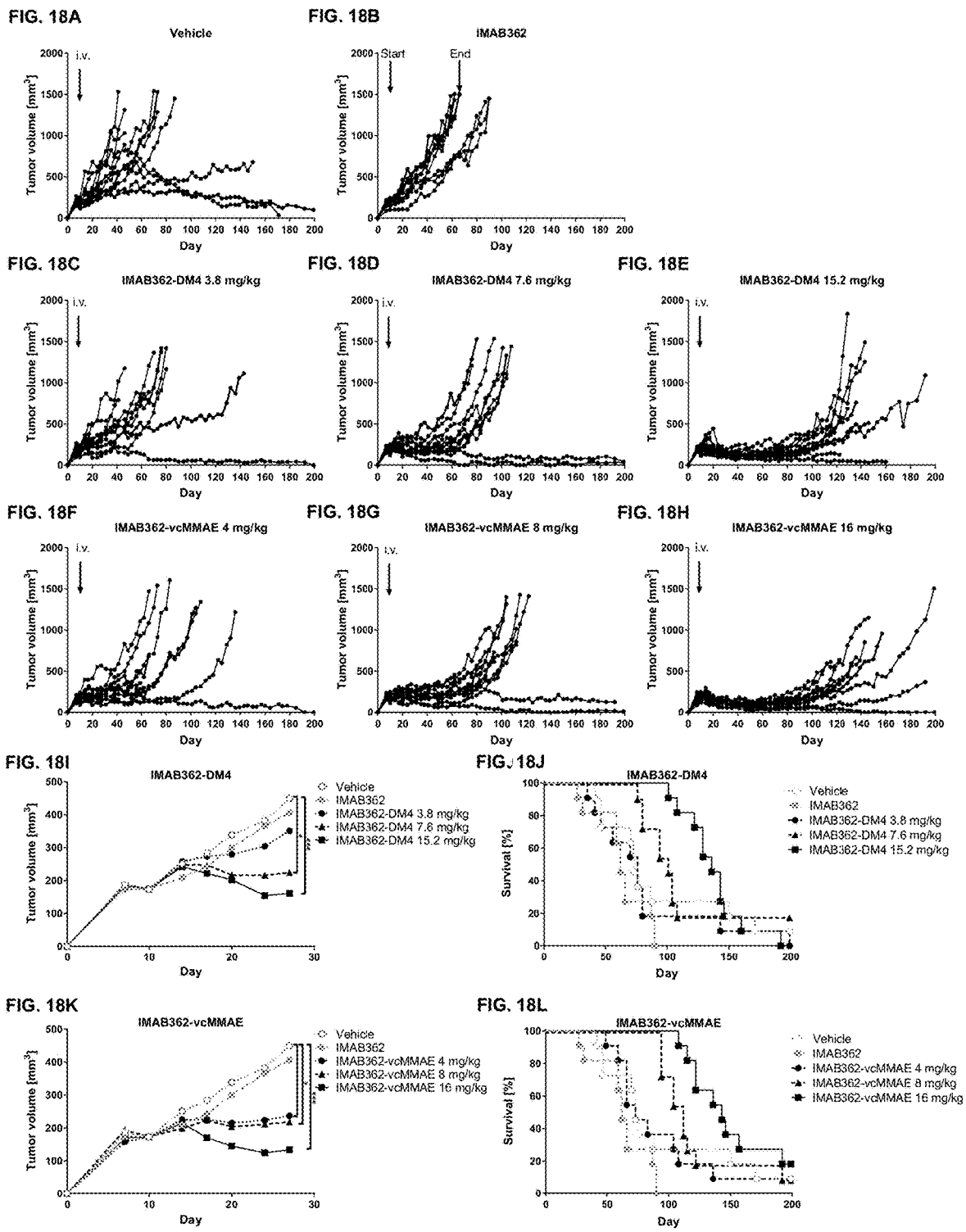
Figure 20A:
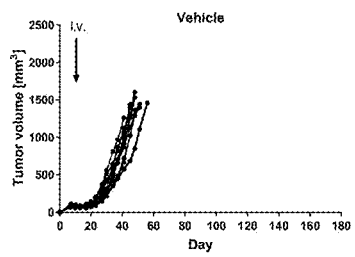
Figure 20B:
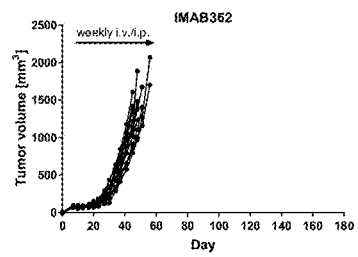
Figure 20C:
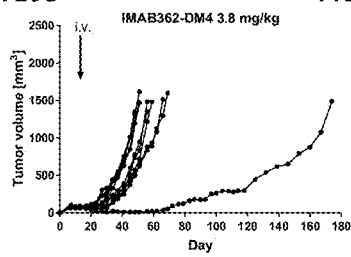
Figure 20D:
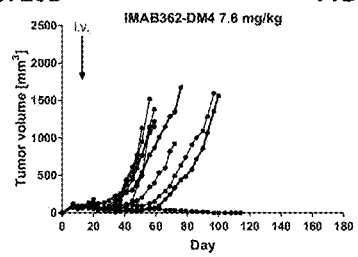
Figure 20E:
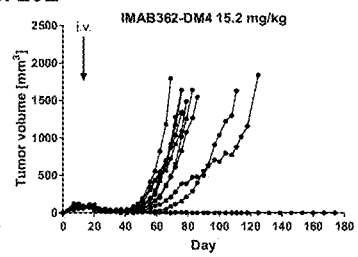
Figure 20F:
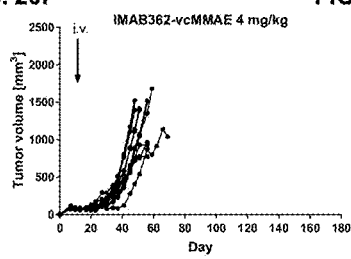
Figure 20G:
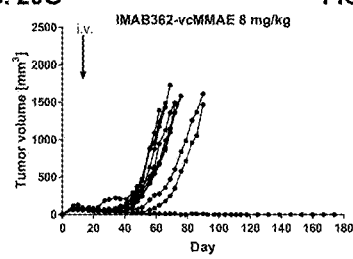
Figure 20H:
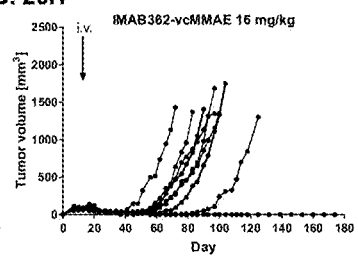
Figure 20I:
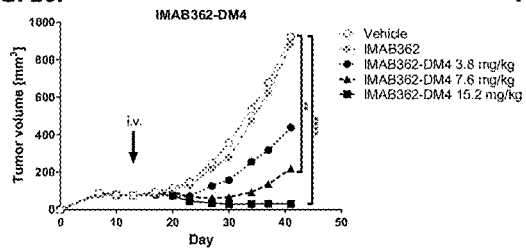
Figure 20J:
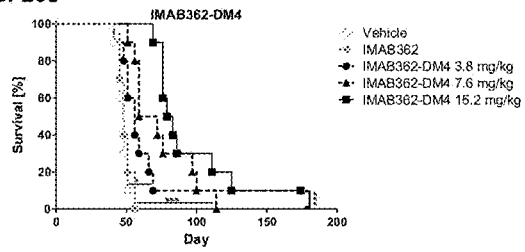
Figure 20K:
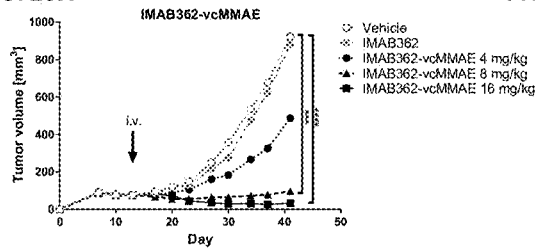
Figure 20L:
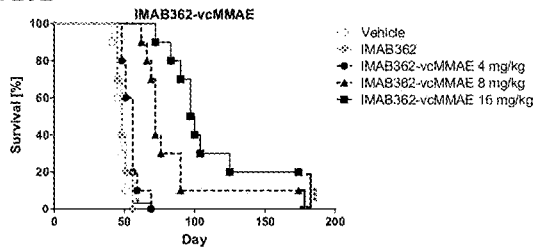
Figure 24A:
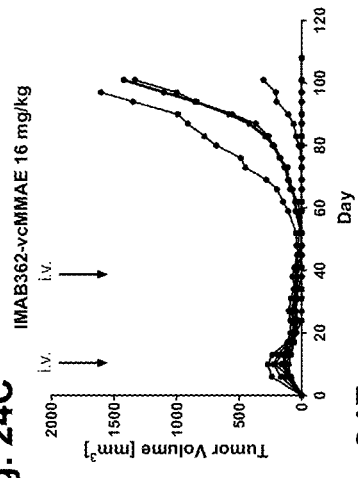
Figure 24B:
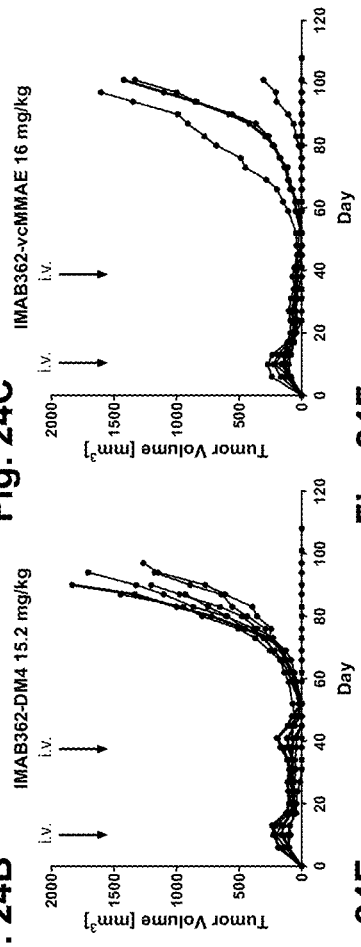
Figure 24C:
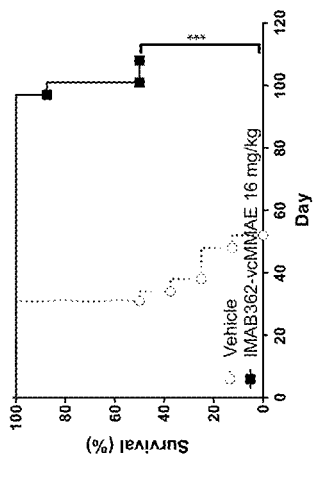
Figure 24D:
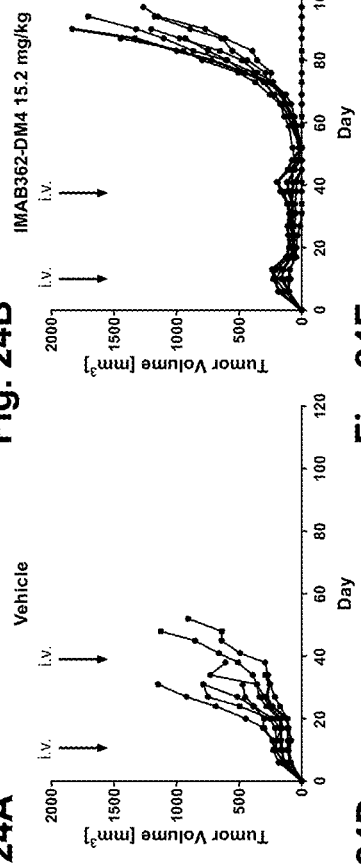
Figure 24E:
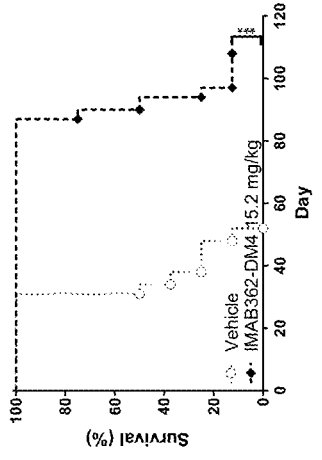
Figure 24F:
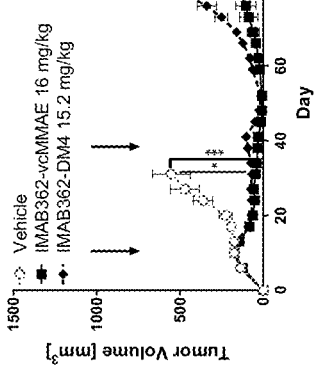

The anti-tumoral effects of IMAB362-DM4 and IMAB362-vcMMAE were further analyzed in vivo in athymic Nude-Foxn1$^{nu}$ mice subcutaneously engrafted with endogenously or ectopically CLDN18.2 expressing human carcinoma cells. The optimal therapeutic dose of IMAB362-DM4 and IMAB362-vcMMAE in animal tumor models was determined in dose range finding studies (FIG. 18 and FIG. 20, respectively). Further efficacy studies on human xenograft tumors were performed with the optimal dose of IMAB362-DM4 and IMAB362-vcMMAE (FIG. 19 and FIG. 21, respectively).

IMAB362-DM4 and IMAB362-vcMMAE highly significantly inhibit tumor growth and improve survival of tumor bearing mice in different early xenograft models (therapy initiation 3 days after tumor implantation) as well as in treatments of advanced solid tumors (therapy initiation at ~100 mm$^3$ tumor size).

Treatment of Advanced Human NCI-N87~CLDN18.2 Gastric Xenograft Tumors:

In a dose range finding study, the anti-tumoral efficacy of IMAB362-DM4 and IMAB362-vcMMAE was analyzed in mice with advanced CLDN18.2 positive NCI-N87~CLDN18.2 xenograft tumors. 13 days after engraftment, animals were treated with 15.2, 7.6 or 3.8 mg/kg IMAB362-DM4 or 16, 8 or 4 mg/kg IMAB362-vcMMAE or vehicle control applied as single IV bolus injections. Animals from the control group received 8 mg/kg unconjugated IMAB362 (twice a week, IV/i.p.).

IMAB362-DM4 and IMAB362-vcMMAE highly significantly inhibited tumor growth, mediated tumor regression and prolonged survival of tumor bearing mice in a dose dependent manner while IMAB362 naked antibody in this advanced treatment model did not exhibit statistically significant anti-tumoral effects (FIG. 18). Both IMAB362 toxin-conjugated antibodies prolonged survival of tumor bearing mice (median survival: 73 days in the vehicle group compared to 143 days in the IMAB362-vcMMAE 16 mg/kg and 136 days in the IMAB362-DM4 15.2 mg/kg group) (FIG. 18).

Treatment of Early Human NUGC-4 10cF7-5 sort3a Gastric Xenograft Tumors:

The anti-tumoral efficacy of IMAB362-DM4 and IMAB362-vcMMAE was analyzed in mice subcutaneously engrafted with NUGC-4 10cF7-5 sort3a gastric carcinoma cells endogenously expressing CLDN18.2. Animals were treated on day 3 post engraftment by single dose IV injection of 15.2 mg/kg IMAB362-DM4, 16 mg/kg IMAB362-vcMMAE or vehicle control. IMAB362-DM4 and IMAB362-vcMMAE prevented tumor growth in treated animals while all mice of the control group developed tumors (p<0.0001) (FIG. 19). After the pre-defined observation time of 120 days, 9 out of 10 animals which received IMAB362-DM4 or IMAB362-vcMMAE were alive and tumor free, whereas all animals from the vehicle control group had to be euthanized due to abort criteria latest on day 41 after engraftment (median survival 34 days, p<0.0003) (FIG. 19).

Treatment of Advanced Human BxPC-3~CLDN18.2 Pancreatic Xenograft Tumors:

Dose-dependent anti-tumoral activity of IMAB362-DM4 and IMAB362-vcMMAE in vivo was analyzed in a dose range finding study in mice with advanced human BxPC-3~CLDN18.2 pancreatic xenograft tumors. Animals were treated on day 14 with 15.2, 7.6 or 3.8 mg/kg IMAB362-DM4, 16, 8 or 4 mg/kg IMAB362-vcMMAE, vehicle administered as single bolus IV injections or with repeated doses of 8 mg/kg IMAB362 (twice a week, IV/i.p.).

IMAB362-DM4 and IMAB362-vcMMAE highly significantly inhibited tumor growth, mediated tumor regression and prolonged survival of tumor bearing mice in a dose dependent manner. In contrast, unconjugated IMAB362 did not exhibit statistically significant anti-tumoral activities in this advanced tumor model (FIG. 20). Both IMAB362 toxin-conjugated antibodies highly significantly prolonged survival of tumor bearing mice (median survival: 48 days in the vehicle group compared to 98.5 days in the IMAB362-vcMMAE 16 mg/kg and 81 days in the IMAB362-DM4 15.2 mg/kg group) (FIG. 20).

Treatment of Early Human DAN-G 1C5F2 Pancreatic Xenograft Tumors:

The anti-tumoral activity of IMAB362-DM4 and IMAB362-vcMMAE in vivo was tested in mice subcutaneously engrafted with DAN-G 1C5F2 pancreatic carcinoma cells endogenously expressing CLDN18.2. DAN-G 1C5F2 cells have only extremely low amounts of CLDN18.2 on the cell surface; although considerable amounts of protein or RNA can be detected by immunoblot or qRT-PCR. IHC analyses of DAN-G 1C5F2 xenograft tumors demonstrated that only a subpopulation of tumor cells showed moderate to strong membrane associated CLDN18.2 staining. Therefore, DAN-G 1C5F2 xenograft tumors might be suitable for treatment with antibody drug conjugates that exhibit bystander killing. Animals were treated on day 3 post engraftment by single dose IV injection of 15.2 mg/kg IMAB362-DM4, 16 mg/kg IMAB362-vcMMAE or vehicle control.

IMAB362-DM4 and IMAB362-vcMMAE highly significantly inhibited tumor growth and prolonged survival of tumor bearing mice compared to the vehicle control (FIG. 21). In the majority of mice (>50%) tumor growth was completely prevented. After the observation period of 120 days, 2 out of 7 animals in the IMAB362-DM4 (median survival 87 days, p=0.0002) and 4 out 7 animals in the IMAB362-vcMMAE treatment group were still alive (survival undefined, p=0.0006), whereas all animals of the vehicle group had to be euthanized within 31 days due to abort criteria such as cancer cachexia (median survival 24 days) (FIG. 21). Both, IMAB362-DM4 and IMAB362-vcMMAE significantly inhibiting tumor growth and prolonging survival of mice with xenograft tumors exhibiting heterogeneous CLDN18.2 expression.

In summary, tumors with low and/or heterogeneous expression of CLDN18.2 (e.g. NUGC-4 and DAN-G xenograft tumors) can be efficiently treated with IMAB362-DM4 or IMAB362-vcMMAE and a large part of tumor-bearing animals were cured. The anti-tumoral activities of both ADCs can be explained on the basis of the bystander effect: The release of cell membrane-permeable forms of DM4 and MMAE after cellular processing facilitates the killing of neighboring tumor cells even if they are target negative. Therefore, both ADCs are highly effective in eradicating tumors containing only fractions of CLDN18.2 positive cells.

Example 7: Induction of Apoptosis

The cytotoxicity of toxin-conjugated IMAB362 was evaluated by apoptosis assays measuring caspase 3/7 activity and the externalization of phosphatidylserine. Caspase activation represents one of the earliest measurable markers of apoptosis which is important for the initiation of programed cell death (Henkart 1996). Caspase 3/7 activity was determined in a luciferase-based assay by the cleavage of a caspase 3/7 specific pro-luminogenic substrate. Another early event in apoptosis was monitored by flow cytometry using fluorescence-conjugated annexin V (Vermes et al. 1995). Annexin V specifically binds to phosphatidylserine which is translocated from the inner leaflet of the plasma membrane to the outer leaflet immediately after the induction of apoptosis. To discriminate between living and dead cells, cells are co-stained with the DNA dye propidium iodide (PI).

To analyze induction of apoptosis, CLDN18.2 positive NUGC4 cells were treated with a single dose of IMAB362-toxin conjugates for several days. Untreated cells and cells treated with non-conjugated IMAB362 served as controls (FIG. 23). After 3 days, cells treated with IMAB362-DM4 or IMAB362-vcMMAE showed increased caspase 3/7 activities whereas incubation with the naked antibody did not influence caspase activity (FIG. 23A). Co-staining with annexin V and PI was used as an independent parameter to verify the induction of apoptosis by toxin-conjugated IMAB362 antibodies. 4 days after treatment, —50% of the cells treated with IMAB362-DM4- or IMAB362-vcMMAE were found to be annexin V or annexin V/PI positive, indicating that cell death occurred via induction of apoptosis. In contrast, naked IMAB362 without cross-linking does not induce apoptosis in the concentration range applied (FIG. 23B).

In summary, treatment of CLDN18.2 positive tumor cells with IMAB362 conjugated to DM4 or vcMMAE induces apoptosis.

Example 8: Treatment of Advanced Human NUGC-4 10CF7-5 SORT3A Gastric Xenograft Tumors The anti-tumoral efficacy of IMAB362-DM4 and IMAB362-vcMMAE was analyzed in mice subcutaneously engrafted with NUGC-4 10cF7-5 sort3a gastric carcinoma cells endogenously expressing CLDN18.2. Animals with advanced tumors (tumor size of ~200 mm3) were treated on day 10 post engraftment by IV injection of 15.2 mg/kg IMAB362-DM4, 16 mg/kg IMAB362-vcMMAE or vehicle control and after recurrence of tumors in the IMAB362 conjugate treated groups by a second injection of the respective drug (day 38).

IMAB362-DM4 and IMAB362-vcMMAE significantly inhibited tumor growth and mediated tumor regression in all treated animals (day 52) while all mice of the control group developed tumors (IMAB362-DM4: p<0.05; IMAB362-vcMMAE: p<0.001) (FIG. 24). 28 days after therapy (day 38 post engraftment) recurrent tumor growth (tumor size ≥~100 mm3) was observed in 50% of the animals of the IMAB362-DM4 treated group. The second injection of the respective IMAB362-DM4 and IMAB362-vcMMAE again resulted in partial or complete remission of the tumors. Recurrent tumor growth finally was observed in 7 out of 8 animals in the IMAB362-DM4 group and 4 out of 8 animals in the IMAB362-vcMMAE group. After the pre-defined time point of treatment end (day 108 post graft), 4 out 8 animals in the IMAB362-vcMMAE group and one animal in the IMAB362-DM4 and IMAB362 group were alive while all animals of the vehicle group died latest on day 52 post engraftment (median survival 32.5 days for vehicle, 90 days for IMAB362-DM4 (p<0.0003 vs vehicle) and undefined for IMAB362-vcMMAE (p<0.0003 vs vehicle)) (FIG. 24).

Example 9: Induction of Antibody-Dependent Cellular Cytotoxicity (ADCC) and Complement-Dependent Cytotoxicity (CDC)

Antibody-Dependent Cellular Cytotoxicity (ADCC):
The ADCC activities of DM4- and MMAE-conjugated IMAB362 antibodies were compared with unconjugated IMAB362 using NUGC-4 10cF7_5 sort3a p3151 #10 human stomach carcinoma cells endogenously expressing CLDN18.2 (FIG. 25, Table 10).

TABLE 10

ADCC-activity of IMAB362-DM4 and IMAB362-vcMMAE on NUGC-4 10cF7_5 sort3a p3151#10 cells

| | IMAB362 | | IMAB362-DM4 | | IMAB362-vcMMAE | |
|---|---|---|---|---|---|---|
| Donor | Max Lysis [%] | EC50 [ng/ml] | Max Lysis [%] | EC50 [ng/ml] | Max Lysis [%] | EC50 [ng/ml] |
| Donor 1 | 75 | 1228 | 66 | 1151 | 73 | 1085 |
| Donor 2 | 82 | 142 | 92 | 217 | 92 | 275 |

Both toxin-conjugated antibodies, IMAB362-DM4 and IMAB362-vcMMAE, exhibited similar EC50 and maximal lysis values compared to the unconjugated antibody IMAB362, indicating that ADCC-activity was retained after drug conjugation.

Complement-Dependent Cytotoxicity (CDC):
The CDC activities of IMAB362-DM4 and IMAB362-vcMMAE were analyzed on endogenously CLDN18.2 expressing NUGC-4 10cF7_5 sort3A p3151 #10 and KATO-III FGF-BP #12 adM p3151 #25 human stomach carcinoma cells (FIG. 26, Table 11).

TABLE 11

CDC-activity of IMAB362-DM4 and IMAB362-vcMMAE on endogenously CLDN18.2 expressing carcinoma cells.

| | IMAB362 | | IMAB362-DM4 | | IMAB362-vcMMAE | |
|---|---|---|---|---|---|---|
| Cell line | Max Lysis [%] | EC50 [ng/ml] | Max Lysis [%] | EC50 [ng/ml] | Max Lysis [%] | EC50 [ng/ml] |
| KATO-III FGF-BP#12 adM p3151#25 | 43 | 19292 | 56 | 6439 | 51 | 7244 |
| NUGC-4 10cF7_5 sort3a p3151#10 | 54 | 28043 | 48 | 15759 | 49 | 28338 |

CDC-activity was not affected by conjugation of the toxins to the antibody IMAB362. Both toxin-conjugated antibodies, IMAB362-DM4 and IMAB362-vcMMAE, exhibited at least similar EC50 and maximal lysis values compared to the unconjugated antibody IMAB362.

Thus, IMAB362-DM4 and IMAB362-vcMMAE combine toxin-mediated cytotoxicity with antibody dependent cellular cytotoxicity and complement dependent cytotoxicity, the major modes of actions of the unconjugated IMAB362, thereby improving overall therapeutic activity.

| Applicant's or agent's file reference 342-84 PCT | International application No. |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 40, line 25.

B. IDENTIFICATION OF DEPOSIT    Further deposits are identified on an additional sheet [X]

Name of depositary institution
DSMZ-Deutsche Sammlung von Mikroorganismen und Zellkulturen GmbH Address of depositary institution (including postal code and country)
Mascheroder Weg 1b
38124 Braunschweig
DE

| Date of deposit: October 19, 2005 | Accession Number DSM ACC2737 |
|---|---|

C. ADDITIONAL INDICATIONS (leave blank if not applicable)    This information is continued on an additional sheet [ ]

- Mouse (Mus musculus) myeloma P3X63Ag8U.1 fused with mouse (Mus musculus) splenocytes

- Hybridoma secreting antibody against human claudin-18A2

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| [ ] This sheet was received with the international application | [ ] This sheet was received by the International Bureau on: |
| Authorized officer | Authorized officer |

Form PCT/RO/134 (July 1998; reprint January 2004)

New International Patent Application
Ganymed Pharmaceuticals AG, et al.
"DRUG CONJUGATES COMPRISING ANTIBODIES AGAINST CLAUDIN 18.2"
Our Ref.: 342-84 PCT

---

Additional Sheet for Biological Material

Identification of further deposits:

1) The Name and Address of depositary institution for the deposits (DSM ACC2738, DSM ACC2739, DSM ACC2740, DSM ACC2741, DSM ACC2742, DSM ACC2743, DSM ACC2745, DSM ACC2746, DSM ACC2747, DSM ACC2748) are:

DSMZ-Deutsche Sammlung von Mikroorganismen und Zellkulturen GmbH
   Mascheroder Weg 1b
   38124 Braunschweig
   DE 2) The Name and Address of depositary institution for the deposits (DSM ACC2808, DSM ACC2809, DSM ACC2810) are:

DSMZ-Deutsche Sammlung von Mikroorganismen und Zellkulturen GmbH
   Inhoffenstr. 7 B
   38124 Braunschweig
   DE

| Date of desposits | Accession Numbers | The indications made below relate to the deposited microorganism in the description on the following page(s) |
|---|---|---|
| October 19, 2005 | DSM ACC2738 | page 39, line 23 |
| October 19, 2005 | DSM ACC2739 | page 39, line 24 |
| October 19, 2005 | DSM ACC2740 | page 39, line 25 |
| October 19, 2005 | DSM ACC2741 | page 39, line 26 |
| October 19, 2005 | DSM ACC2742 | page 39, line 27 |
| October 19, 2005 | DSM ACC2743 | page 39, line 28 |
| November 17, 2005 | DSM ACC2745 | page 39, line 29 |
| November 17, 2005 | DSM ACC2746 | page 39, line 30 |
| November 17, 2005 | DSM ACC2747 | page 39, line 31 |
| November 17, 2005 | DSM ACC2748 | page 40, line 1 |
| October 26, 2006 | DSM ACC2808 | page 40, line 2 |
| October 26, 2006 | DSM ACC2809 | page 40, line 3 |
| October 26, 2006 | DSM ACC2810 | page 40, line 4 |

Additional Indications for all above mentioned deposits:

- Mouse (Mus musculus) myeloma P3X63Ag8U.1 fused with mouse (Mus musculus) splenocytes
- Hybridoma secreting antibody against human claudin-18A2

3) Depositor:

All above mentioned depositions were made by:

Ganymed Pharmaceuticals AG
Freiligrathstrasse 12
55131 Mainz
DE

The invention claimed is:

1. A method of treating a cancer expressing a human CLDN18.2 polypeptide by administering an antibody-drug conjugate to a human patient, said antibody-drug conjugate comprising an antibody having the ability of binding to a polypeptide comprising the amino acid sequence of SEQ ID NO: 1 covalently attached to at least one toxin drug moiety, wherein the antibody-drug conjugate, upon binding to cells expressing the human CLDN18.2 polypeptide, is internalized into the cells and wherein the antibody-drug conjugate mediates killing of the cells through toxin-mediated cytotoxicity, complement dependent cytotoxicity (CDC) mediated lysis, and antibody dependent cellular cytotoxicity (ADCC) mediated lysis;
wherein the antibody having the ability of binding to the polypeptide comprising the amino acid sequence of SEQ ID NO: 1 recognizes the same epitope as a CLDN18.2-binding antibody comprising an antibody heavy chain comprising the amino acid sequence of SEQ ID NO: 32 and an antibody light chain comprising the amino acid sequence of SEQ ID NO: 39;
wherein the antibody having the ability of binding to the polypeptide comprising the amino acid sequence of SEQ ID NO: 1 comprises a heavy chain variable region ($V_H$) comprising a $V_H$ CDR1 of positions 45-52 of SEQ ID NO: 17, a $V_H$ CDR2 of positions 70-77 of SEQ ID NO: 17, and a $V_H$ CDR3 of positions 116-126 of SEQ ID NO: 17 and a light chain variable region ($V_L$) comprising a $V_L$ CDR1 of positions 47-58 of SEQ ID NO: 24, a $V_L$ CDR2 of positions 76-78 of SEQ ID NO: 24, and a $V_L$ CDR3 of positions 115-123 of SEQ ID NO: 24;
wherein the antibody having the ability of binding to the polypeptide comprising the amino acid sequence of SEQ ID NO: 1 comprises a human heavy chain constant region selected from the group consisting of IgG1 and IgG3;
wherein (a) the toxin drug moiety is a maytansinoid or an auristatin; and (b) the antibody is covalently attached to the toxin drug moiety by a cleavable linker.

2. The method of claim 1, wherein the antibody comprises an antibody heavy chain comprising the amino acid sequence of SEQ ID NO: 32 and an antibody light chain comprising the amino acid sequence of SEQ ID NO: 39.

3. The method of claim 1, wherein the antibody comprises an antibody heavy chain comprising the amino acid sequence of SEQ ID NO: 17 or 51 and an antibody light chain comprising the amino acid sequence of SEQ ID NO: 24.

4. The method of claim 1, wherein the maytansinoid is selected from the group consisting of DM1 and DM4.

5. The method of claim 1, wherein the auristatin is selected from the group consisting of monomethyl auristatin E (MMAE) and monomethyl auristatin F (MMAF).

6. The method of claim 1, wherein the linker is cleavable by an intracellular protease.

7. The method of claim 1, wherein the linker is a cathepsin-cleavable linker.

8. The method of claim 1, wherein the linker comprises a dipeptide.

9. The method of claim 8, wherein the dipeptide is val-cit or phe-lys.

10. The method of claim 1, which further comprises administering surgery, chemotherapy and/or radiation therapy.

11. The method of claim 1, wherein the cancer is an adeno-carcinoma.

12. The method of claim 1, wherein the cancer is selected from the group consisting of gastric cancer, esophageal cancer, pancreatic cancer, lung cancer, breast cancer, ovarian cancer, colon cancer, hepatic cancer, head-neck cancer, cancer of the gallbladder and the metastasis thereof, a Krukenberg tumor, peritoneal metastasis, and lymph node metastasis.

13. The method of claim 1, wherein the cancer is selected from the group consisting of cancer of the stomach, cancer of the esophagus, cancer of the eso-gastric junction, and gastroesophageal cancer.

14. The method of claim 1, wherein the human CLDN18.2 polypeptide comprises the amino acid sequence SEQ ID NO: 1.

15. The method of claim 1, wherein the cancer is an advanced adenocarcinoma.

16. The method of claim 1, wherein the cancer is selected from the group consisting of cancer of the lower esophagus, cancer of the eso-gastric junction, and gastroesophageal cancer.

17. The method of claim 1, wherein the cancer is gastric cancer.

18. The method of claim 1, wherein the toxin drug moiety is selected from the group consisting of DM4 and monomethyl auristatin E (MMAE).

19. A method of treating a gastric, esophageal, or pancreatic cancer expressing a human CLDN18.2 polypeptide by administering an antibody-drug conjugate to a human patient, said antibody-drug conjugate comprising an antibody having the ability of binding to a polypeptide comprising the amino acid sequence of SEQ ID NO: 1 covalently attached to at least one toxin drug moiety via a cleavable linker, wherein the antibody-drug conjugate, upon binding to cells expressing the human CLDN18.2 polypeptide, is internalized into the cells and wherein the antibody-drug conjugate mediates killing of the cells through toxin-mediated cytotoxicity, complement dependent cytotoxicity (CDC) mediated lysis, and antibody dependent cellular cytotoxicity (ADCC) mediated lysis;

wherein the antibody having the ability of binding to the polypeptide comprising the amino acid sequence of SEQ ID NO: 1 comprises a heavy chain variable region ($V_H$) comprising a $V_H$ CDR1 of positions 45-52 of SEQ ID NO: 17, a $V_H$ CDR2 of positions 70-77 of SEQ ID NO: 17, and a $V_H$ CDR3 of positions 116-126 of SEQ ID NO: 17 and a light chain variable region ($V_L$) comprising a $V_L$ CDR1 of positions 47-58 of SEQ ID NO: 24, a $V_L$ CDR2 of positions 76-78 of SEQ ID NO: 24, and a $V_L$ CDR3 of positions 115-123 of SEQ ID NO: 24;

wherein the antibody having the ability of binding to the polypeptide comprising the amino acid sequence of SEQ ID NO: 1 (a) recognizes the same epitope as a CLDN18.2-binding antibody comprising an antibody heavy chain comprising the amino acid sequence of SEQ ID NO: 32 and an antibody light chain comprising the amino acid sequence of SEQ ID NO: 39 or (b) comprises an antibody heavy chain comprising the amino acid sequence of SEQ ID NO: 32 and an antibody light chain comprising the amino acid sequence of SEQ ID NO: 39;

wherein the toxin drug moiety is selected from the group consisting of DM4 and monomethyl auristatin E (MMAE).

20. The method of claim 19, wherein the cleavable linker is an N-succinimidyl-4-(2-pyridyldithio)butyrate linker.

21. The method of claim 19, wherein the cleavable linker is a valine-citrulline linker.

22. The method of claim 19, wherein the toxin drug moiety is DM4 and the cleavable linker is an N-succinimidyl-4-(2-pyridyldithio)butyrate linker.

23. The method of claim 22, wherein the antibody comprises an antibody heavy chain comprising the amino acid sequence of SEQ ID NO: 32 and an antibody light chain comprising the amino acid sequence of SEQ ID NO: 39.

24. The method of claim 22, wherein the antibody comprises an antibody heavy chain comprising the amino acid sequence of SEQ ID NO: 17 or 51 and an antibody light chain comprising the amino acid sequence of SEQ ID NO: 24.

25. The method of claim 19, wherein the toxin drug moiety is MMAE and the cleavable linker is a valine-citrulline linker.

26. The method of claim 25, wherein the antibody comprises an antibody heavy chain comprising the amino acid sequence of SEQ ID NO: 32 and an antibody light chain comprising the amino acid sequence of SEQ ID NO: 39.

27. The method of claim 25, wherein the antibody comprises an antibody heavy chain comprising the amino acid sequence of SEQ ID NO: 17 or 51 and an antibody light chain comprising the amino acid sequence of SEQ ID NO: 24.

28. The method of claim 1, wherein the cancer is non small cell lung cancer (NSCLC).

* * * * *

SEQUENCE LISTING

<160> NUMBER OF SEQ ID NOS: 51

<210> SEQ ID NO 1
<211> LENGTH: 261
<212> TYPE: PRT
<213> ORGANISM: Homo sapiens

<400> SEQUENCE: 1

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 2
<211> LENGTH: 261
<212> TYPE: PRT
<213> ORGANISM: Homo sapiens

<400> SEQUENCE: 2

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg

```
            50                  55                  60
Pro Tyr Phe Thr Ile Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                 85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 3
<211> LENGTH: 10
<212> TYPE: PRT
<213> ORGANISM: Homo sapiens

<400> SEQUENCE: 3

Asp Gln Trp Ser Thr Gln Asp Leu Tyr Asn
 1               5                  10

<210> SEQ ID NO 4
<211> LENGTH: 11
<212> TYPE: PRT
<213> ORGANISM: Homo sapiens

<400> SEQUENCE: 4

Asn Asn Pro Val Thr Ala Val Phe Asn Tyr Gln
 1               5                  10

<210> SEQ ID NO 5
<211> LENGTH: 14
<212> TYPE: PRT
<213> ORGANISM: Homo sapiens

<400> SEQUENCE: 5

Ser Thr Gln Asp Leu Tyr Asn Asn Pro Val Thr Ala Val Phe
 1               5                  10

<210> SEQ ID NO 6
<211> LENGTH: 13
<212> TYPE: PRT
<213> ORGANISM: Homo sapiens
```

-continued

<400> SEQUENCE: 6

Thr Asn Phe Trp Met Ser Thr Ala Asn Met Tyr Thr Gly
1               5                   10

<210> SEQ ID NO 7
<211> LENGTH: 13
<212> TYPE: PRT
<213> ORGANISM: Homo sapiens

<400> SEQUENCE: 7

Asp Ser Ala Lys Ala Asn Met Thr Leu Thr Ser Gly Ile
1               5                   10

<210> SEQ ID NO 8
<211> LENGTH: 55
<212> TYPE: PRT
<213> ORGANISM: Homo sapiens

<400> SEQUENCE: 8

Met Asp Gln Trp Ser Thr Gln Asp Leu Tyr Asn Asn Pro Val Thr Ala
1               5                   10                  15

Val Phe Asn Tyr Gln Gly Leu Trp Arg Ser Cys Val Arg Glu Ser Ser
                20                  25                  30

Gly Phe Thr Glu Cys Arg Gly Tyr Phe Thr Leu Leu Gly Leu Pro Ala
            35                  40                  45

Met Leu Gln Ala Val Arg Ala
        50                  55

<210> SEQ ID NO 9
<211> LENGTH: 24
<212> TYPE: PRT
<213> ORGANISM: Homo sapiens

<400> SEQUENCE: 9

Phe Ala Leu Lys Cys Ile Arg Ile Gly Ser Met Glu Asp Ser Ala Lys
1               5                   10                  15

Ala Asn Met Thr Leu Thr Ser Gly
                20

<210> SEQ ID NO 10
<211> LENGTH: 40
<212> TYPE: PRT
<213> ORGANISM: Homo sapiens

<400> SEQUENCE: 10

Ala Asn Met Leu Val Thr Asn Phe Trp Met Ser Thr Ala Asn Met Tyr
1               5                   10                  15

Thr Gly Met Gly Gly Met Val Gln Thr Val Gln Thr Arg Tyr Thr Phe
                20                  25                  30

Gly Ala Ala Leu Phe Val Gly Trp
            35                  40

<210> SEQ ID NO 11
<211> LENGTH: 153
<212> TYPE: PRT
<213> ORGANISM: Homo sapiens

<400> SEQUENCE: 11

Met Asp Gln Trp Ser Thr Gln Asp Leu Tyr Asn Asn Pro Val Thr Ala
1               5                   10                  15

```
Val Phe Asn Tyr Gln Gly Leu Trp Arg Ser Cys Val Arg Glu Ser Ser
             20                  25                  30

Gly Phe Thr Glu Cys Arg Gly Tyr Phe Thr Leu Leu Gly Leu Pro Ala
         35                  40                  45

Met Leu Gln Ala Val Arg Ala Leu Met Ile Val Gly Ile Val Leu Gly
 50                  55                  60

Ala Ile Gly Leu Leu Val Ser Ile Phe Ala Leu Lys Cys Ile Arg Ile
65                  70                  75                  80

Gly Ser Met Glu Asp Ser Ala Lys Ala Asn Met Thr Leu Thr Ser Gly
                 85                  90                  95

Ile Met Phe Ile Val Ser Gly Leu Cys Ala Ile Ala Gly Val Ser Val
            100                 105                 110

Phe Ala Asn Met Leu Val Thr Asn Phe Trp Met Ser Thr Ala Asn Met
        115                 120                 125

Tyr Thr Gly Met Gly Gly Met Val Gln Thr Val Gln Thr Arg Tyr Thr
    130                 135                 140

Phe Gly Ala Ala Leu Phe Val Gly Trp
145                 150

<210> SEQ ID NO 12
<211> LENGTH: 107
<212> TYPE: PRT
<213> ORGANISM: Artificial
<220> FEATURE:
<223> OTHER INFORMATION: Description of artificial sequence: Translation
      of PCR product

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 326
<212> TYPE: PRT
<213> ORGANISM: Artificial
<220> FEATURE:
<223> OTHER INFORMATION: Description of artificial sequence: Translation
      of PCR product

<400> SEQUENCE: 13

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45
```

```
Phe Pro Ala Val Leu Gln Ser Ser Gly Leu Tyr Ser Leu Ser Ser Val
    50                  55                  60

Val Thr Val Pro Ser Ser Leu Gly Thr Gln Thr Tyr Ile Cys Asn
65                  70                  75                  80

Val Asn His Lys Pro Ser Asn Thr Lys Val Asp Lys Val Glu Pro
                85                  90                  95

Lys Ser Cys Asp Lys Thr His Thr Cys Pro Pro Cys Pro Ala Pro Glu
                100                 105                 110

Leu Leu Gly Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 14
<211> LENGTH: 466
<212> TYPE: PRT
<213> ORGANISM: Artificial
<220> FEATURE:
<223> OTHER INFORMATION: Description of artificial sequence: chimeric
      monoclonal antibody

<400> SEQUENCE: 14

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
                20                  25                  30

Pro Gly Ala Ser Val Lys Ile Ser Cys Lys Ala Thr Gly Tyr Thr Phe
            35                  40                  45

Ser Ser Tyr Trp Ile Glu Trp Val Lys Gln Arg Pro Gly His Gly Leu
        50                  55                  60

Glu Trp Ile Gly Glu Ile Leu Pro Gly Ser Gly Ser Thr Asn Tyr Asn
65                  70                  75                  80
```

```
Glu Lys Phe Lys Gly Lys Ala Thr Phe Thr Ala Asp Thr Ser Ser Asn
                 85                  90                  95

Thr Ala Tyr Met Gln Leu Ser Ser Leu Thr Ser Glu Asp Ser Ala Val
            100                 105                 110

Tyr Tyr Cys Ala Arg Tyr Asp Tyr Pro Trp Phe Ala Tyr Trp Gly Gln
        115                 120                 125

Gly Thr Leu Val Thr Val Ser Ala Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 15
<211> LENGTH: 467
```

<212> TYPE: PRT
<213> ORGANISM: Artificial
<220> FEATURE:
<223> OTHER INFORMATION: Description of artificial sequence: chimeric
      monoclonal antibody

<400> SEQUENCE: 15

```
Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380
```

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 16
<211> LENGTH: 465
<212> TYPE: PRT
<213> ORGANISM: Artificial
<220> FEATURE:
<223> OTHER INFORMATION: Description of artificial sequence: chimeric
      monoclonal antibody

<400> SEQUENCE: 16

Met Glu Trp Ile Trp Ile Phe Leu Phe Ile Leu Ser Gly Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Asp Tyr Tyr Ile Asn Trp Val Lys Gln Arg Thr Gly Gln Gly Leu
    50                  55                  60

Glu Trp Ile Gly Glu Ile Tyr Pro Gly Ser Gly Asn Thr Tyr Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Ser Tyr Gly Ala Phe Asp Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
```

```
                    260                 265                 270
Arg Thr Pro Glu Val Thr Cys Val Val Asp Val Ser His Glu Asp
                275                 280                 285

Pro Glu Val Lys Phe Asn Trp Tyr Val Asp Gly Val Glu Val His Asn
                290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Arg Asp Glu Leu Thr Lys Asn Gln Val Ser Leu Thr
                370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
                435                 440                 445

Ala Leu His Asn His Tyr Thr Gln Lys Ser Leu Ser Leu Ser Pro Gly
                450                 455                 460

Lys
465

<210> SEQ ID NO 17
<211> LENGTH: 467
<212> TYPE: PRT
<213> ORGANISM: Artificial
<220> FEATURE:
<223> OTHER INFORMATION: Description of artificial sequence: chimeric
      monoclonal antibody

<400> SEQUENCE: 17

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
                20                  25                  30

Pro Gly Ala Ser Val Lys Leu Ser Cys Lys Ala Ser Gly Tyr Thr Phe
                35                  40                  45

Thr Ser Tyr Trp Ile Asn Trp Val Lys Gln Arg Pro Gly Gln Gly Leu
                50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
                100                 105                 110

Tyr Tyr Cys Thr Arg Ser Trp Arg Gly Asn Ser Phe Asp Tyr Trp Gly
                115                 120                 125

Gln Gly Thr Thr Leu Thr Val Ser Ser Ala Ser Thr Lys Gly Pro Ser
                130                 135                 140
```

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 18
<211> LENGTH: 466
<212> TYPE: PRT
<213> ORGANISM: Artificial
<220> FEATURE:
<223> OTHER INFORMATION: Description of artificial sequence: chimeric
      monoclonal antibody

<400> SEQUENCE: 18

Met Glu Trp Arg Ile Phe Leu Phe Ile Leu Ser Gly Thr Ala Gly Val
1               5                   10                  15

His Ser Gln Val Gln Leu Gln Gln Ser Gly Pro Glu Leu Val Lys Pro
            20                  25                  30

```
Gly Ala Ser Val Lys Met Ser Cys Lys Ala Ser Gly Tyr Thr Phe Thr
        35                  40                  45

Asp Tyr Val Ile Ser Trp Val Lys Gln Arg Thr Gln Gly Leu Glu
 50                  55                  60

Trp Ile Gly Glu Ile Tyr Pro Gly Ser Gly Ser Thr Tyr Tyr Asn Glu
 65                  70                  75                  80

Lys Phe Lys Gly Lys Ala Thr Leu Thr Ala Asp Lys Ser Ser Asn Thr
                 85                  90                  95

Ala Tyr Met Gln Leu Ser Ser Leu Thr Ser Glu Asp Ser Ala Val Tyr
                100                 105                 110

Phe Cys Ala Arg Gly Val Leu Leu Arg Ala Met Asp Tyr Trp Gly Gln
             115                 120                 125

Gly Thr Ser Val Thr Val Ser Ser Ala Ser Thr Lys Gly Pro Ser Val
         130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445
```

```
Glu Ala Leu His Asn His Tyr Thr Gln Lys Ser Leu Ser Leu Ser Pro
        450                 455                 460
Gly Lys
465

<210> SEQ ID NO 19
<211> LENGTH: 469
<212> TYPE: PRT
<213> ORGANISM: Artificial
<220> FEATURE:
<223> OTHER INFORMATION: Description of artificial sequence: chimeric
      monoclonal antibody

<400> SEQUENCE: 19

Met Asp Trp Ile Trp Ile Met Leu His Leu Leu Ala Ala Ala Thr Gly
1               5                   10                  15

Ile Gln Ser Gln Val His Leu Gln Gln Ser Gly Ser Glu Leu Arg Ser
            20                  25                  30

Pro Gly Ser Ser Val Lys Leu Ser Cys Lys Asp Phe Asp Ser Glu Val
        35                  40                  45

Phe Pro Phe Ala Tyr Met Ser Trp Ile Arg Gln Lys Pro Gly His Gly
    50                  55                  60

Phe Glu Trp Ile Gly Asp Ile Leu Pro Ser Ile Gly Arg Thr Ile Tyr
65                  70                  75                  80

Gly Glu Lys Phe Glu Asp Lys Ala Thr Leu Asp Ala Asp Thr Val Ser
                85                  90                  95

Asn Thr Ala Tyr Leu Glu Leu Asn Ser Leu Thr Ser Glu Asp Ser Ala
            100                 105                 110

Ile Tyr Tyr Cys Ala Arg Gly Glu Gly Tyr Gly Ala Trp Phe Ala Tyr
        115                 120                 125

Trp Gly Gln Gly Thr Leu Val Thr Val Ser Ala Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335
```

```
Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly Lys
465

<210> SEQ ID NO 20
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 20

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Leu Thr Phe Gly Ala Gly Thr
        115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
```

```
Gln Gly Leu Ser Ser Pro Val Thr Lys Ser Phe Asn Arg Gly Glu Cys
225                 230                 235                 240

<210> SEQ ID NO 21
<211> LENGTH: 235
<212> TYPE: PRT
<213> ORGANISM: Artificial
<220> FEATURE:
<223> OTHER INFORMATION: Description of artificial sequence: chimeric
      monoclonal antibody

<400> SEQUENCE: 21

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
        35                  40                  45

Ser Ser Val Ser Tyr Met His Trp Phe Gln Gln Lys Pro Gly Thr Ser
    50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 22
<211> LENGTH: 234
<212> TYPE: PRT
<213> ORGANISM: Artificial
<220> FEATURE:
<223> OTHER INFORMATION: Description of artificial sequence: chimeric
      monoclonal antibody

<400> SEQUENCE: 22

Met Glu Phe Gln Thr Gln Val Phe Val Phe Val Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Ile Thr Cys Lys Ala Ser Gln Asn
```

```
                35                  40                  45
Val Arg Thr Ala Val Ala Trp Tyr Gln Gln Lys Pro Gly Gln Ser Pro
 50                  55                  60

Lys Ala Leu Ile Tyr Leu Ala Ser Asn Arg His Thr Gly Val Pro Asp
 65                  70                  75                  80

Arg Phe Thr Gly Ser Gly Ser Gly Thr Asp Phe Thr Leu Thr Ile Ser
                 85                  90                  95

Asn Val Gln Ser Glu Asp Leu Ala Asp Tyr Phe Cys Leu Gln His Trp
                100                 105                 110

Asn Tyr Pro Leu Thr Phe Gly Gly Gly Thr Lys Leu Glu Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 23
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 23

Met Asp Ser Gln Ala Gln Val Leu Met Leu Leu Leu Leu Trp Val Ser
  1               5                  10                  15

Gly Thr Cys Gly Asp Ile Val Met Ser Gln Ser Pro Ser Ser Leu Ala
                 20                  25                  30

Val Ser Val Gly Glu Lys Val Thr Met Ser Cys Lys Ser Ser Gln Ser
                 35                  40                  45

Leu Leu Tyr Ser Ser Asn Gln Lys Asn Tyr Leu Ala Trp Tyr Gln Gln
 50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Lys Ala Glu Asp Leu Ala Val Tyr
                100                 105                 110

Tyr Cys Gln Gln Tyr Tyr Ser Tyr Pro Leu Thr Phe Gly Ala Gly Thr
                115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160
```

```
Leu Leu Asn Asn Phe Tyr Pro Arg Glu Ala Lys Val Gln Trp Lys Val
            165                 170                 175

Asp Asn Ala Leu Gln Ser Gly Asn Ser Gln Glu Ser Val Thr Glu Gln
        180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 24
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 24

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
                20                  25                  30

Val Thr Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Phe Thr Phe Gly Ser Gly Thr
        115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
            165                 170                 175

Asp Asn Ala Leu Gln Ser Gly Asn Ser Gln Glu Ser Val Thr Glu Gln
        180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 25
<211> LENGTH: 239
<212> TYPE: PRT
<213> ORGANISM: Artificial
<220> FEATURE:
<223> OTHER INFORMATION: Description of artificial sequence: chimeric
      monoclonal antibody
```

<400> SEQUENCE: 25

```
Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Tyr Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 26
<211> LENGTH: 240
<212> TYPE: PRT
<213> ORGANISM: Artificial
<220> FEATURE:
<223> OTHER INFORMATION: Description of artificial sequence: chimeric monoclonal antibody

<400> SEQUENCE: 26

```
Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Ala Thr Asp
                85                  90                  95

Phe Thr Leu Thr Ile Ser Ser Val Gln Ala Glu Asp Leu Ala Asp Tyr
            100                 105                 110
```

```
His Cys Gly Gln Gly Tyr Ser Tyr Pro Tyr Thr Phe Gly Gly Gly Thr
        115                 120                 125

Lys Leu Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 27
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 27

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
                100                 105                 110

Tyr Cys Gln Gln Tyr Tyr Ser Tyr Pro Leu Thr Phe Gly Ala Gly Thr
        115                 120                 125

Lys Leu Glu Leu Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
```

<210> SEQ ID NO 28
<211> LENGTH: 234
<212> TYPE: PRT
<213> ORGANISM: Artificial
<220> FEATURE:
<223> OTHER INFORMATION: Description of artificial sequence: chimeric monoclonal antibody

<400> SEQUENCE: 28

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Lys Ala Glu Asp Leu Ala Val Tyr Tyr Cys Gln Gln Tyr Tyr
            100                 105                 110

Ser Tyr Pro Leu Thr Phe Gly Ala Gly Thr Lys Leu Glu Leu Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 29
<211> LENGTH: 117
<212> TYPE: PRT
<213> ORGANISM: Artificial
<220> FEATURE:
<223> OTHER INFORMATION: Description of artificial sequence: Translation of PCR product

<400> SEQUENCE: 29

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe

```
Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Asp Tyr Pro Trp Phe Ala Tyr Trp Gly Gln Gly Thr Leu
            100                 105                 110

Val Thr Val Ser Ala
        115

<210> SEQ ID NO 30
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 30

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Leu Gly Phe Gly Asn Ala Met Asp Tyr Trp Gly Gln Gly Thr
            100                 105                 110

Ser Val Thr Val Ser Ser
        115

<210> SEQ ID NO 31
<211> LENGTH: 116
<212> TYPE: PRT
<213> ORGANISM: Artificial
<220> FEATURE:
<223> OTHER INFORMATION: Description of artificial sequence: Translation
      of PCR product

<400> SEQUENCE: 31

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Ser Tyr Gly Ala Phe Asp Tyr Trp Gly Gln Gly Thr Thr Leu
```

-continued

```
                    100                 105                 110

Thr Val Ser Ser
        115

<210> SEQ ID NO 32
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 32

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
        115

<210> SEQ ID NO 33
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 33

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Leu Leu Arg Ala Met Asp Tyr Trp Gly Gln Gly Thr
            100                 105                 110

Ser Val Thr Val Ser Ser
        115

<210> SEQ ID NO 34
<211> LENGTH: 120
<212> TYPE: PRT
```

```
<213> ORGANISM: Artificial
<220> FEATURE:
<223> OTHER INFORMATION: Description of artificial sequence: Translation
      of PCR product

<400> SEQUENCE: 34

Gln Val His Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Phe
            20                  25                  30

Ala Tyr Met Ser Trp Ile Arg Gln Lys Pro Gly His Gly Phe Glu Trp
        35                  40                  45

Ile Gly Asp Ile Leu Pro Ser Ile Gly Arg Thr Ile Tyr Gly Glu Lys
    50                  55                  60

Phe Glu Asp Lys Ala Thr Leu Asp Ala Asp Thr Val Ser Asn Thr Ala
65                  70                  75                  80

Tyr Leu Glu Leu Asn Ser Leu Thr Ser Glu Asp Ser Ala Ile Tyr Tyr
                85                  90                  95

Cys Ala Arg Gly Glu Gly Tyr Gly Ala Trp Phe Ala Tyr Trp Gly Gln
            100                 105                 110

Gly Thr Leu Val Thr Val Ser Ala
        115                 120

<210> SEQ ID NO 35
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 35

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 36
<211> LENGTH: 106
<212> TYPE: PRT
<213> ORGANISM: Artificial
<220> FEATURE:
<223> OTHER INFORMATION: Description of artificial sequence: Translation
      of PCR product

<400> SEQUENCE: 36

Gln Ile Val Leu Thr Gln Ser Pro Ala Ile Met Ser Ala Ser Pro Gly
1               5                   10                  15
```

Glu Lys Val Thr Ile Thr Cys Ser Ala Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Lys Leu Glu Ile Lys
            100                 105

<210> SEQ ID NO 37
<211> LENGTH: 107
<212> TYPE: PRT
<213> ORGANISM: Artificial
<220> FEATURE:
<223> OTHER INFORMATION: Description of artificial sequence: Translation
      of PCR product

<400> SEQUENCE: 37

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
                20                  25                  30

Val Ala Trp Tyr Gln Gln Lys Pro Gly Gln Ser Pro Lys Ala Leu Ile
            35                  40                  45

Tyr Leu Ala Ser Asn Arg His Thr Gly Val Pro Asp Arg Phe Thr Gly
 50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Gly Gly Thr Lys Leu Glu Ile Lys
            100                 105

<210> SEQ ID NO 38
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 38

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 39
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 39

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys

<210> SEQ ID NO 40
<211> LENGTH: 112
<212> TYPE: PRT
<213> ORGANISM: Artificial
<220> FEATURE:
<223> OTHER INFORMATION: Description of artificial sequence: Translation
      of PCR product

<400> SEQUENCE: 40

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 41
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 41

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Ala Thr Asp Phe Thr Leu Thr
65                  70                  75                  80

Ile Ser Ser Val Gln Ala Glu Asp Leu Ala Asp Tyr His Cys Gly Gln
                85                  90                  95

Gly Tyr Ser Tyr Pro Tyr Thr Phe Gly Gly Gly Thr Lys Leu Glu Ile
            100                 105                 110

Lys

<210> SEQ ID NO 42
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 42

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 43
<211> LENGTH: 107
<212> TYPE: PRT
<213> ORGANISM: Artificial
<220> FEATURE:
<223> OTHER INFORMATION: Description of artificial sequence: Translation
      of PCR product

<400> SEQUENCE: 43

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Lys Ala
65                  70                  75                  80

Glu Asp Leu Ala Val Tyr Tyr Cys Gln Gln Tyr Tyr Ser Tyr Pro Leu
                85                  90                  95

Thr Phe Gly Ala Gly Thr Lys Leu Glu Leu Lys
            100                 105

<210> SEQ ID NO 44
<211> LENGTH: 15
<212> TYPE: PRT
<213> ORGANISM: Artificial
<220> FEATURE:
<223> OTHER INFORMATION: Epitope

<400> SEQUENCE: 44

Met Asp Gln Trp Ser Thr Gln Asp Leu Tyr Asn Asn Pro Val Thr
1               5                   10                  15

<210> SEQ ID NO 45
<211> LENGTH: 15
<212> TYPE: PRT
<213> ORGANISM: Artificial
<220> FEATURE:
<223> OTHER INFORMATION: Epitope

<400> SEQUENCE: 45

Ser Thr Gln Asp Leu Tyr Asn Asn Pro Val Thr Ala Val Phe Asn
1               5                   10                  15

<210> SEQ ID NO 46
<211> LENGTH: 15
<212> TYPE: PRT
<213> ORGANISM: Artificial
<220> FEATURE:
<223> OTHER INFORMATION: Epitope

<400> SEQUENCE: 46

Leu Tyr Asn Asn Pro Val Thr Ala Val Phe Asn Tyr Gln Gly Leu
1               5                   10                  15

<210> SEQ ID NO 47
<211> LENGTH: 15
<212> TYPE: PRT
<213> ORGANISM: Artificial
<220> FEATURE:
<223> OTHER INFORMATION: Epitope

<400> SEQUENCE: 47

Pro Val Thr Ala Val Phe Asn Tyr Gln Gly Leu Trp Arg Ser Cys
1               5                   10                  15

<210> SEQ ID NO 48
<211> LENGTH: 15
<212> TYPE: PRT
<213> ORGANISM: Artificial
<220> FEATURE:
<223> OTHER INFORMATION: Epitope

<400> SEQUENCE: 48

Val Phe Asn Tyr Gln Gly Leu Trp Arg Ser Cys Val Arg Glu Ser
1               5                   10                  15

```
<210> SEQ ID NO 49
<211> LENGTH: 15
<212> TYPE: PRT
<213> ORGANISM: Artificial
<220> FEATURE:
<223> OTHER INFORMATION: Epitope

<400> SEQUENCE: 49

Gln Gly Leu Trp Arg Ser Cys Val Arg Glu Ser Ser Gly Phe Thr
1               5                   10                  15

<210> SEQ ID NO 50
<211> LENGTH: 15
<212> TYPE: PRT
<213> ORGANISM: Artificial
<220> FEATURE:
<223> OTHER INFORMATION: Epitope

<400> SEQUENCE: 50

Arg Ser Cys Val Arg Glu Ser Ser Gly Phe Thr Glu Cys Arg Gly
1               5                   10                  15

<210> SEQ ID NO 51
<211> LENGTH: 467
<212> TYPE: PRT
<213> ORGANISM: Artificial Sequence
<220> FEATURE:
<223> OTHER INFORMATION: chimeric monoclonal antibody

<400> SEQUENCE: 51

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240
```

```
Asp Lys Thr His Thr Cys Pro Pro Cys Pro Ala Pro Glu Leu Leu Gly
            245             250             255
Gly Pro Ser Val Phe Leu Phe Pro Pro Lys Pro Lys Asp Thr Leu Met
            260             265             270
Ile Ser Arg Thr Pro Glu Val Thr Cys Val Val Val Asp Val Ser His
            275             280             285
Glu Asp Pro Glu Val Lys Phe Asn Trp Tyr Val Asp Gly Val Glu Val
290             295             300
His Asn Ala Lys Thr Lys Pro Arg Glu Glu Gln Tyr Asn Ser Thr Tyr
305             310             315             320
Arg Val Val Ser Val Leu Thr Val Leu His Gln Asp Trp Leu Asn Gly
            325             330             335
Lys Glu Tyr Lys Cys Lys Val Ser Asn Lys Ala Leu Pro Ala Pro Ile
            340             345             350
Glu Lys Thr Ile Ser Lys Ala Lys Gly Gln Pro Arg Glu Pro Gln Val
            355             360             365
Tyr Thr Leu Pro Pro Ser Arg Glu Glu Met Thr Lys Asn Gln Val Ser
    370             375             380
Leu Thr Cys Leu Val Lys Gly Phe Tyr Pro Ser Asp Ile Ala Val Glu
385             390             395             400
Trp Glu Ser Asn Gly Gln Pro Glu Asn Asn Tyr Lys Thr Thr Pro Pro
                405             410             415
Val Leu Asp Ser Asp Gly Ser Phe Phe Leu Tyr Ser Lys Leu Thr Val
            420             425             430
Asp Lys Ser Arg Trp Gln Gln Gly Asn Val Phe Ser Cys Ser Val Met
            435             440             445
His Glu Ala Leu His Asn His Tyr Thr Gln Lys Ser Leu Ser Leu Ser
    450             455             460
Pro Gly Lys
465
```